US008383589B2

(12) United States Patent
Calvo et al.

(10) Patent No.: US 8,383,589 B2
(45) Date of Patent: Feb. 26, 2013

(54) AEGYPTIN AND USES THEREOF

(75) Inventors: Eric Calvo, Bethesda, MD (US);
Osvaldo Marinotti, Aliso Viejo, CA (US); Jose M. C. Ribeiro, Rockville, MD (US); Ivo M. Francischetti, Washington, DC (US)

(73) Assignees: The United States of America, as Represented by the Secretary, Department of Health and Human Services, Washington, DC (US); Regents of the University of California, Oakland, CA (US)

( * ) Notice: Subject to any disclaimer, the term of this patent is extended or adjusted under 35 U.S.C. 154(b) by 410 days.

(21) Appl. No.: 12/668,177

(22) PCT Filed: Jul. 7, 2008

(86) PCT No.: PCT/US2008/069349
§ 371 (c)(1),
(2), (4) Date: Jan. 7, 2010

(87) PCT Pub. No.: WO2009/009493
PCT Pub. Date: Jan. 15, 2009

(65) Prior Publication Data
US 2011/0189120 A1    Aug. 4, 2011

Related U.S. Application Data

(60) Provisional application No. 60/948,629, filed on Jul. 9, 2007, provisional application No. 60/982,241, filed on Oct. 24, 2007.

(51) Int. Cl.
*A61K 38/00*    (2006.01)
*A61K 38/36*    (2006.01)
(52) U.S. Cl. .................. 514/13.8; 514/13.5; 514/13.7
(58) Field of Classification Search .................. None
See application file for complete search history.

(56) References Cited

U.S. PATENT DOCUMENTS

| | | |
|---|---|---|
| 3,511,684 A | 5/1970 | Huffaker |
| 3,585,647 A | 6/1971 | Gajewski et al. |
| 4,215,051 A | 7/1980 | Schroeder et al. |
| 4,254,180 A | 3/1981 | Kline |
| 4,326,532 A | 4/1982 | Hammar |
| 4,331,697 A | 5/1982 | Kudo et al. |
| 4,521,564 A | 6/1985 | Solomon et al. |
| 4,526,714 A | 7/1985 | Feijen et al. |
| 4,600,652 A | 7/1986 | Solomon et al. |
| 4,634,762 A | 1/1987 | Feijen et al. |
| 4,642,242 A | 2/1987 | Solomon et al. |
| 4,676,974 A | 6/1987 | Hofmann et al. |
| 4,678,660 A | 7/1987 | McGary et al. |
| 4,678,671 A | 7/1987 | Feijen et al. |
| 4,683,195 A | 7/1987 | Mullis et al. |
| 4,683,202 A | 7/1987 | Mullis |
| 4,818,540 A | 4/1989 | Chien et al. |
| 4,873,191 A | 10/1989 | Wagner et al. |
| 4,908,773 A | 3/1990 | Pantoliano et al. |
| 4,946,778 A | 8/1990 | Ladner et al. |
| 4,965,188 A | 10/1990 | Mullis et al. |
| 4,973,493 A | 11/1990 | Guire |
| 4,979,959 A | 12/1990 | Guire |
| 5,263,992 A | 11/1993 | Guire |
| 5,288,707 A | 2/1994 | Metternich |
| 5,322,770 A | 6/1994 | Gelfand |
| 5,331,573 A | 7/1994 | Balaji et al. |
| 5,414,075 A | 5/1995 | Swan et al. |
| 5,436,850 A | 7/1995 | Eisenberg et al. |
| 5,512,329 A | 4/1996 | Guire et al. |
| 5,552,534 A | 9/1996 | Hirschmann et al. |
| 5,557,535 A | 9/1996 | Srinivasan et al. |
| 5,679,659 A | 10/1997 | Verhoeven et al. |
| 5,741,551 A | 4/1998 | Guire et al. |
| 5,811,515 A | 9/1998 | Grubbs et al. |
| 5,817,626 A | 10/1998 | Findeis et al. |
| 5,817,879 A | 10/1998 | Hirschmann et al. |
| 5,821,231 A | 10/1998 | Arrhenius et al. |
| 5,873,052 A | 2/1999 | Sharaf |
| 5,874,529 A | 2/1999 | Gilon et al. |
| 5,877,263 A | 3/1999 | Patnaik et al. |
| 5,884,230 A | 3/1999 | Srinivasan et al. |
| 5,885,779 A | 3/1999 | Sadowski et al. |
| 5,888,738 A | 3/1999 | Hendry |
| 6,235,888 B1 | 5/2001 | Pachuk et al. |
| 6,528,107 B2 | 3/2003 | Chinn et al. |

FOREIGN PATENT DOCUMENTS

| | | |
|---|---|---|
| EP | 0130756 | 1/1985 |
| EP | 0155832 | 9/1985 |
| WO | WO 98/01579 | 1/1998 |
| WO | WO 98/04274 | 2/1998 |
| WO | WO 99/25826 | 5/1999 |

OTHER PUBLICATIONS

Sun et al. Platelet May 2006;17:178-84.*
Valenzuela et al. Insect Biochem Mole Biol 2002;32:1199-1209.*
Ribeiro et al. BMC Genomics 1997;8:6.*
Calvo et al. (2007) The Journal of Biological Chemistry, 282(37):26928-26938, "Aegyptin, a Novel Mosquito Salivary Gland Protein, Specifically Binds to Collagen and Prevents Its Interaction with Platelet Glycoprotein VI, Integrin $\alpha 2\beta 1$, and von Willebrand Factor".
Database UniProt [Online] "RecName: Full=30 kDa salivary gland allergen Aed a 3; AltName: Allergen=Aed a 3; Flags: Precursor;", Accession No. 001949, Accessed Jun. 20, 2001.

(Continued)

*Primary Examiner* — Q. Janice Li
(74) *Attorney, Agent, or Firm* — Swanson & Bratschun LLC

(57) ABSTRACT

The present invention relates to the discovery of the Aegyptin gene and Aegyptin protein, a molecule that interacts with collagen and inhibits platelet adhesion, activation and aggregation. Novel biological tools, prophylactics, therapeutics, diagnostics, and methods of use of the foregoing are also disclosed.

7 Claims, 23 Drawing Sheets

OTHER PUBLICATIONS

Desai et al. (2006) Recent Patents on Cardiovascular Drug Discovery, 1:307-316, "Recent Developments in Antithrombotic Therapy: Will Sodium Warfarin Be a Drug of the Past?".

Lang et al. (2006) Recent Patents on Cardiovascular Drug Discovery, 1:69-80, "Inhibitors for Metastasis Development".

Sigalov (2008) Expert Opin. Ther. Targets, 12(6):677-692, "Novel mechanistic concept of platelet inhibition".

5,556,632, Sep. 17, 1996, Kohler et al.

Allen et al., (1979) "The Cambridge Crystallographic Data Centre: Computer-based Search, Retrieval, Analysis, and Display of Information," *Acta Cryst.*; B35:2331-2339.

Altschul et al. (1990) "Basic Local Alignment Search Tool;" *J. Mol. Biol.*; 215:403-410.

Andersen et al., (2003) Inhibition of Hemostasis by a High Affinity Biogenic Amine-binding Protein from the Saliva of a Blood-feeding Insect; *J. Biol. Chem.*; 278:4611-4617.

Asara et al. (2007) "Protein Sequences from Mastadon and Tyrannosaurus Rex Revealed by Mass Spectrometry;" *Science*; 316:280-285.

Askew et al., (1989) "Molecular Recognition with Convergent Functional Groups. Synthetic and Structural Studies with Model Receptor for Nucleic Acid Components;" *J. Am. Chem. Soc.*; 111:1082-1090.

Aszodi et al., (1997) "Protein Modeling by Multiple Sequence Threading and Distance Geometry;" *Proteins: Structure, Function, and Genetics*; Supp.1:38-42.

Atkinson et al., (2003) "Activation of GPVI by Collagen is Regulated by [alpha]2[beta]1 and Secondary Mediators;" *J. Thromb. Haemost.*; 1:278-1287.

Auger et al., (2005) "Adhesion of Human and Mouse Platelets to Collagen under Shear: A Unifying Model;" *FASEB J.*; 19:825-827.

Barnes et al. (1999) "Collagens and Atherosclerosis;" *Exp. Gerontol.*; 34:513-525.

Barnes et al., (2001) "Production and Characterization of Saratin, an Inhibitor of von Willebrand Factor-dependent Platelet Adhesion to Collagen," *Sem. Thromb. Hemostas.*; 27:337-347.

Bergum et al., (2001) "Role of Zymogen and Activated Factor X as Scaffolds for the Inhibition of the Blood Coagulation Factor VIIa-Tissue Factor Complex by Recombinant Nematode Anticoagulant Protein c2;" *J. Bioo. Chem.*; 276:10063-10071.

Bitter et al. (1987) "Expression and Secretion Vectors for Yeast;" *Methods Enzymol.*; 153:516-544.

Borman (1992) "New 3-D Search and De Novo Design Techniques Aid Drug Development;" *Chem. Eng. News*; 70:18-26.

Bozec et al., (2007) "Collagen Fibrils: Nanoscale Ropes;" *Biophys J.*; 92:70-75.

Brass (2005) "Did Dinosaurs Have Megakaryocytes? New Ideas about Platelets and Their Progenitors;" *J. Clin. Invest.*; 115:3329-3331.

Brassard et al., (1999) "Integrin Alpha-V-Beta-3-Mediated Activation of Apoptosis;" *Exp. Cell. Res.*; 251:33-45.

Brint et al., (1988) "Upperbound Procedures for the Identification of Similar Three-dimensional Chemical Structures;" *J. Comp.-Aided Mol. Des.*; 2:311-320.

Calvo et al., (2004) "The Transciptome of Adult Female Anopheles darlingi Salivary Glands;" *Insect Mol. Biol.*; 13:73-88.

Calvo et al., (2006) "Function and Evolution of a Mosquito Salivary Protein Family;" *J. Biol. Chem.*; 281:1935-1942.

Cazares-Raga et al., (2007) "GP35 ANOAL, and Abundant Acidic Glycoprotein of Female *Anopheles albimanus* Saliva;" *Insect Mol. Biol.*; 16:187-198.

Champagne et al., (1994) "Sialokinin I and II: Vasodilatory Tachykinins from the Yellow Fever Mosquito *Aedes aegypti;*" *Proc. Natl. Acad. Sci. USA*; 91:138-142.

Chen et al., (2003) "Reciprocal Signaling by Integrin and Nonintegrin Receptors during Collagen Activation of Platelets;" *Mol. Cell. Biol.*; 23:4764-4777.

Chien et al., (1991) "The Two-hybrid System: A Method to Identify and Clone Genes for Proteins that Interact with a Protein of Interest;" *Proc. Natl. Acad. Sci. USA*; 88:9578-9582.

Colbere-Garapin et al., (1981) "A New Dominant Hybrid Selective Marker for Higher Eukaryotic Cells;" *J. Mol. Biol.*; 150:1-14.

Cole et al., (1985) "The EBV-hybridoma Technique and Its Application to Human Lung Cancer;" *Monoclonal Antibodies and Cancer Therapy*; pp. 77-96.

Connolly et al. (1992) "An Inhibitor of Collagen-stimulated Platelet Activation from the Salivary Glands of the *Haementeria officinalis* Leech;" *J. Biol. Chem.*; 267:6893-6898.

Cooper et al. (1989) "A Novel Approach to Molecular Similarity;" *J. Comp-Aided Mol. Des.*; 3:253-259.

Cote et al. (1983) "Generation of Human Monoclonal Antibodies Reactive with Cellular Antigens;" *Proc. Natl. Acad. Sci. USA*; 80:2026-2030.

Cruz et al. (2005) "The Platelet Glycoprotein Ib-von Willebrand Factor Interaction Activates the Collagen Receptor [alpha]2[beta]1 to Bind Collagen: Activation-dependent Conformational Change of the Alpha-2-I Domain;" *Blood*; 105:1986-1991.

Davi et al., (2007) "Platelet Activation and Atherothrombosis;" *N. Engl. J. Med.*; 357:2482-2494.

Davis et al., (2004) "Saratin (an Inhibitor of Platelet-collagen Interaction) Decreases Platelet Aggregation and Homocysteine-mediated Postcarotid Endarterectomy Intimal Hyperplasia in a Dose-dependent Manner;" *Am. J. Surg.*; 188:778-785.

Denis et al., (1998) "A Mouse Model of Severe von Willebrand Disease: Defects in Hemostasis and Thrombosis;" *Proc. Natl. Acad. Sci. USA*; 95:9524-9529.

Egles et al., (2008) "Denatured Collagen Modulates the Phenotype of Normal and Wounded Human Skin Equivalents;" *J. Invest. Dermatol.*; 128:1830-1837.

Engvall (1980) "Enzyme Immunoassay ELISA and EMIT;" *Methods Enzymol.*; 70:419-439.

Erickson et al., (1990) "Design, Activity, and 2.8 A Crystal Structure of a C2 Symmetric Inhibitor Complexed to HIV-1 Protease;" *Science*; 249:527-533.

Farmer et al., (1982) "Speculations on the Design of Nonpeptidic Peptidomimetics;" *Trends Pharm. Sci.*; 3:362-365.

Farndale et al., (2004) "The Role of Collagen in Thrombosis and Hemostasis;" *J. Thromb. Haemost.*; 2:561-573.

Fetrow et al., (1998) "Method for Prediction of Protein Function from Sequence Using the Sequence-to-Structure-to-Function Paradigm with Application to Glutaredoxins/Thioredoxins an T1 Ribonucleases;" *J. Mol. Biol.*; 281:949-968.

Fetrow et al., (1998) "Functional Analysis of the *Escherichia coli* Genome Using the Sequence-to-Structure-to-Function Paradigm: Identification of Proteins Exhibiting the Glutaredoxin/Thioredoxin Disulfide Oxidoreductase Activity;" *J. Mol. Biol.*; 282:703-711.

Fields et al., (1989) "A Novel Genetic System to Detect Protein-Protein Interactions;" *Nature*; 340:245-246.

Fox et al., (2007) "Approaching the Golden Age of National Product Pharmaceuticals from Venom Libraries: An Overview from Toxins and Toxin-derivatives Currently Involved in Therapeutic or Diagnostic Applications;" *Curr. Pharm. Des.*; 13:2927-2934.

Francischetti et al., (1997) "Convulxin, a Potent Platelet-aggregating Protein from *Crotalus durissus terrificus* Venom, Specifically Binds to Platelets;" *Toxicon.*; 35:1217-1228.

Francischetti et al., (2000) "Purification, Cloning, Expression, and Mechanism of Acion of a Novel Platelet Aggregation Inhibitor from the Salivary Gland of the Blood-sucking Bug, *Rhodnius prolixus;*" *J. Biol. Chem.*; 275:12639-12650.

Francischetti et al., (2002) "Ixolaris, a Novel Recombinant Tissue Factor Pathway Inhibitor (TFPI) from the Salivary Gland of the Tick, *Ixodes scapularis*: Identification of Factor X and Factor Xa as Scaffolds for the Inhibition of Factor VIIa/Tissue Factor Complex;" *Blood*; 99:3602-3612.

Francischetti et al., (2002) "Toward a Catalog for the Transcripts and Proteins (Sialome) fom the Salivary Gland of the Malaria Vector *Anopheles gambiae*;" *J. Exp. Biol.*; 205:2429-2451.

Francischetti et al., (2007) "*Plasmodium falciparum*-infected Erythrocytes Induce Tissue Factor Expression in Endothelial Cells and Support the Assembly of Multimolecular Coagulation Complexes;" *J. Thromb. Haemost.*; 5:155-165.

Furie et al., (2005) "Thrombus Formation in Vivo;" *J. Clin. Invest.*; 115:3355-3362.

Gibbins (2004) "Platelet Adhesion Signalling and the Regulation of Thrombus Formation;" *J. Cell. Sci.*; 117:3415-3425.

Gordon (1989) "Transgenic Animals;" *Intl. Rev. Cytol.*; 115:171-229.

Gruner (2005) "Relative Antithrombotic Effect of Soluble GPVI Dimer compared with Anti-GPVI Antibodies in Mice;" *Blood*; 105:1492-1499.

Gu et al., (1994) "Deletion of a DNA Ploymerase Beta Gene Segment in T Cells Using Cell Type-specific Gene Targeting;" *Science*; 265:103-106.

Harsfalvi et al., (1995) "Calin from Hirudo Medicinalis, and Inhibitor of von Willebrand Factor Binding to Collagen under Static and Flow Conditions;" *Blood*; 85:705-711.

Heemskerk et al., (2005) "Platelet Collagen Receptors and Coagulation. A Characteristic Platelet Response as Possible Target for Antithrombotic Treatment;" *Trends Cardiovasc. Med.*; 15:86-92.

Heino (2007) "The Collagen Family Members as Cell Adhesion Proteins;" *BioEssays*; 29:1001-1010.

Hodgson (1991) "Data-directed Drug Design;" *Bio/Technology*; 9:19-21.

Houghten (1985) "General Method for the Rapid Solid-phase Synthesis of Large Numbers of Peptides: Specificity of Antigen-antibody Interaction at the Level of Individual Amino Acids;" *Proc. Natl. Acad, Sci. USA*; 82:5131-5135.

Huse et al., (1989) "Generation of a Large Combinatorial Library of Immunoglobulin Repertoire in Phage Lambda; " *Science*; 246:1275-1281.

Hutchison et al., (1978) "Mutagenesis at a Specific Position in a DNA Sequence;" *J. Biol. Chem*; 253:6551-6660.

Ingber (1990) "Fibronectin Controls Capillary Endothelial Cell Growth by Modulating Cell Shape;" *Proc. Natl. Acad. Sci. USA*; 87:3579-3583.

Inouye et al., (1985) "Up-promoter Mutations in the Ipp Gene of *Escherichia coli;*" *Nucleic Acids Res.*; 13:3101-3110.

International Search Report for PCT/US2008/069349; Mailing Date of ISR: Dec. 29, 2008.

Jandrot-Perrus et al., (2000) "Cloning, Characterization, and Functional Studies of Human and Mouse Glycoprotein VI: A Platelet-specific Collagen Receptor from the Immunoglobulin Superfamily;" *Blood*; 96:1798-1807.

Janknecht et al., (1991) "Rapid and Efficient Purification of Native Histidine-lagged Protein Expressed by Recombinant Vaccinia Virus;" *Proc. Natl. Acad. Sci. USA*; 88:8972-8976.

Jariyapan et al., (2006) "A Glycine- and Glutamate-rich Protein Is Female Salivary Gland-specific and Abundant in the Malaria Vector Anopheles dirus B (Diptea: Culicidae);" *J. Med. Entomol.*; 43:867-874.

Jarvis et al., (2002) "Distinct Roles of GPVI and Integrin [alpha]2[beta]1 in Platelet Shape Change and Aggregation Induced by Different Collagens;" *Br. J. Pharmacol.*; 137:107-117.

Jung et al., (1998) "Platelets Interact wit Soluble and Insoluble Collagens through Characteristically Different Reactions;" *J. Biol. Chem.*; 273:14827-14837.

Jung et al., (2000) "Signal-transducing Mechanisms Involved in Activation of the Platelet Collagen Receptor Integrin [alpha]2[beta]1;" *J. Biol. Chem.*; 275:8016-8026.

Kaltenbronn et al., (1990) "Renin Inhibitors Containing Isosteric Replacements of the Amide Bond Connecting the P3 and P2 Sites;" *J. Med. Chem.*; 33:838-845.

Kato et al., (2003) "The Contribution of Glycoprotein VI to Stable Platelet Adhesion and Thrombus Formation Illustration by Targeted Gene Deletion;" *Blood*; 102:1701-1707.

Keller et al., (1993) "Cloning of the cDNA and Expression of Moubatin, an Inhibitor of Platelet Aggregation;" *J. Biol. Chem.*; 268:5450-5456.

Kelly et al., (2000) "Enhanced Genome Annotation Using Structural Profiles in the Program 3D-PSSM;" *J. Mol. Biol.*; 299:499-519.

Kemp (1990) "Peptidomimetics and the Template Approach To Nucleation of Beta-sheets and Alpha-helices in Peptides;" *Trends Biotechnol.*; 8:249-255.

Khoshnoodi et al., (2006) "Molecular Recognition in the Assembly of Collagens; Terminal Noncollagenous Domains Are Key Recognition Modules in the Formation of Triple Helical Promoters;" *J. Biol. Chem.*; 281:38117-38121.

Kleinschnitz et al., (2007) "Targeting Platelets in Acute Experimental Stroke. Impact of Glycoprotein Ib, VI, and IIb/IIIa Blockade on Infarct Size, Functional Outcome, and Intracranial Bleeding;" *Circulation*; 115:2323-2330.

Knight et al., (1999) "Collagen-platelet Interaction: Gly-Pro-Hyp Is Uniquely Specific for Platelet GPVI and Mediates Platelet Activation by Collagen;" *Cardiovasc. Res.*; 41:450-457.

Kohler et al., (1975) "Continuous Cultures of Fused Cells Secreting Antibody of Predefined Specificity;" *Nature*; 256:495-497.

Konstantinides et al., (2006) "Distinct Antithrombotic Consequences of Platelet Glycoprotein IB-Alpha and VI Deficiency in a Mouse Model of Arterial Thrombosis;" *J. Thromb. Haemost.*; 4:2014-2021.

Kozbor et al., (1983) "The Production of Monoclonal Antibodies from Human Lymphocytes;" *Immunol. Today.*; 4:72-79.

Kulipers et al., (2003) "Complementary Roles of Glycoprotein VI and [alpha]2[beta]1 Integrin in Collagen-induced Thrombus Formation in Flowing Whole Blood ex Vivo;" *FASEB J.*; 17:685-687.

Lakso et al., (1992) "Targeted Oncogene Activation by Site-Specific Recombination in Transgenic Mice;" *Proc. Natl. Acad. Sci. USA*; 89:6232-6236.

Lam (1997) "Application of Combinatorial Library Methods in Cancer Research and Drug Discovery;" *Anti-Cancer Drug Des.*; 12:145-167.

Lasser et al., (2006) "ClqTNF-related Protein-1 (CTRP-1): A Vascular Wall Protein that Inhabits Collagen-induced Platelet Aggregation by Blocking VWF Binding to Collagen;" *Blood*; 107:423-430.

Lavitrano et al., (1989) "Sperm Cells as Vectors for Introducing Foreign DNA into Eggs: Genetic Transformation of Mice;" *Cell*; 57:717-723.

Leanna et al., (1996) "The Reverse Two-hybrid System: A Genetic Scheme for Selection against Specific Protein/Protein Interactions;" *Nucleic Acids Res.*; 24:3341-3347.

Lecut et al., (2004) "Identification of Residues within Human Glycoprotein VI Involved in the Binding to Collagen;" *J. Biol. Chem.*; 279:52293-52299.

Lewis et al., (1989) "Automated Site-directed Drug Design: The Concept of Spacer Skeletons for Primary Structure Generation;" *Proc. R. Soc. Lond. B*; 236:125-140.

Lewis et al., (1989) "Automated Site-directed Drug-Design: The Formation of Molecular Templates in Primary Structure Generation;" *Proc. R. Soc. Lond. B*; 236:141-162.

Li et al., (2007) "The Fab Fragment of a Novel Anti-GPVI Monoclonal Antibody, OM4, Reduces in Vivo Thrombosis without Bleeding Risk in Rats;" *Arteriocler. Thromb. Vasc. Biol.*; 27:1199-1205.

Lisman et al., (2006) "A Single High-affinity Binding Site for von Willebrand Factor in Collagen III, Identified Using Sythetic Triple-helical Peptides;" *Blood*; 108:3753-3756.

Lo (1983) "Transformation by Iontophoretic Microinjection of DNA: Multiple Integrations without Tandeni Insertions;" *Mol. Cell. Biol.*; 3:1803-1814.

Logan et al., (1984) "Adenovirus Tripartite Leader Sequence Enhances Translation of mRNAs Late after Infection;" *Proc. Natl. Acad. Sci. USA*; 81:3655-3659.

Lowman (1997) "Bacteriophage Display and Discovery of Peptide Leads for Drug Development;" *Annu. Rev. Biophys. Biomol. Struct.*; 26:401-424.

Lowy et al., (1980) "Isolation of Transforming DNA: Cloning the Hamster aprt Gene;" *Cell*; 22:817-823.

Mans et al., (2002) "Sayignygin, a Platelet Aggregation Inhibitor from the Soft Tick Ornithodoros savignyi, Presents the RGD Integrin Recognition Motif on the Kunitz-BPTI Fold;" *J. Biol. Chem.*; 277:21371-21378.

Maritz-Olivier et al., (2007) "Tick Anti-hemostatics: Targets for Future Vaccinations and Therapeutics;" *Trends Parasitol.*; 23:397-407.

Marshall et al., (1994) "Detection of HCV RNA by the Asymmetric Gap Ligase Chain Reaction;" *Genome Res.*; 4:80-84.

Marx et al., (2008) "Altered Thrombus Formation in von Willebrand Factor-deficient Mice Expressing von Willebrand Factor Variants with Defective Binding to Collagen or GPIIbIIIa;" *Blood*; 112:603-609.

Massberg et al., (2003) "A Crucial Role of Glycoprotein VI for Platelet Recruitment to the Injured Arterial Wall in Vivo;" *J. Exp. Med.*; 197:41-49.

Massberg et al., (2004) "Soluble Glycoprotein VI Dimer Inhibits Platelet Adhesion and Aggregation to the Injured Vessel Wall in Vivo;" *FASEB J.*; 18:397-399.

Mathis (1995) "Probing Molecular Interactions with Homogenous Techniques Based on Rare Earth Cryptates and Fluorescence Energy Transfer;" *Clin. Chem.*; 41:1391-1397.

Mathur et al., (2010) "Transgene-mediated Suppression of Dengue Viruses in the Salivary Glands of the Yellow Fever Mosquito, *Aedes aegypti*," *Insect Mol. Biol.*, 19:753-763.

McKinlay et al., (1989) "Rational Designnnnnof Antiviral Agents;" *Annu. Rev. Pharmacol. Toxicol.*; 29:111-122.

Merrifield (1963) "Solid Phase Peptide Sythesis, I. The Synthesis of a Tetrapeptide;" *J. Am. Chem. Soc.*; 85:2149-2154.

Miura et al., (2002) "Analysis of the Interaction of Platelet Collagen Receptor Glycoprotein VI (GPVI) with Collagen;" *J. Biol. Chem.*; 277:46197-46204.

Moroi et al., (1997) Analysis of the Involvement of the von Willebrand Factor-Glycoprotein Ib Interaction in Platelet Adhesion to a Collagen-coated Surface under Flow Conditions; *Blood*; 90:4413-4424.

Morrison et al., (1984) "Chimeric Human Antibody Molecules: Mouse Antigen-binding Domains with Human Constant Region Domains;" *Proc. Natl. Acad. Sci. USA*; 81:6851-6855.

Morton et al., (1995) "Integrin [alpha]2[beta]1-independent Activation of Platelets by Simple Collagen-like Peptides: Collagen Tertiary (Triple-helical) and Quaternary (Polymeric) Structures Are Sufficient Aloe for [alpha]2[beta]1-independent Platelet Reactivity;" *Biochem. J.*; 306:337-344.

Mulligan et al., (1981) "Selection for Animal Cells that Express the *Escherichia coli* Gene Coding for Xanthine-Guanine Phosphoribosyltransferase;" *Proc. Natl. Acad. Sci. USA*; 78:2072-2076.

Munnix et al., (2005) "The Glycoprotein VI-Phospholipase C[gamma]2 Signaling Pathway Controls Thrombus Formation Induced by Collagen and Tissue Factor in Vitro and in Vivo," *Arterioscler, Thromb. Vasc. Biol.*; 25:2673-2678.

Nakamura et al., (1998) "Platelet Adhesion to Native Type 1 Collagen Fibrils;" *J. Biol. Chem.*; 273:4338-4344.

Nazareth et al., (2006) "Antithrombotic Properties of Ixolaris, a Potent Inhibitor of the Extrinsic Pathway of the Coagulation Cascade;" *Thromb. Haemost.*; 96:7-13.

Nene et al., (2007) "Genome Sequence of *Aedes aegypti*, a Major Arbovirus Vector;" *Science*; 316:1718-1723.

Neuberger et al., (1984) "Recombinant Antibodies Possessing Novel Effector Functions;" *Nature*; 312:604-610.

Nieswandt et al., (2001) "Long-term Antithrombotic Protection by in Vivo Depletion of Platelet Glycoprotein VI in Mice;" *J. Exp. Med.*; 193:459-469.

Nieswandt et al., (2003) "Platelet-Collagen Interaction: Is GPVI the Central Receptor?" *Blood*; 102:449-461.

O'Hare et al., (1981) "Transformation of Mouse Fibroblasts to Methotrexate Resistance by a Recombinant Plasmid Expressing a Prokaryotic Dihydrofolate Reductase;" *Proc. Natl. Acad. Sci. USA*; 78:1527-1531.

Ohlmann et al., (2008) "Ex Vivo Inhibition of Thrombus Formation by an Anti-glycoprotein VI Fab Fragment in Non-human Primates without Modification of Glycoprotein VI Expression;" *J. Thromb. Haemost.*; 6:1003-1011.

Orlandi et al., (1989) "Cloning Immunoglobulin Variable Domains for Expression by the Polymerase Chain Reaction;" *Proc. Natl. Acad. Sci. USA*; 86:3833-3837.

Pabo et al., (1986) "Computer-aided Model-building Strategies for Protein Design;" *Biochem.*; 25:5987-5991.

Pearson et al., (1988) "Improved Tools for Biological Sequence Comparison;" *Proc. Natl. Acad. Sci. USA*; 85:2444-2448.

Penz et al., (2005) "Human Atheromatous Plaques Stimulate Thrombus Formation by Activating Platelet Glycoprotein VI;" *FASEB J.*; 19:898-909.

Perry et al., (1984) "Disulfide Bond Engineered into T4 Lysozyme: Stabilization of the Protein Toward Thermal Inactivation;" *Science*; 226:555-557.

Perry et al., (1986) "Unpaired Cysteine-54 Interferes with the Ability of an Engineered Disulfide to Stabilize T4 Lysozyme;" *Biochem.*; 25:733-739.

Perry et al., (1989) "The Use of 3D Modelling Databases for Identifying Structure Activity Relationships;" *QSAR: Quantitative Structure-Activity Relationships in Drug Design*; Alan R. Liss, Inc.; pp. 189-193.

Phizicky et al., (1995) "Protein—Protein Interactions: Methods for Detection and Analysis;" *Microbiol. Rev.*; 59:94-123.

Raines et al., (2000) "The Extracellular Matrix Dynamically Regulates Smooth Muscle Cell Responsiveness to PDGF[alpha];" *Ann. NY Acad. Sci.*; 902:39-52.

Raynal et al., (2006) "Use of Synthetic Peptides to Locate Novel Integrin [alpha]2[beta]1-binding Motifs in Human Collagen III;" *J. Biol. Chem.*; 281:3821-3831.

Ribeiro et al., (1984) "Salivary Apryase of *Aedes aegypti*: Characterization and Secretory Fate;" *Comp. Biochem, Physiol.*; 79B: 81-86.

Ribeiro et al., (1993) "Reversible Binding of Nitric Oxide by a Salivary Hemc Protein from a Bloodsucking Insect;" *Science*; 260:539-541.

Ribeiro et al., (2001) "Platelet-activating-factor-hydrolyzing Phospholipase C in the Salivary Glands and Saliva of the Mosquito Culex quinquefasciatus;" *J. Exp. Biol.*; 204:3887-3894.

Ribeiro et al., (2003) "Role of Arthropod Saliva in Blood Feeding: Sialome and Post-sialome Perspectives:" *Annu. Rev. Entomol.*; 48:73-88.

Ribeiro et al., (2004) "An Insight into the Salivary Transcriptome and Proteome of the Adult Female Mosquito Culex pipiens quinquefasciatus;" *Insect Biochem. Mol. Biol.*; 34:543-563.

Ribeiro et al., (2007) "An Annotated Catalogue of Salivary Gland Transcripts in the Adult Female Mosquito, *Aedes aegypti*;" *BMC Genomics*; 8:6-32.

Richardson et al., (2000) "Crystal Structure of the Human [alpha]-thrombin-haemadin Complex: An Exosite II-binding Inhibitor;" *EMBO J.*; 19:5650-5660.

Ripka (1988) "Computers Picture the Perfect Drug;" *New Scientist*; Jun. 16, 1988:54-57.

Rosen et al., (2001) "Laser-induced Noninvasive Vascular Injury Models in Mice Generate Platelet- and Congulation-dependent Thrombi;" *Am. J. Pathol.*; 158:1613-1622.

Rouvinen et al., (1988) "Computer-aided Drug Design;" *Acta Pharm. Fennica*; 97:159-166.

Ruggeri (2002) "Platelets in Artherothrombosis;" *Nature Med.*; 8:1227-1234.

Ruther et al., (1983) "Easy Identification of cDNA Clones;" *EMBO J.*; 2:1791-1794.

Sachs et al., (2007) "In Vivo Thrombus Formation in Murine Models;" *Circ. Res.*; 100:979-991.

Sali et al., (1993) "Comparative Protein Modelling by Satisfaction of Spatial Restraints;" *J. Mol. Biol.*; 234:779-815.

Santerre et al., (1984) "Expression of Prokaryotic Genes for Hygromycin B and G418 Resistance as Dominant-selection Markers in Mouse L Cells;" *Gene*; 30:147-156.

Sarratt et al., (2005) "GPVI and [alpha]2[beta]1 Play Independent Critical Roles during Platelet Adhesion and Aggregate Formation to Collagen under Flow;" *Blood*; 1268-1277.

Savage et al., (1998) "Specific Synergy of Multiple Substrate-Receptor Interactions in Platelet Thrombus Formation under Flow;"*Cell*; 94:657-666.

Savage et al., (1999) "Influence of Fibrillar Collagen Structure on the Mechanisms of Platelet Thrombus Formation under Flow;" *Blood*; 94:2704-2715.

Sharp et al., (1988) "Codon Usage Patterns in *Escherichia coli, Bacillus subtillis, Saccharomyces cerevisiae, Schizosaccharomyces pomble, Drosophila melanogaster* and *Homo sapiens*; a Review of the Considerable Within-species Diversity:" *Nucleic Acids Res.*; 16:8207-8214.

Sigalov (2008) "Novel Mechanistic Concept of Platelet Inhibition;" *Expert Opin. Ther. Targets*; 12:677-692.

Smethurst et al., (2007) "Strutural Basis for the Platelet-Collagen Interaction, The Smallest Motif within Collagen that Recognizes and Activates Platelet Glycoprotein VI Contains Two Glycine-Proline-Hydroxyproline Triplets;" *J. Biol. Chem.*; 282:1296-1304.

Smith et al., (1983) "Molecular Engineering of the *Autographa californica* Nuclear Polyhedrosis Virus Genome: Deletion Mutations within the Polyhedrin Gene;" *J. Virol.*; 46:584-593.

Somasundaram et al., (1996) "Type I, II, III, IV, V, and VI Collagens Serve as Extracellular Ligands for the Isoforms of Platelet-derived Growth Factor (AA, BB, and AB);" *J. Biol. Chem.*; 271:26884-26891.

Somasundaram et al., (2000) "Collagens Serve as an Extracellular Store of Bioactive Interleukin 2;" *J. Biol. Chem.*; 275:38170-38175.

Somasundaram et al. (2002) "Interstitial Collagens I, III, and VI Sequester and Modulate the Multifunctional Cytokine Oncostatin M;" *J. Biol. Chem.*; 277:3242-3246.

Sowdhamini et al., (1997) "Structural and Functional Analogy between Pneumolysin and Proaerolysin;" *Protein Eng.*; 10:207-215.

Stanssens et al., (1996) "Anticoagulant Repertoire of the Hookworm *Aneylostoma caninum;*" *Proc. Natl. Acad. Sci USA*; 93:2149-2154.

Szybalska et al., (1962) "Genetics of Human Cell Lines, IV. DNA-mediated heritable Transformation of a Biochemical Trait;" *Proc. Natl. Acad. Sci. USA*; 48:2026-2034.

Takeda et al., (1985) "Construction of Chimaeric Processed Immunoglobulin Genes Containing Mouse Variable and Human Constant Region Sequences;" *Nature*; 314:452-454.

Thompson et al., (1989) "Germ Line Transmission annn Expressio of a Corrected HPRT Gene Produced by Gene Targeting in Embryonic Stem Cells;" *Cell*; 56:313-321.

Tokumasu et al., (2003) "Development and Application of Quantum Dots for Immunocytochemistry of Human Erythrocytes;" *J. Microscopy*: 211:256-261.

Toschi et al., (1997) "Tissue Factor Modulates the Thrombogenicity of Human Atherosclerotic Plaques;" *Circulation*; 95:594-599.

Uniprot Accession No. 001949 (Jun. 20, 2001).

Vaitukaitis et al., (1971) "A Method for Producing Specific Antisera with Small Doses of Immunogen;" *J. Clin. Endocrimol.*; 33:988-991.

Valenzuela et al., (1998) "Purification, Cloning, and Expression of an Apyrase from the Bed Bug *Cimex lectularius;*" *J. Biol. Chem.*; 273:30583-30590.

Valenzuela et al., (2002) "Toward a Description of the Sialome of the Adult Female Mosquito *Aedes aegypti*," *Insect Biochem. Mol. Biol.*, 32:1101-1122.

Van Der Putten et al., (1985) "Efficient Insertion of Genes into the Mouse Germ Line via Retroviral Vectors;" *Proc. Natl. Acad. Sci. USA*; 82:6148-6152.

Van Heeke et al., (1989) "Expression of Human Asparagine Synthetase in *Escherichia coli;*" *J. Biol. Chem.*; 264:5503-5509.

Van Zanten et al., (1995) "Recombinant Leech Antiplatelet Protein Specifically Blocks Platelet Deposition on Collagen Surfaces under Flow Conditions;" *Arterioscler. Thromb. Vasc. Biol.*; 15:1424-1431.

Veber et al., (1985) "The Design of Metabolically-stable Peptide Analogs;" *Trends Neurosci.*; 8:392-396.

Vilahur et al., (2004) "Antithrombotic Effects of Saratin on Human Atherosclerotic Plaques;" *Thromb. Haemost.*; 92:191-200.

Watson et al., (2005) "GPVI and Integrim [alpha]IIb[beta]3 Signaling in Platelets;" *J. Thromb. Haemost.*; 3:1752-1762.

Wells (1991) "Systematic Mutational Analyses of Protein-Protein Interfaces;" *Methods Enzymol.*; 202:390-411.

Wigler et al., (1977) "Transfer of Purified Herpes Virus Thymidine Kinase Gene to Cultured Mouse Cells;" *Cell*; 11:223-232.

Wigler et al., (1980) "Transformation of Mammalian Cells with an Amplifiable Dominant-acting Gene;" *Proc. Natl. Acad. Sci. USA*; 77:3567-3570.

Winter et al., (1991) "Man-made Antibodies;" *Nature*; 349:293-299.

Wiviott et al., (2007) "Prasugrel versus Clopidogrel in Patients with Acute Coronary Syndromes;" *N. Engl. J. Med.*; 357:2001-2015.

Yoshida et al., (2008) "Inhibitationof Collagen-induced Platelet Aggregation by Anopheline Antiplatelet Protein, a Saliva Protein from a Malaria Vector Mosquito;" *Blood*; 111:2007-2014.

Young (1998) "Yeast Two-hybrid: So Many Interactions, (in) so Little Time . . . " *Biol. Reprod.*; 58:302-311.

\* cited by examiner

FLOW ⇒

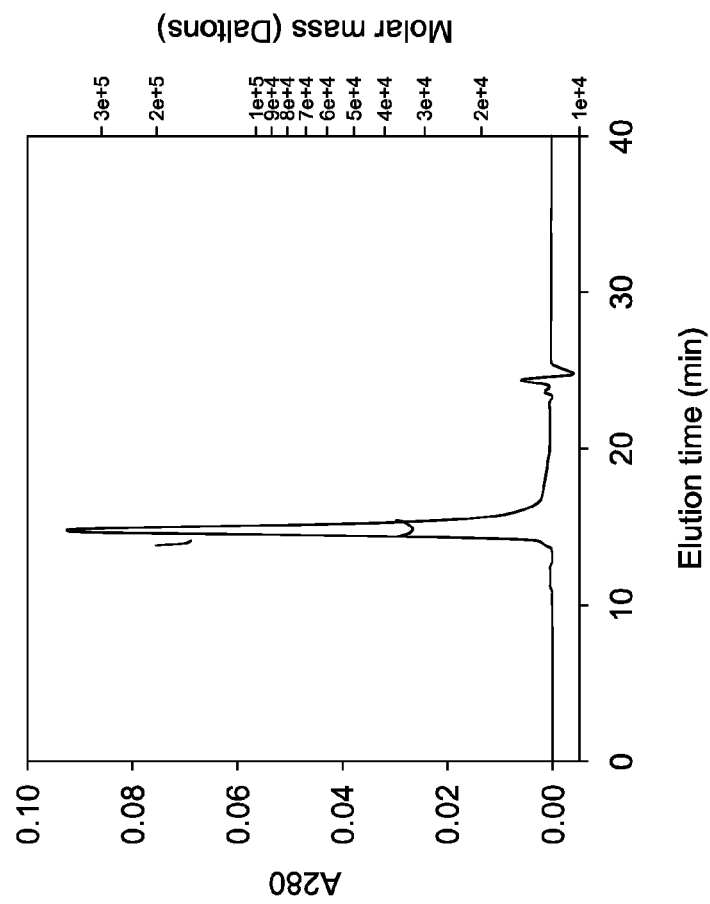
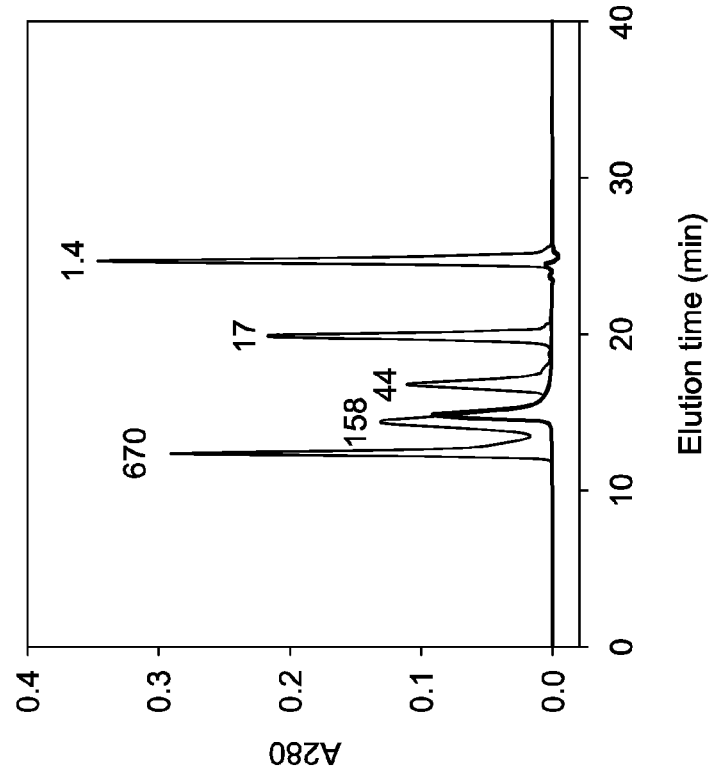
FIG. 8A
FIG. 8B

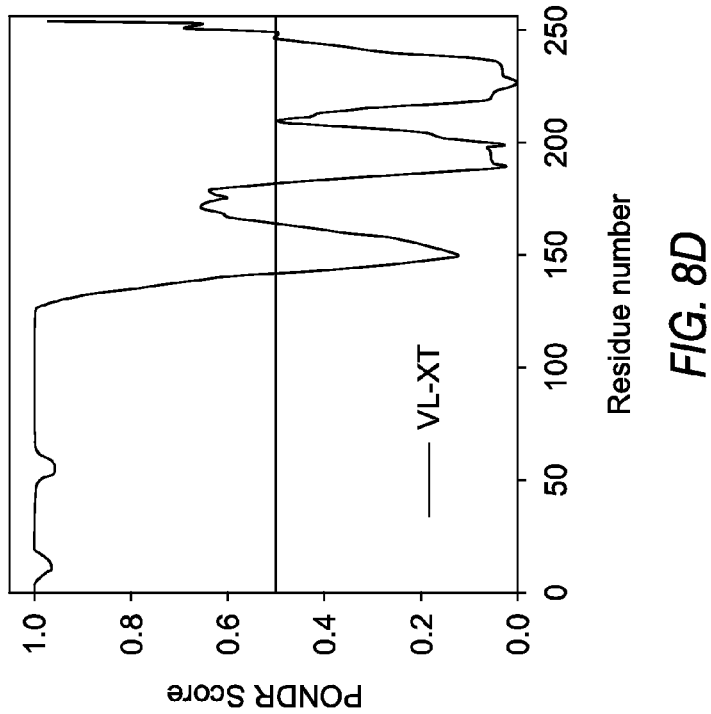
FIG. 8C
FIG. 8D
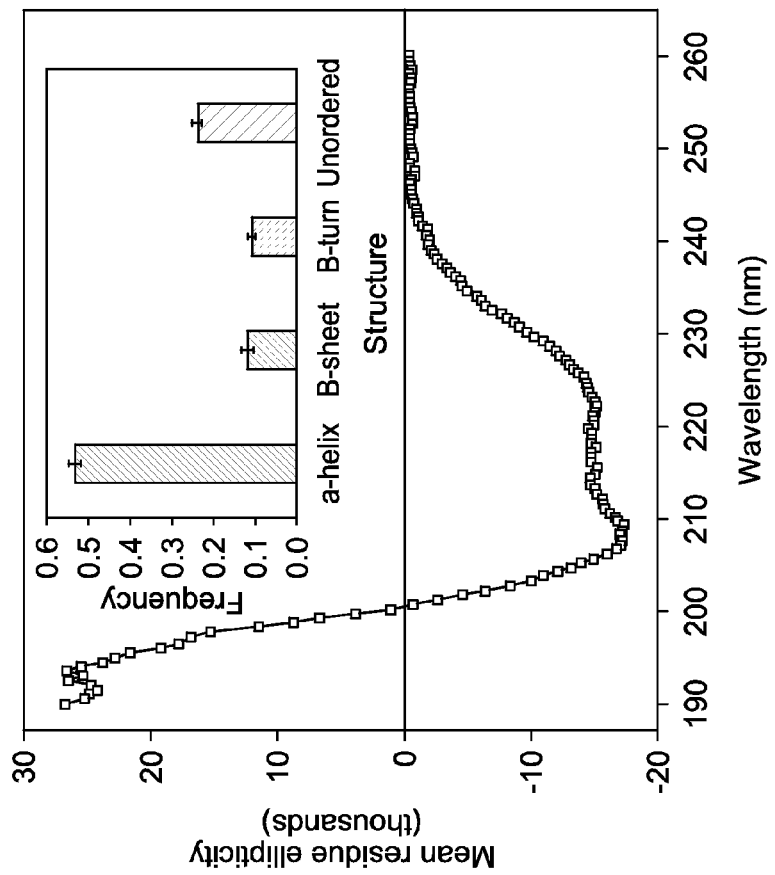
FIG. 8E

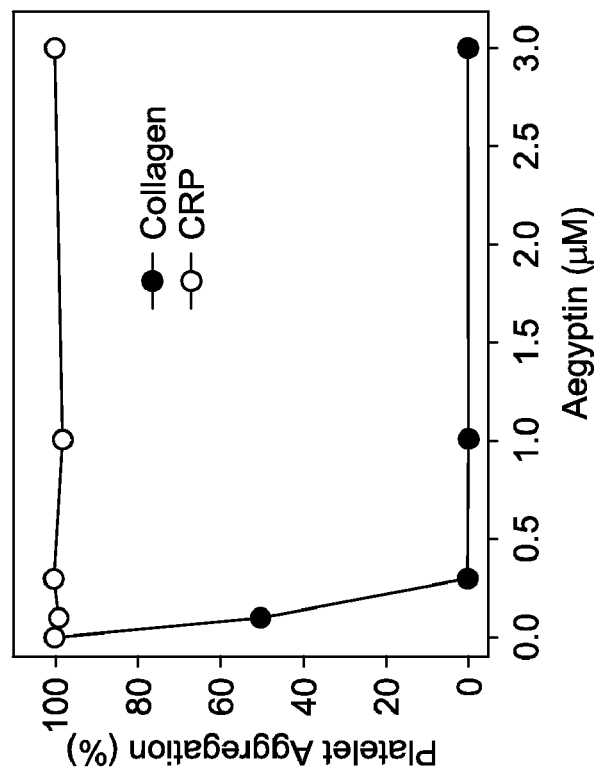
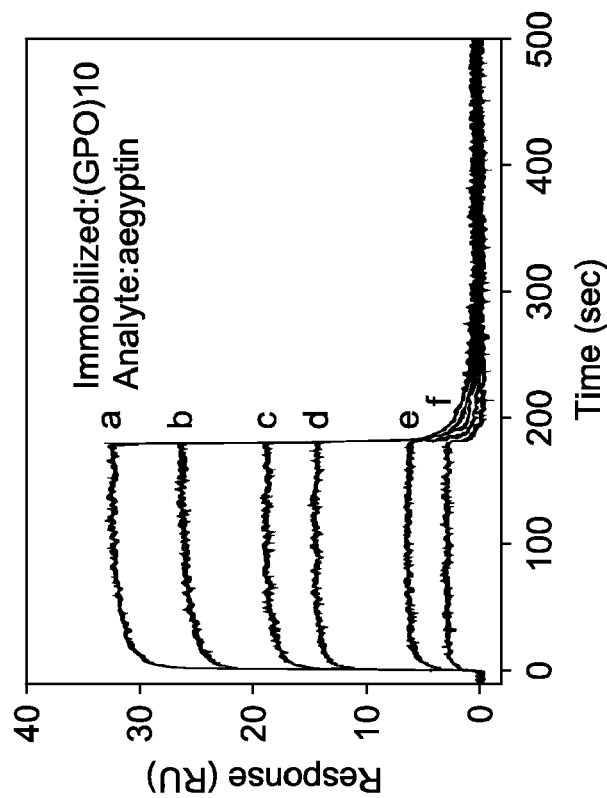
FIG. 10B
FIG. 10A

SEQUENCE LISTING

<160> NUMBER OF SEQ ID NOS: 22

<210> SEQ ID NO 1
<211> LENGTH: 822
<212> TYPE: DNA
<213> ORGANISM: Aedes aegypti

<400> SEQUENCE: 1

```
atgaaaccct tggttaaatt attcttgcta ttctgtctgg taggcattgt gctttccagg    60
cccatgcccg aagatgaaga accagtagcg gagggaggtg acgatgatgc aagcggagag   120
tctgagggcg aagaagaaac gaccgatgat gctggaggtg atggcggcga agaagaaat    180 gaaggtgaag aacatgctgg agataaggat gctggcggtg aagatactgg caagaggag    240 aatacaggac atgacgatgc tggtgaggaa gatgctggtg aggaagatgc tggtgaggaa   300
gatgctggcg aagaagatgc tggcgaagaa gatgctgaaa aagaggaagg agaaaaggaa   360
gacgccggag atgatgccgg aagtgatgat ggggaagagg atagtacagg aggtgacgaa   420
ggagaagata acgctgaaga cagtaaaggt agtgaaaaga acgatccggc cgatacatat   480
agacaggtgg ttgcattact agacaaggat accaaggtgg atcacatcca gagtgagtac   540
cttcgatcag cactgaacaa cgatttacaa tcagaagtga gagttccggt ggtggaagct   600
atcgggagga ttggagacta ttccaagatt caaggatgct tcaaatcgat gggtaaagat   660
gtaaaaaaag ttatcagcga agaggagaag aaatttaaga gctgcatgag taagaagaaa   720
agcgagtatc agtgctcgga ggacagtttt gcggctgcca agagcaaact ttcgccaata   780
acctctaaga ttaaatcctg tgtttcatcc aaaggacgtt aa                      822
```

<210> SEQ ID NO 2
<211> LENGTH: 273
<212> TYPE: PRT
<213> ORGANISM: Aedes aegypti

<400> SEQUENCE: 2

Met Lys Pro Leu Val Lys Leu Phe Leu Leu Phe Cys Leu Val Gly Ile

-continued

```
1               5                   10                  15

Val Leu Ser Arg Pro Met Pro Glu Asp Glu Glu Pro Val Ala Glu Gly
            20                  25                  30

Gly Asp Asp Asp Ala Ser Gly Glu Ser Glu Gly Glu Glu Glu Thr Thr
        35                  40                  45

Asp Asp Ala Gly Gly Asp Gly Gly Glu Glu Glu Asn Glu Gly Glu Glu
    50                  55                  60

His Ala Gly Asp Lys Asp Ala Gly Gly Glu Asp Thr Gly Lys Glu Glu
65                  70                  75                  80

Asn Thr Gly His Asp Asp Ala Gly Glu Glu Asp Ala Gly Glu Glu Asp
                85                  90                  95

Ala Gly Glu Glu Asp Ala Gly Glu Glu Asp Ala Gly Glu Glu Asp Ala
            100                 105                 110

Glu Lys Glu Glu Gly Glu Lys Glu Asp Ala Gly Asp Asp Ala Gly Ser
        115                 120                 125

Asp Asp Gly Glu Glu Asp Ser Thr Gly Gly Asp Glu Gly Glu Asp Asn
    130                 135                 140

Ala Glu Asp Ser Lys Gly Ser Glu Lys Asn Asp Pro Ala Asp Thr Tyr
145                 150                 155                 160

Arg Gln Val Val Ala Leu Leu Asp Lys Asp Thr Lys Val Asp His Ile
                165                 170                 175

Gln Ser Glu Tyr Leu Arg Ser Ala Leu Asn Asn Asp Leu Gln Ser Glu
            180                 185                 190

Val Arg Val Pro Val Val Glu Ala Ile Gly Arg Ile Gly Asp Tyr Ser
        195                 200                 205

Lys Ile Gln Gly Cys Phe Lys Ser Met Gly Lys Asp Val Lys Lys Val
    210                 215                 220

Ile Ser Glu Glu Glu Lys Lys Phe Lys Ser Cys Met Ser Lys Lys Lys
225                 230                 235                 240

Ser Glu Tyr Gln Cys Ser Glu Asp Ser Phe Ala Ala Ala Lys Ser Lys
                245                 250                 255

Leu Ser Pro Ile Thr Ser Lys Ile Lys Ser Cys Val Ser Ser Lys Gly
            260                 265                 270

Arg
```

<210> SEQ ID NO 3
<211> LENGTH: 822
<212> TYPE: DNA
<213> ORGANISM: Artificial Sequence
<220> FEATURE:
<223> OTHER INFORMATION: Codon-optimized aegyptin polynucleotide sequence for expression in human

<400> SEQUENCE: 3

```
atgaagcccc tggtgaagct gttcctgctg ttctgcctgg tgggcatcgt gctgagccgc     60
cccatgcccg aggacgagga gcccgtggcc gagggcggcg acgacgacgc cagcggcgag    120
agcgagggcg aggaggagac caccgacgac gccggcggcg acggcggcga ggaggagaac    180
gagggcgagg agcacgccgg cgacaaggac gccggcggcg aggacaccgg caaggaggag    240
aacaccggcc acgacgacgc cggcgaggag gacgccggcg aggaggacgc cggcgaggag    300
gacgccggcg aggaggacgc cggcgaggag gacgccgaga aggaggaggg cgagaaggag    360
gacgccggcg acgacgccgg cagcgacgac ggcgaggagg acagcaccgg cggcgacgag    420
ggcgaggaca acgccgagga cagcaagggc agcgagaaga acgaccccgc cgacacctac    480
cgccaggtgg tggccctgct ggacaaggac accaaggtgg accacatcca gagcgagtac    540
```

```
ctgcgcagcg ccctgaacaa cgacctgcag agcgaggtgc gcgtgcccgt ggtggaggcc    600
atcggccgca tcggcgacta cagcaagatc cagggctgct tcaagagcat gggcaaggac    660
gtgaagaagg tgatcagcga ggaggagaag aagttcaaga gctgcatgag caagaagaag    720
agcgagtacc agtgcagcga ggacagcttc gccgccgcca gagcaagct gagccccatc     780 accagcaaga tcaagagctg cgtgagcagc aagggccgct aa                       822
```

```
<210> SEQ ID NO 4
<211> LENGTH: 28
<212> TYPE: DNA
<213> ORGANISM: Artificial Sequence
<220> FEATURE:
<223> OTHER INFORMATION: PCR Primer

<400> SEQUENCE: 4
aggcccatgc ccgaagatga agaaccag                                       28

<210> SEQ ID NO 5
<211> LENGTH: 41
<212> TYPE: DNA
<213> ORGANISM: Artificial Sequence
<220> FEATURE:
<223> OTHER INFORMATION: PCR Primer

<400> SEQUENCE: 5
ttagtggtgg tggtggtggt gacgtccttt ggatgaaaca c                        41

<210> SEQ ID NO 6
<211> LENGTH: 12
<212> TYPE: PRT
<213> ORGANISM: Aedes aegypti

<400> SEQUENCE: 6

Arg Pro Met Pro Glu Asp Glu Glu Val Ala Glu Gly
1               5                   10

<210> SEQ ID NO 7
<211> LENGTH: 5
<212> TYPE: PRT
<213> ORGANISM: Aedes aegypti

<400> SEQUENCE: 7

Gly Glu Glu Asp Ala
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: 4Hyp

<400> SEQUENCE: 8

Gly Phe Xaa Gly Glu Arg
1               5

<210> SEQ ID NO 9
<211> LENGTH: 10
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: misc_feature
<222> LOCATION: (4)..(4)
<223> OTHER INFORMATION: 4Hyp
<220> FEATURE:
<221> NAME/KEY: misc_feature
<222> LOCATION: (10)..(10)
<223> OTHER INFORMATION: 4Hyp

<400> SEQUENCE: 9

Arg Gly Gln Xaa Gly Val Met Gly Phe Xaa
1               5                   10

<210> SEQ ID NO 10
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: 4Hyp
<220> FEATURE:
<221> NAME/KEY: misc_feature
<222> LOCATION: (6)..(6)
<223> OTHER INFORMATION: 4Hyp
<220> FEATURE:
<221> NAME/KEY: misc_feature
<222> LOCATION: (9)..(9)
<223> OTHER INFORMATION: 4Hyp
<220> FEATURE:
<221> NAME/KEY: misc_feature
<222> LOCATION: (12)..(12)
<223> OTHER INFORMATION: 4Hyp
<220> FEATURE:
<221> NAME/KEY: misc_feature
<222> LOCATION: (15)..(15)
<223> OTHER INFORMATION: 4Hyp
<220> FEATURE:
<221> NAME/KEY: misc_feature
<222> LOCATION: (18)..(18)
<223> OTHER INFORMATION: 4Hyp
<220> FEATURE:
<221> NAME/KEY: misc_feature
<222> LOCATION: (21)..(21)
<223> OTHER INFORMATION: 4Hyp
<220> FEATURE:
<221> NAME/KEY: misc_feature
<222> LOCATION: (24)..(24)
<223> OTHER INFORMATION: 4Hyp
<220> FEATURE:
<221> NAME/KEY: misc_feature
<222> LOCATION: (27)..(27)
<223> OTHER INFORMATION: 4Hyp
<220> FEATURE:
<221> NAME/KEY: misc_feature
<222> LOCATION: (30)..(30)
<223> OTHER INFORMATION: 4Hyp

<400> SEQUENCE: 10

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa
            20                  25                  30

<210> SEQ ID NO 11
<211> LENGTH: 37
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
```

```
<222> LOCATION: (3)..(3)
<223> OTHER INFORMATION: 4Hyp
<220> FEATURE:
<221> NAME/KEY: misc_feature
<222> LOCATION: (6)..(6)
<223> OTHER INFORMATION: 4Hyp
<220> FEATURE:
<221> NAME/KEY: misc_feature
<222> LOCATION: (9)..(9)
<223> OTHER INFORMATION: 4Hyp
<220> FEATURE:
<221> NAME/KEY: misc_feature
<222> LOCATION: (12)..(12)
<223> OTHER INFORMATION: 4Hyp
<220> FEATURE:
<221> NAME/KEY: misc_feature
<222> LOCATION: (15)..(15)
<223> OTHER INFORMATION: 4Hyp
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: 4Hyp
<220> FEATURE:
<221> NAME/KEY: misc_feature
<222> LOCATION: (24)..(24)
<223> OTHER INFORMATION: 4Hyp
<220> FEATURE:
<221> NAME/KEY: misc_feature
<222> LOCATION: (27)..(27)
<223> OTHER INFORMATION: 4Hyp
<220> FEATURE:
<221> NAME/KEY: misc_feature
<222> LOCATION: (30)..(30)
<223> OTHER INFORMATION: 4Hyp
<220> FEATURE:
<221> NAME/KEY: misc_feature
<222> LOCATION: (33)..(33)
<223> OTHER INFORMATION: 4Hyp
<220> FEATURE:
<221> NAME/KEY: misc_feature
<222> LOCATION: (36)..(36)
<223> OTHER INFORMATION: 4Hyp

<400> SEQUENCE: 11

Gly Cys Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Cys Xaa Gly
        35

<210> SEQ ID NO 12
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (21)..(21)
<223> OTHER INFORMATION: 4Hyp

<400> SEQUENCE: 12

Gly Pro Cys Gly Pro Pro Gly Pro Pro Gly Pro Pro Gly Pro Pro Gly
1               5                   10                  15

Pro Pro Gly Phe Xaa Gly Glu Arg Gly Pro Gly Pro Pro Gly Pro Pro
            20                  25                  30

Pro Gly Pro Pro Gly Pro Pro Gly Pro Cys
        35                  40
```

```
<210> SEQ ID NO 13
<211> LENGTH: 63
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (21)..(21)
<223> OTHER INFORMATION: 4Hyp
<220> FEATURE:
<221> NAME/KEY: misc_feature
<222> LOCATION: (30)..(30)
<223> OTHER INFORMATION: 4Hyp
<220> FEATURE:
<221> NAME/KEY: misc_feature
<222> LOCATION: (36)..(36)
<223> OTHER INFORMATION: 4Hyp
<220> FEATURE:
<221> NAME/KEY: misc_feature
<222> LOCATION: (45)..(45)
<223> OTHER INFORMATION: 4Hyp

<400> SEQUENCE: 13

Gly Pro Cys Gly Pro Pro Gly Pro Pro Gly Pro Pro Gly Pro Pro Gly
1               5                   10                  15

Pro Pro Gly Pro Xaa Gly Pro Ser Gly Pro Arg Gly Gln Xaa Gly Val
            20                  25                  30

Met Gly Phe Xaa Gly Pro Lys Gly Asn Asp Gly Ala Xaa Gly Pro Pro
        35                  40                  45

Gly Pro Pro Gly Pro Pro Gly Pro Pro Gly Pro Pro Gly Pro Cys
    50                  55                  60

<210> SEQ ID NO 14
<211> LENGTH: 4
<212> TYPE: PRT
<213> ORGANISM: Aedes aegypti

<400> SEQUENCE: 14

Ser Lys Gly Arg
1

<210> SEQ ID NO 15
<211> LENGTH: 4
<212> TYPE: PRT
<213> ORGANISM: Aedes aegypti

<400> SEQUENCE: 15

Asp Pro Ala Asp
1

<210> SEQ ID NO 16
<211> LENGTH: 4
<212> TYPE: PRT
<213> ORGANISM: Aedes aegypti

<400> SEQUENCE: 16

Arg Gln Val Val
1

<210> SEQ ID NO 17
```

-continued

```
<211> LENGTH: 4
<212> TYPE: PRT
<213> ORGANISM: Aedes aegypti

<400> SEQUENCE: 17

Gly His Asp Asp
1

<210> SEQ ID NO 18
<211> LENGTH: 4
<212> TYPE: PRT
<213> ORGANISM: Aedes aegypti

<400> SEQUENCE: 18

Gln Glu Cys Phe
1

<210> SEQ ID NO 19
<211> LENGTH: 4
<212> TYPE: PRT
<213> ORGANISM: Aedes aegypti

<400> SEQUENCE: 19

Asp Asp Ala Gly
1

<210> SEQ ID NO 20
<211> LENGTH: 4
<212> TYPE: PRT
<213> ORGANISM: Aedes aegypti

<400> SEQUENCE: 20

Gly Glu Glu Asp
1

<210> SEQ ID NO 21
<211> LENGTH: 4
<212> TYPE: PRT
<213> ORGANISM: Aedes aegypti

<400> SEQUENCE: 21

Gly Gly Asp Glu
1

<210> SEQ ID NO 22
<211> LENGTH: 137
<212> TYPE: PRT
<213> ORGANISM: Aedes aegypti

<400> SEQUENCE: 22

Gly Gly Asp Glu Gly Asp Asn Ala Glu Asp Ser Lys Gly Ser Lys Glu
1               5                   10                  15

Lys Asn Asp Pro Ala Asp Thr Tyr Arg Gln Val Val Ala Leu Leu Asp
            20                  25                  30

Lys Asp Thr Lys Val Asp His Ile Gln Ser Glu Tyr Leu Arg Ser Ala
        35                  40                  45

Leu Asn Asn Asp Leu Gln Ser Glu Val Arg Val Pro Val Val Glu Ala
    50                  55                  60

Ile Gly Arg Ile Gly Asp Tyr Ser Lys Ile Gln Gly Cys Phe Lys Ser
65                  70                  75                  80

Met Gly Lys Asp Val Lys Lys Val Ile Ser Glu Glu Lys Lys Phe
                85                  90                  95

Lys Ser Leu Met Ser Lys Lys Lys Ser Glu Tyr Gln Cys Ser Glu Asp
```

-continued

```
            100                 105                 110
Ser Phe Ala Ala Ala Lys Ser Lys Leu Ser Pro Ile Thr Ser Lys Ile
        115                 120                 125

Lys Ser Cys Val Ser Ser Lys Gly Arg
    130                 135
```

AEGYPTIN AND USES THEREOF

PRIORITY CLAIM

This application claims the benefit of U.S. Provisional Patent Application No. 60/948,629, filed Jul. 9, 2007 and U.S. Provisional Patent Application No. 60/982,241, filed Oct. 24, 2007, the disclosures of which are incorporated in their entirety herein by reference.

FIELD OF THE INVENTION

Aspects of the present invention concern the discovery of a gene that encodes Aegyptin, a protein that interacts with collagen, and inhibits platelet adhesion, activation and aggregation. Novel biological tools, prophylactics, therapeutics, diagnostics, and methods of use of the foregoing are embodiments.

BACKGROUND OF THE INVENTION

Blood-sucking arthropod saliva is a rich source of molecules that affect hemostasis,[1] including vasodilators[2,3] and inhibitors of blood coagulation[4,5] and platelet aggregation.[6-8] Among the platelet inhibitors, salivary lipocalins bind to and remove pro-aggregatory amines such as ADP, epinephrine, and serotonin,[8-10] while RGD-containing peptides block integrin $\alpha_{IIb}\beta_3$ interaction with fibrinogen.[7] In addition, enzymes such as apyrases and lipid acethyl hydrolases degrade biologically active molecules such as ADP and PAF, respectively.[11,12] Further, specific antagonists of collagen-induced platelet aggregation/adhesion have been found in salivary glands of ticks and other hematophagous animals, such as leeches.[13-15]

Most salivary components have been identified through classical procedures where a given function was used to isolate an active molecule.[1] Using sequence similarities, transcriptome and proteomics analyses have also been used to identify arthropod saliva compounds.[16-19] For example, Ixolaris from *Ixodes scapularis* was initially identified by its sequence similarity to a tissue factor pathway inhibitor and has been found to have a potent anticoagulant activity in vitro[5] and antithrombotic effects in vivo.[20] Nevertheless, a large number of salivary gland transcript-encoded products have no similarity to proteins deposited in databases. Accordingly, annotation and functional assignment for these proteins has proven difficult.[1] For example, the family of 30-kDa salivary allergens found in different blood-sucking arthropods, including *Aedes* sp.,[17] *Culex* sp.,[19] and *Anopheles* sp.[16,18,21,22] While these proteins are major salivary components that display significant sequence similarity and many investigators have spent considerable effort, their function has remained elusive thus far.[16-19,21,22] In this disclosure, it is shown that Aegyptin is a specific ligand or binding partner for collagen.

For all of the above reasons, it is important to identify antithrombogenic molecules, which block platelet adhesion, activation and aggregation.

SUMMARY OF THE INVENTION

A new gene that encodes a novel protein containing an acidic N-terminal region and a basic C-terminal region has been discovered (see SEQ ID NOs: 1-2). This gene and the protein encoded therefrom is referred to as "Aegyptin".

Embodiments described herein include a purified or isolated nucleic acid encoding an Aegyptin-like polypeptide having an acidic N-terminal region and a basic C-terminal region. Nucleic acids encoding Aegyptins, Aegyptin polypeptides, and fragments of these molecules (e.g., fragments that are less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides or 20, 30, 40, 50, 60, 70, 80, 90, 100, 115, 130, 150, 175, 200, 225, 250, 270 or 273 consecutive amino acids) are also aspects of the invention. Some embodiments also include SEQ ID NO: 1 or SEQ ID NO: 3, a sequence complementary thereto, or a fragment thereof (e.g., fragments that are less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides).

Nucleic acids that hybridize to said nucleic acids having the nucleotide sequence selected from the group consisting of: SEQ ID NO: 1 or SEQ ID NO: 3 or fragments thereof (e.g., fragments that are less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides) under high stringency conditions (e.g., wash conditions with 1×SSC and 0.1% SDS at 60 degrees Centigrade) or medium stringency conditions (e.g., wash conditions with 1×SSC and 0.1% SDS at 50 degrees Centigrade) are also aspects of the invention. Still further, nucleic acids that share identity or homology to SEQ ID NO: 1 or SEQ ID NO: 3 or fragments thereof (e.g., fragments that are less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides) such as nucleic acids having greater than or equal to 40%, 50%, 60%, 70%, 80%, 90%, 95%, or 98% homology or identity to a nucleotide sequence selected from the group consisting of: SEQ ID NO: 1 or SEQ ID NO: 3 or fragments thereof (e.g., fragments that are less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides) are aspects of the invention.

In some embodiments, the Aegyptin nucleic acids (e.g. SEQ ID Nos. 1 or 3) are codon-optimized for expression in a recipient animal (e.g. human, horse, dog, cat, pig, chicken, or rodent). Other embodiments include Aegyptin-like purified or isolated polypeptides having an acidic N-terminal region and/or a basic C-terminal region. Aegyptins, Aegyptin polypeptides, and fragments of these molecules (e.g., fragments that are less than, greater than, or equal to 20, 30, 40, 50, 60, 70, 80, 90, 100, 115, 130, 150, 175, 200, 225, 250, 270 or 273 consecutive amino acids) are embodiments. Some embodied polypeptides also have the amino acid sequence of SEQ ID NO:2 and fragments thereof (e.g., fragments that are less than, greater than, or equal to 20, 30, 40, 50, 60, 70, 80, 90, 100, 115, 130, 150, 175, 200, 225, 250, 270 or 273 consecutive amino acids).

Antibodies to Aegyptins and fragments of Aegyptin-like polypeptides are also embodiments. These antibodies can be monoclonal or polyclonal. Antibodies capable of specifically binding to a protein comprising the amino acid sequence of SEQ ID NO:2 and fragments thereof or a fragment thereof (e.g., fragments that are less than, greater than, or equal to 10, 20, 30, 40, 50, 60, 70, 80, 90, 100, 115, 130, 150, 175, 200, 225, 250, 270 or 273 consecutive amino acids) are embodiments.

Methods of identifying a binding partner that interacts with Aegyptin are also embodiments. By one approach, a support comprising Aegyptin or a representative fragment thereof (e.g., fragments that are less than, greater than, or equal to 20, 30, 40, 50, 60, 70, 80, 90, 100, 115, 130, 150, 175, 200, 225, 250, 270 or 273 consecutive amino acids) is provided; the support is contacted with a candidate binding partner; and a biological complex comprising Aegyptin; and the candidate binding partner, is detected. The detection of such a complex indicates that said candidate binding partner interacts with Aegyptin. In certain aspects, the support is a microarray substrate, a bead, or a membrane.

Another way to identify an agent that modulates Aegyptin-mediated activity involves providing a support having an Aegyptin protein or a representative fragment thereof (e.g., fragments that are less than, greater than, or equal to 20, 30, 40, 50, 60, 70, 80, 90, 100, 115, 130, 150, 175, 200, 225, 250, 270 or 273 consecutive amino acids); contacting the support with a binding partner that binds to the Aegyptin protein or representative fragment thereof (e.g., fragments that are less than, greater than, or equal to 20, 30, 40, 50, 60, 70, 80, 90, 100, 115, 130, 150, 175, 200, 225, 250, 270 or 273 consecutive amino acids); contacting the support with a candidate agent; and detecting the presence or absence of an interaction of the binding partner to the Aegyptin protein and thereby identifying the agent as one that modulates Aegyptin-mediated activity. In certain aspects, the support can be, for example, a microarray substrate, a bead, a membrane and the like.

Also provided herein are methods of disrupting platelet adhesion in a subject by selecting or identifying a subject in need of a molecule that disrupts platelet adhesion and providing said subject with a therapeutically effective amount of an Aegyptin polypeptide or fragment thereof or a nucleic acid encoding said molecule (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids or a nucleic acid fragment that is less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides), or an antibody capable of specifically binding to an Aegyptin protein. Preferred Aegyptin nucleic acids for use in these methods include SEQ ID NO: 1 or SEQ ID NO: 3 or a fragment thereof (e.g., a nucleic acid fragment that is less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides) and preferred Aegyptin polypeptides for use in these methods include SEQ ID NO: 2 or a fragment thereof (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids). In certain embodiments, the animal is human. In certain embodiments, the Aegyptin polypeptide is SEQ ID NO: 2.

Also provided herein are methods of reducing clot formation comprising identifying a subject in need of a reduction in clot formation and providing to said subject a therapeutically effective amount of an Aegyptin or fragment thereof or nucleic acid encoding one or more of these molecules (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids or a nucleic acid fragment that is less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides), or an antibody capable of specifically binding to an Aegyptin protein. Preferred Aegyptin nucleic acids for use in these methods include SEQ ID NO: 1 or SEQ ID NO: 3 or a fragment thereof (e.g., a nucleic acid fragment that is less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides) and preferred Aegyptin polypeptides for use in these methods include SEQ ID NO: 2 or a fragment thereof (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids).

In certain embodiments, the Aegyptin polypeptide is Aegyptin (e.g. SEQ ID NO: 2) or fragments or mutants thereof. In certain embodiments, the method of reducing clot formation can be part of a treatment regimen in which an antithrombogenic compound is used. Nonlimiting examples include coronary thrombosis, pulmonary embolism, myocardial infarction, deep vein thrombosis, cerebral thrombosis, unstable angina, disseminated intravascular coagulation (DIC), postoperative fibrinolytic shutdown, or a rapid thrombogenic action, which can occur following implantation of a medical device. In some aspects of these embodiments, the reduction in clot formation is measured, monitored, or analyzed after contact with the Aegyptin polypeptide, fragment thereof or a nucleic acid encoding one or more of said molecules. Such measurements, monitoring, and analysis can be conducted by clinical examination by qualified medical personnel or by diagnostic approaches conventional in the field or as described herein.

Other embodiments include antithrombogenic medical devices. For example, medical devices, such as stents and catheters, which may include a therapeutically effective amount of an Aegyptin or fragment thereof or nucleic acid encoding one or more of these molecules (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids or a nucleic acid fragment that is less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides). Preferred Aegyptin nucleic acids for use in these methods include SEQ ID NO: 1 or SEQ ID NO: 3 or a fragment thereof (e.g., a nucleic acid fragment that is less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides) and preferred Aegyptin polypeptides for use in these methods include SEQ ID NO: 2 or a fragment thereof (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids).

Other embodiments include a vector comprising the purified or isolated nucleic acid encoding an Aegyptin or fragment thereof. (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids or a nucleic acid fragment that is less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides). Preferred Aegyptin nucleic acids for use in such vectors include SEQ ID NO: 1 or SEQ ID NO: 3 or a fragment thereof (e.g., a nucleic acid fragment that is less than, greater than, or equal to 20, 30, 40, 50, 60, 70, 80, 90, 100, or 125, 150, 175, 200, 250, 300, 345, 366, 400, 463, 500, 550, 600, 650, 700, 750, 800 or 822 consecutive nucleotides). In certain embodiments, a cultured cell comprises the vector.

Also provided herein are therapeutic anticoagulant formulations comprising an Aegyptin polypeptide or fragment thereof in combination with a pharmaceutically acceptable carrier. Preferred Aegyptin polypeptides for use in these methods include SEQ ID NO: 2 or a fragment thereof (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids). The therapeutic formulations can further comprise a second antithrombogenic agent, including any of heparin, hirudin, albumin, phospholipids, streptokinase, tissue plasminogen activator (tPA), urokinase (uPA), hydrophilic polymers such as hyaluronic acid, chitosan, methyl cellulose, poly(ethylene oxide), poly(vinyl pyrrolidone), growth factors such as endothelial cell growth factor, epithelial growth factor, osteoblast growth factor, fibroblast growth factor, platelet derived growth factor (PDGF), hepatocyte growth factor (HGF), or an angiogenic growth factor.

Also provided herein is a kit for determining Aegyptin protein expression which includes a probe indicative of Aegyptin protein expression in cells (e.g., an antibody that binds Aegyptin).

Other embodiments include a vaccine treatment, comprising an Aegyptin polypeptide (e.g., SEQ ID NO: 2) or fragment thereof in combination with a pharmaceutically acceptable carrier, or an Aegyptin nucleic acid (e.g., SEQ ID NOS:1 or 3) or a fragment thereof. Aegyptin nucleic acids or fragments thereof, as described herein, can be codon-optimized for expression in the animal that receives the vaccine or immunogeneic for mutations. Preferred Aegyptin polypeptides for use in these methods include SEQ ID NO: 2 or a fragment thereof (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids).

Other embodiments include use of an Aegyptin polypeptide or fragment thereof in the treatment of a thrombogenic disease. Preferred Aegyptin polypeptides for use in these methods include SEQ ID NO: 2 or a fragment thereof (e.g., an Aegyptin polypeptide fragment that is less than, greater than, or equal to 20, 30, 40, 50, 60, 70, 80, 90, 100, 115, 130, 150, 175, 200, 225, 250, 270 or 273 consecutive amino acids). Nonlimiting examples of thrombogenic disease include coronary thrombosis, pulmonary embolism, myocardial infarction, deep vein thrombosis, cerebral thrombosis, unstable angina, disseminated intravascular coagulation (DIC), postoperative fibrinolytic shutdown, or a rapid thrombogenic action which can occur following implantation of a medical device.

Other embodiments include a method of preventing metastasis comprising: identifying a subject in need of a molecule that prevents matastasis and providing the subject with a therapeutically effective amount the molecule, wherein the molecule is selected from the group consisting of: an Aegyptin polypeptide or fragment thereof, a nucleic acid encoding an Aegyptin polypeptide or fragment thereof, and an antibody capable of specifically binding to an Aegyptin protein. In certain aspects, the molecule is an Aegyptin polypeptide or fragment thereof. In certain aspects, the molecule is a nucleic acid encoding an Aegyptin polypeptide or fragment thereof. In certain aspects, the molecule is SEQ ID NO: 2 or a polypeptide encoded by SEQ ID NOs: 1 or 3 or a codon-optimized version thereof.

Also provided herein is a method of treating or inhibiting progression of a malignant tumor in a subject comprising: identifying a subject in need of a molecule that treats or inhibits progression of a malignant tumor and providing the animal with a therapeutically effective amount the molecule, wherein the molecule is selected from the group consisting of: an Aegyptin polypeptide or fragment thereof, a nucleic acid encoding an Aegyptin polypeptide or fragment thereof, and an antibody capable of specifically binding to an Ixostatin protein. In certain aspects, the molecule is an Aegyptin polypeptide or fragment thereof. In certain aspects, the molecule is a nucleic acid encoding an Aegyptin polypeptide or fragment thereof. In certain aspects, the molecule is SEQ ID NO: 2 or a polypeptide encoded by SEQ ID NOs: 1 or 3 or a codon-optimized version thereof. In certain aspects, the molecule is an antibody capable of specifically binding to an Aegyptin protein. In certain aspects, the animal is human.

Also provided herein is a purified or isolated nucleic acid encoding an Aegyptin polypeptide or fragment thereof. In certain aspects, the nucleic acid encodes a polypeptide comprising SEQ ID NO: 22.

Also provided herein is a purified or isolated Aegyptin polypeptide comprising Aegyptin or a fragment thereof. In certain aspects, the polypeptide comprises SEQ ID NO: 22.

BRIEF DESCRIPTION OF THE DRAWINGS

FIG. 1A shows a schematic representation of Aegyptin with typical acidic N-terminus, (GEEDA, SEQ ID NO: 7) repeats, and basic carboxyterminal depicted. FIG. 1B shows purification of recombinant Aegyptin after $Ni^{2+}$ agarose and gel-filtration columns. The inset shows NU-PAGE of purified Aegyptin under denaturating conditions. FIG. 1C shows the results of plasmon resonance experiments that demonstrate that Aegyptin interacts with collagen (I-III) but not with vitronectin, laminin, fibronectin, vWf, and fibrinogen. FIG. 1D shows gel filtration of salivary gland homogenate (solid line) and identification of the active fraction that binds to collagen (large circles). The elution pattern of recombinant Aegyptin is superimposed (small circles). FIG. 1E shows anion-exchange chromatography of the active fraction obtained in (D) and identification of collagen-binding activity (large circles). The elution pattern of recombinant Aegyptin is superimposed (small circles). The inset shows Western blot analysis for detection of Aegyptin in the salivary gland using polyclonal anti-Aegyptin antibodies.

FIG. 2A shows that Aegyptin inhibits collagen-induced platelet aggregation, but does not inhibit platelet aggregation induced by other agonists ADP, PMA, ristocetin, araquidonic acid, U46619, convulxin, TRAP and thrombin. Light transmittance is shown as a function of time. Assay results from control (a), 30 nM (b), 60 nM (c), and 120 nM (d) Aegyptin are shown. FIG. 2B shows dose-response inhibition of collagen-induced platelet aggregation and ATP release by aegyptin. The tracings represent a typical experiment (n=6).

FIG. 3C shows that *Ae. aegypti* saliva interacts with immobilized collagen type I (a) and III (b). Sensorgrams are representative of triplicate experiments.

FIG. 4A shows results when collagen type I was injected at different concentrations (in µg/ml: a, 50; b, 25, c, 12.5; d, 6.25; and e, 3.175) over immobilized GPVI. FIG. 4B shows results when collagen type I was incubated with buffer (sensorgram a) or 500 nM Aegyptin (sensorgrams c-g) at the following conentrations (in µg/ml: a and c, 50; d, 25, e, 12.5; f, 6.25; and g, 3.175). The mixtures were injected over immobilized GPVI. Sensorgram b shows that Aegyptin at 500 nM does not bind to immobilized GPVI. FIG. 4C shows results when convulxin was injected at different concentrations (a, 10 nM; b, 5 nM and c, 2.5 nM) over immobilized GPVI. FIG. 4D shows results when convulxin (a, 10 nM; b, 5 nM and c, 2.5 nM) was saturated with 500 nM of Aegyptin and the mixture injected over immobilized GPVI (n=3).

FIGS. 5B and 5D are dose-responses curves for aegyptin-mediated inhibition of platelet adhesion to fibrillar or soluble collagen, respectively (n=3).

FIG. 6A is a graph showing inhibition of vWf binding to soluble collagen III as demonstrated by ELISA in the presence of indicated concentrations of aegyptin. FIG. 6B is a series of photomicrographs showing platelet adhesion when anticoagulated whole blood was perfused over immobilized fibrillar collagen for 180 seconds at a shear rate of 1500 $s^{-1}$ in the presence of a, 0; b, 0.1; c, 0.3; and d, 1 µM of aegyptin. FIG. 6C is a graph showing a dose-response curve for aegyptin-mediated inhibition of platelet adhesion to collagen under flow conditions (n=3).

FIGS. 8A-8E show biochemical and biophysical aspects of Aegyptin. (A) Chromatographic analysis of Aegyptin by size exclusion (apparent molecular weight 110 kDa) is superimposed to the elution pattern of molecular weight markers. (B) Inline multi-angle light scatter (MALS). The solid trace represents absorbance 280 nm and the dashed line represents MALS results, respectively. Molecular weight standards used: thyroglobulin (670 kDa), immunoglobulin (158 kDa), ovalbumin (44 kDa), myoglobin (17 kDa) and vitamin B12 (1.35 kDa). (C) CD spectra of Aegyptin (inset shows the proportion of α-helix, β-sheet, β-turn and unordered structures). (D) Predictor Of Naturally Disordered Regions (PONDR) score indicates that Aegyptin belongs to the family of naturally disordered proteins, with its C-terminus domain well organized (E) Predicted tertiary structure of Aegyptin using the Phyre software shows that Aegyptin might display an extended or elongated pattern as indicated by multi-angle light scatter traces.

FIGS. 10A-10H show Aegyptin binds to sequences that mediate collagen interaction with physiological ligands GPVI, integrin α2β1 and vWF and recognizes heat-denatured collagen. Sensorgrams shows Aegyptin binding to immobilized (A) $(GPO)_{10}$ (SEQ ID NO: 10), (C) GFOGER (SEQ ID NO: 8), (E) RGQOGVMGFO (SEQ ID NO: 9) cross-linked peptides or (G) heat-denatured collagen (90 min at 98° C.). Different concentrations of recombinant Aegyptin for (A) and (C) were (in µM: a, 3; b, 2; c, 1; d, 0.5; e, 0.3; f, 0.15 and g, 0.15); for (E) was (in nM: a, 500; b, 250; c, 125; d, 60; e, 15; f, 5); for (G) was (in nM: a, 150; b, 75; c, 37.5; d, 18.75; e, 9.3; f, 4.6 and g, 2.3) and injected over immobilized ligands for 180 seconds. Dissociation of Aegyptin-ligand complex was monitored for 1800 seconds, and a global two-state binding model was used to calculate kinetic parameters. Sensorgrams are representative of triplicate experiments. (B) Functional assay using human platelet-rich plasma shows that Aegyptin is ineffective to inhibit platelet responses to $(GPO)_{10}$ (CRP, 2.5 µg/ml) but prevents collagen (2 µg/ml)-induced platelet aggregation. (D) Aegyptin failed to prevent washed human platelet adhesion to GFOGER (SEQ ID NO: 8) under static conditions, but effectively inhibits platelet adhesion to collagen. No adhesion was detectable in the presence of EDTA. (F) Inhibition of vWF binding to RGQOGVMGFO (SEQ ID NO: 9) was estimated by ELISA in the presence of indicated concentrations of Aegyptin (n=3). (H) Binding of Aegyptin-FITC to fibrillar collagen. Cover slips coated with fibrillar collagen were incubated with Aegyptin-FITC for 20 min at room temperature and analyzed under fluorescence microscope, as described in Methods. Collagen did not display any auto fluorescence under the conditions used.

DETAILED DESCRIPTION OF THE INVENTION

Figures 1A, 1B, 1C:
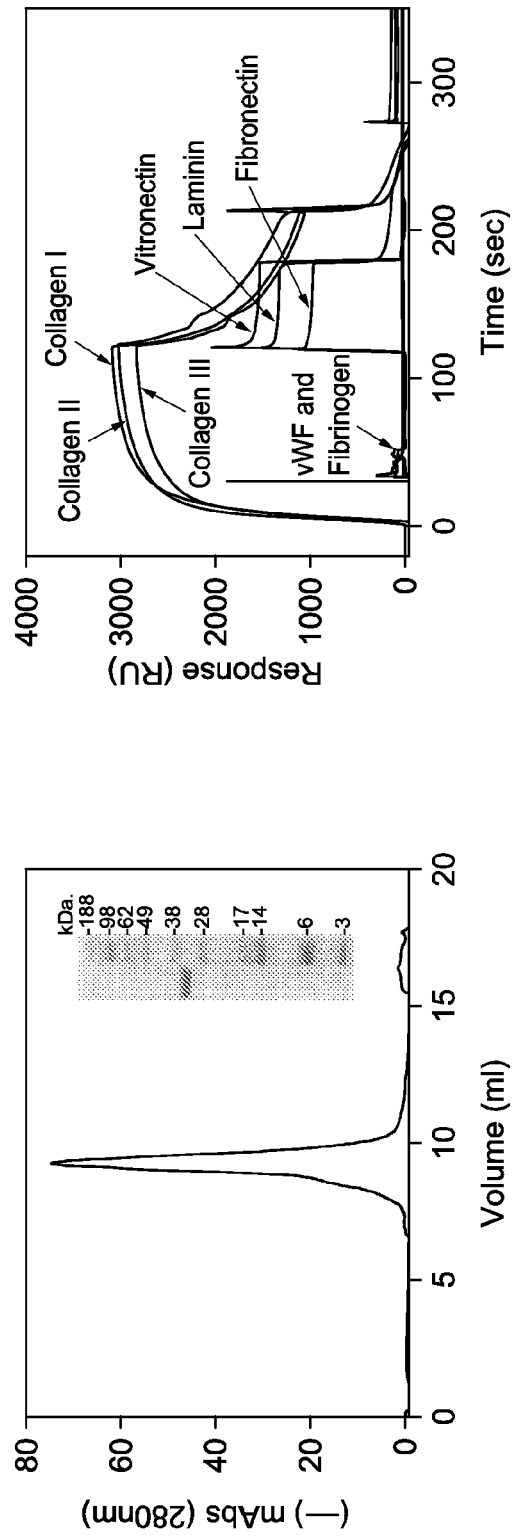
FIGS. 1A-E show the molecular characterization of Aegyptin and identification in the *Ae. aegypti* salivary gland.

A new family of structurally distinctive proteins, identified by their acidic N-terminal region and basic C-terminal region "Aegyptins", has been discovered. One member of this family have been identified, cloned, sequenced, and characterized. Aegyptin binds to collagens (I-V), and interferes with its interaction with major physiological ligands: GPVI, integrin α2β1, and vWf. Notably, Aegyptin blocks GPVI interaction with collagen and inhibits platelet aggregation and adhesion.

Collagen is a matrix protein that plays a pivotal role in the process of primary hemostasis: at sites of vascular injury, it initiates recruitment of circulating platelets and triggers platelet activation cascade required to stimulate thrombus growth.[23-25] The first step in platelet recruitment to collagen occurs indirectly via binding of platelet glycoprotein (GP) Ib to collagen-bound von Willebrand factor (vWf), which plays a critical role in tethering of platelets at high shear levels.[26,27] The rapid off-rate of GPIb-vWf interactions results in platelet translocation at the site of injury, allowing adhesive interactions with slower binding kinetics—such as the platelet collagen receptors glycoprotein VI (GPVI) and $α_2β_1$ integrins—to mediate platelet adhesion and activation.[23-28] The relative contributions of these two receptors to collagen-mediated platelet responses are under intense investigation,[28-34] and different models have been proposed in an attempt to explain how platelets are activated by collagen.[23,28,35]

Collagen is a triple helical protein that constitutes the major structural component of the extracellular matrix (ECM). Damage to the blood vessel endothelium results in the exposure of fibrilar collagen I and III, both abundant in the subendothelial space. Interaction of circulating platelets with collagen is a multistage process involving several receptors and the relative contribution of each of them has been intensely investigated. Accordingly, the initial tethering of platelet to the ECM is mediated by the interaction of platelet receptor glycoprotein (GP) Ib and von Willebrand Factor (vWF)-bound collagen, particularly at high shear rates. This interaction allows the binding of the collagen receptor GPVI to its ligand and to initiate cellular activation, a process that is reinforced by locally produced thrombin and soluble mediators released from platelets. These events lead to the shift of beta integrins on the platelet surface from a low to a high affinity state, thereby enabling them to bind their ligands and to mediate firm adhesion, spreading, coagulant activity, and aggregation.

A number of successful strategies targeting platelets activation have been tested experimentally and therapeutically in humans and shown to affect thrombus formation in vivo (Davi, G., and Patrono, C. 2007 *N Engl J Med* 357:2482-2494). Among these drugs, aspirin is well known to prevent thrombus formation by a mechanism that is mediated by inhibition of cyclooxygenase. More recently, ADP receptor antagonists were shown to effectively prevent platelet aggregation according to a number of clinical trials (Wiviott, S. D., et al. 2007 *N Engl J Med* 357:2001-2015). Additionally, molecules such as epitifibatide (Integrilin), which were designed based on integrin $α_{IIb}β_3$ antagonists from snake venoms (Fox, J. W., and Serrano, S. M. *Curr Pharm Des* 13:2927-2934) are currently approved for the treatment of cardiovascular diseases. Notably, exogenous secretion from snake venom and blood sucking invertebrates such as mosquitoes, ticks, and leeches are rich sources of modulators of hemostasis and the immune system (Fox, J. W., and Serrano, S. M. 2007 *Curr Pharm Des* 13:2927-2934; Ribeiro, J. M., and Francischetti, I. M. 2003 *Annu Rev Entomol* 48:73-88; Maritz-Olivier, C., et al. 2007 *Trends Parasitol* 23:397-407). Recently it was shown that *Aedes aegypti* salivary gland expresses Aegyptin, a potent collagen binding protein that prevents its interaction with three major ligands, namely, GPVI, vWF and integrin α2β1 (Calvo, E., et al. 2007 *J Biol Chem* 282:26928-26938). Aegyptin displays sequence and functional similarities to AAPP, a collagen-binding protein from the salivary gland of *Anopheles stephensi* (Yoshida, S., et al. 2008 *Blood* 111: 2007-2014). The aim of this study was to understand the molecular mechanism by which Aegyptin prevents platelet aggregation, and also to investigate its potential antithrombotic properties in vivo. It was found that Aegyptin inhibits platelet activation by a novel and unusual mechanism: recognition of specific binding sequences involved in collagen interaction with major physiological ligands, and unwinding of the triple helical molecule.

Aegyptin is a 30 kDa mosquito salivary protein which displays GEEDA (SEQ ID NO: 7) repeats and specifically binds to collagen I-V. Aegyptin has unique biophysical properties and the molecular mechanism by which it inhibits platelet activation is identified. Light scattering plot shows that Aegyptin displays a monomeric elongated form which explains the apparent molecular weight of 110 kDa estimated by gel-filtration chromatography. Atomic force microscopy reveals that collagen exposed to Aegyptin is accompanied by global unwinding of the rope-like structure of the triple helix without cleavage, and circular dicroism confirms that collagen undergoes a dramatic structural change upon binding to Aegyptin as estimated by a decrease in ellipiticity. In addition, surface plasmon resonance shows that Aegyptin binds to peptide sequences which mediate collagen interaction with GPVI $(GPO)_{10}$ (SEQ ID NO: 10), integrin $α_2β_1$ (GFOGER, SEQ ID NO: 8) and particularly with von Willebrand Factor (RGQOGVMGFO, SEQ ID NO: 9). Aegyptin also binds with high affinity to heat-denatured collagen suggesting that the inhibitor recognizes primary sequences of collagen molecule that results in a tight interaction. Truncated forms of Aegyptin were engineered, and a peptide containing the C-terminus domain devoid of GEEDA (SEQ ID NO: 7) repeats was shown to interact with collagen and to attenuate platelet aggregation. Notably, Aegyptin prevents laser-induced carotid thrombus formation in the presence of Rose Bengal in vivo, without observable bleeding in rats. Aegyptin is a potentially useful molecule to develop specific inhibitors of collagen-mediated pathological processes.

Several embodiments of the invention have biotechnological, diagnostic, and therapeutic use. For example, the nucleic acids of the invention and/or proteins of the invention can be used as probes to isolate more Aegyptins, detect the presence of wild type or mutant Aegyptins in various tissues, and can be incorporated into constructs for preparing recombinant Aegyptin proteins or can be expressed from such constructs. The sequences of the nucleic acids of the invention and/or proteins of the invention can also be incorporated into computer systems, used with modeling software so as to enable some forms of rational drug design. The nucleic acids of the invention and/or proteins of the invention, as well as, the binding partners of the invention, can be incorporated into pharmaceuticals and used for the treatment of platelet adhesion, activation and aggregation, and other thrombosis-related disorders.

The nucleic acid embodiments of the invention include nucleotides encoding Aegyptin molecules and fragments thereof and variants such as spliced variants, allelic variants, synonomous sequences, and homologous or orthologous molecules. Some embodiments for example, include genomic DNA, RNA, and cDNA encoding Aegyptins. The nucleic acid embodiments of the invention also include partial or complete DNA sequences shown in the sequence listing (SEQ ID NOS: 1 and 3), nucleotide sequences encoding the amino acid sequence shown in the sequence listing (SEQ ID NO: 2) and complements thereof. Nucleic acid sequences encoding Aegyptins from other organisms are also embodiments, as are methods for obtaining such sequences. The nucleic acid embodiments can be altered, mutated, or changed such that the alteration, mutation, or change results in a conservative amino acid replacement. Aegyptin nucleic acids can be codon-optimized for expression in a suitable host using conventional software and DNA systems technologies. Suitable hosts include humans, horses, dogs, cats, pigs, chickens, and rodents. The nucleic acid embodiments can also be altered, mutated, or changed such that the alteration, mutation, or change results in a non-conservative amino acid replacement. Some embodiments of the invention, for example, include nucleic acids encoding Aegyptin molecules that have one or more of the Aegyptin domains deleted or combined in a novel fashion so as to create an "Aegyptin-like hybrid" molecule. Further, some embodiments relate to nucleic acids encoding Aegyptin-like hybrids having multimerized domains, synthetic domains, and domains from other proteins.

Some polypeptide embodiments include a partial or complete amino acid sequence shown in the sequence listing (SEQ ID NO: 2) and functional equivalents to such molecules including, but not limited to, the polypeptides of SEQ ID NO: 2 having non-conservative amino acid substitutions and peptidomimetics that resemble these molecules. Additional polypeptide embodiments include mutant Aegyptins having nonconservative amino acid replacements, in particular mutants that result in gain or loss of Aegyptin function. Further, the polypeptide embodiments include Aegyptin-like hybrids having one or more of the Aegyptin domains deleted or combined in a novel fashion or multimerized domains, synthetic domains, and domains from other proteins. Polypeptides that are homologous to Aegyptin are also embodiments and methods of obtaining such molecules are provided. Additionally, methods of preparing the polypeptide embodiments by chemical synthesis and recombinant techniques are disclosed. Approaches to creating genetically altered organisms that express either a wild-type or mutant Aegyptin transgene (i.e. Aegyptin transgenic or knockout animals) are also provided.

Several embodiments also include antibodies that recognize wild-type and mutant Aegyptins. Approaches to manufacture monoclonal and polyclonal antibodies are disclosed.

Approaches to rational drug design are also provided, and these methods can be used to isolate new Aegyptin family members and to identify molecules that interact with the Aegyptins, referred to as "binding partners". Several computer-based methodologies are discussed, which involve three-dimensional modeling of the Aegyptin nucleic acid and/or protein sequences and the nucleic acid and protein sequences encoding known or suspected binding partners (e.g., antibodies and collagen).

Aegyptin characterization assays are also described. These assays test the functionality of an Aegyptin molecule and identify binding partners that interact with the Aegyptins. Some functional assays involve the use of multimeric Aegyptins and/or binding partners, which are Aegyptins, hybrids, or binding partners disposed on a support, such as a resin, bead, lipid vesicle or cell membrane. These multimeric agents are contacted with candidate binding partners and the association of the binding partner with the multimeric agent is determined. Successful binding agents can be further analyzed for their effect on Aegyptin function by using cell based assays. One such assay evaluates the effect of Aegyptins, hybrids, and binding partners on the activation of mitogen activated kinase, RAS, or the phosphorylation of myelin basic protein. Other Aegyptin characterization assays involve molecular biology techniques designed to identify protein-protein interactions (e.g., two-hybrid systems).

Several pharmaceutical embodiments described herein include medicaments that contain Aegyptins, Aegyptin-like hybrids, and binding partners, which interact with Aegyptins. These medicaments can be prepared in accordance with conventional methods of galenic pharmacy for administration to organisms in need of treatment. A therapeutically effective amount of an Aegyptin molecule, Aegyptin-like hybrid molecule, or a binding partner of Aegyptin can be incorporated into a pharmaceutical composition with or without a carrier. Routes of administration of the pharmaceuticals of the invention include, but are not limited to, topical, intranasal, transdermal, parenteral, gastrointestinal, transbronchial, and transalveolar. Electroporation of Aegyptin nucleic acids (e.g., SEQ ID NOS: 1 and 3) or fragments thereof, as described herein, is also contemplated (e.g., Medpulsar®). These pharmaceuticals can be provided to organisms in need of treatment for platelet adhesion, activation and aggregation, and other thrombosis-related disorders. The section below describes several of the nucleic acid embodiments of the invention.

Nucleic Acids Encoding Aegyptins and Aegyptin-Like Hybrids

A new family of structurally distinctive molecules, designated Aegyptins, has been discovered. These molecules can be identified by their acidic N-terminal region and basic C-terminal region. Several nucleic acid embodiments described herein include nucleotides encoding Aegyptin molecules and fragments thereof and variants, such as spliced variants, allelic variants, synonomous sequences, and homologous or orthologous molecules. Some embodiments for example, include genomic DNA, RNA, and cDNA encoding Aegyptins. Aegyptins can be present in many different organisms including but not limited to plants, insects, animals, and mammals. Further, molecules that resemble Aegyptins by the organization of their structure (e.g., a molecule having an acidic N-terminal region and a basic C-terminal region) and hybrid molecules having one or more of the aforementioned domains are embodiments of the invention.

The discovery of Aegyptin was made while examining sequences of clones generated from a cDNA library from *Ae. aegypti* (mosquito) saliva. (See Example 1). The coding sequence of Aegyptin cDNA and Aegyptin protein are provided in the Sequence Listing (SEQ ID NOS. 1 and 2), respectively.

Data presented, infra, demonstrate that: Aegyptin is a low molecular weight, approximately 30 kDa protein (Example 2). In addition, Aegyptin displays remarkably tight interaction to collagen types I and III (Example 5). It was also found that Aegyptin prevents collagen-induced platelet aggregation (Example 4) and can inhibit platelet adhesion to collagen (Examples 8-10).

The Aegyptin nucleotide sequences also include: (a) the DNA sequences shown in the sequence listing (SEQ ID NOS: 1 and 3); (b) nucleotide sequences encoding the amino acid sequences shown in the sequence listing (SEQ ID NO: 2); (c) any nucleotide sequence that hybridizes to the complement of the DNA sequences shown in the sequence listing (SEQ ID NOS: 1 and 3) under stringent conditions, e.g., hybridization to filter-bound DNA in 0.5 M $NaHPO_4$, 7.0% sodium dodecyl sulfate (SDS), 1 mM EDTA at 50° C. and washing in 0.2× SSC/0.2% SDS at 50° C.; and (d) any nucleotide sequence that hybridizes to the complement of the DNA sequences that encode an amino acid sequence provided in the sequence listing (SEQ ID NO: 2) under less stringent conditions (e.g., hybridization in 0.5 M $NaHPO_4$, 7.0% sodium dodecyl sulfate (SDS), 1 mM EDTA at 37° C. and washing in 0.2×SSC/0.2% SDS at 37° C.

Embodiments also include Aegyptins that are isolated from other organisms (e.g., plants, molds, yeast, insects, animals, and mammals) and mutant Aegyptins, whether naturally occurring or engineered. Approaches to isolate Aegyptin homologs in other species are provided infra. Embodiments also include fragments, modifications, derivatives, and variants of the sequences described above. Desired embodiments, for example, include nucleic acids having at least 9 consecutive nucleotides of an Aegyptin or a sequence complementary thereto and preferred fragments of the invention include at least 9 consecutive nucleotides of Aegyptin or a sequence complementary thereto. In this regard, the nucleic acid embodiments of the invention can have from 9 to approximately 822 consecutive nucleotides for Aegyptin. Some DNA fragments of the invention, for example, comprise, consist, or consist essentially of a nucleic acid with less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 550, 600, 650, 700, 750, 800 and 822 consecutive nucleotides of an Aegyptin gene (e.g., a sequence of SEQ ID NOS: 1 and 3 or a complement thereof). Preferably, the nucleic acid embodiments, however, comprise at least 12, 13, 14, 15, 16, 17, 18, or 19 consecutive nucleotides of a sequence of SEQ ID NOS: 1 and 3 or complement thereof. More preferably, the nucleic acid embodiments comprise at least 20-30 consecutive nucleotides or complement thereof.

The nucleic acid embodiments can also be altered by mutation such as substitutions, additions, or deletions that provide for sequences encoding functionally equivalent molecules. Due to the degeneracy of nucleotide coding sequences, other DNA sequences that encode substantially the same Aegyptin amino acid sequence as depicted in SEQ ID NO: 2 can be used in some embodiments of the present invention. These include, but are not limited to, nucleic acid sequences comprising all or portions of Aegyptin or nucleic acids that complement all or part of Aegyptin that have been altered by the substitution of different codons that encode a functionally equivalent amino acid residue within the sequence, thus producing a silent change, or a functionally non-equivalent amino acid residue within the sequence, thus producing a detectable change.

The mutant Aegyptin nucleic acids also include nucleic acids encoding Aegyptin polypeptides or peptides having a non-conservative change that affects the functionality of the molecule (e.g. modulates platelet adhesion, activation and aggregation). Additional mutant Aegyptins include nucleic acids encoding molecules in the Aegyptin acidic N-terminal region or basic C-terminal region domain is deleted. Further, some Aegyptin mutant nucleic acids encode one or more Aegyptin domains combined in a novel fashion so as to create an "Aegyptin-like hybrid" molecule, also referred to as a "hybrid". These hybrids can be used to modulate (i.e., inhibit or enhance) platelet adhesion, activation and aggregation, for example. Some nucleic acids also encode multimerized Aegyptins or hybrids, which are characterized by a structure having at least two of the same domain (e.g., a hybrid having two acidic regions or two basic regions). Several assays can be employed to evaluate these molecules for their ability to modulate platelet adhesion, activation and aggregation, and many are discussed in detail infra. The Aegyptin-like hybrids that are identified for their ability to modulate platelet adhesion, activation and aggregation can be used in biotechnological assays and can be formulated in pharmaceuticals for the treatment of diseases and abnormalities in various organisms.

The nucleotide sequences encoding the full-length Aegyptin protein, or fragments thereof can be modified to generate sequences optimized for expression in human cells without altering the encoded polypeptide sequences. Computer algorithms are available for codon optimization. For example, web-based algorithms (e.g., Sharp et al. (1988) Nucleic Acids Res. 16:8207-11, hereby incorporated by reference) can be used to generate a nucleotide sequence with optimized expression in a suitable host (e.g., human, horse, dog, cat, pig, chicken or rodent).

Some mutant Aegyptin nucleic acid embodiments include nucleic acids encoding Aegyptin-like hybrids, wherein one or more regions of the protein are swapped with synthetic polypeptides. For example, nucleic acids encoding the Aegyptin acidic region or basic region can be joined to a nucleic acid encoding a synthetic hydrophobic domain (e.g., poly-leucine) so as to create a reagent that better associates with a membrane. Similarly, the nucleic acids encoding the various domains of Aegyptin can be swapped with nucleic acids encoding domains from other proteins (besides Aegyptins) involved in platelet adhesion, activation and aggregation. In this manner, many different nucleic acids encoding designer peptides can be created and these molecules can be used to modulate specific cellular events, for example. The nucleic acid sequences described above also have biotechnological and diagnostic use, e.g., in nucleic acid hybridization assays, Southern and Northern Blot analysis, etc.

By using the Aegyptin nucleic acid sequences disclosed herein (e.g., SEQ ID NOS: 1 and 3), probes that complement Aegyptin can be designed and manufactured by oligonucleotide synthesis. Desirable probes comprise a nucleic acid sequence of (SEQ ID NOS: 1 and 3) that is unique to Aegyptins with preferred probes comprising a nucleic acid fragment of (SEQ ID NOS: 1 and 3) that is unique to Aegyptin. These probes can be used to screen cDNA or genomic libraries from various organisms (e.g., plants, molds, fungi, yeast, insects, animals, and mammals) so as to isolate natural sources of the nucleic acid embodiments described herein. Screening can be by filter hybridization, for example, using duplicate filters. The labeled probe preferably contains at least 15-30 base pairs of a nucleic acid sequence of (SEQ ID NOS: 1 and 3) that are unique to Aegyptin. The hybridization washing conditions used are preferably of a lower stringency when the cDNA library is derived from an organism different from the type of organism from which the labeled sequence is originated.

With respect to the cloning of an Aegyptin homolog, using murine Aegyptin probes, for example, hybridization can be performed in 0.5M $NaHPO_4$, 7.0% sodium dodecyl sulfate (SDS), 1 mM EDTA at 37° C. overnight and washing can be performed in 0.2×SSC/0.2% SDS at 37° C. Various stringency conditions are well known to those of skill in the art, and will vary predictably depending on the specific organisms from which the library and the labeled sequences are derived. For guidance regarding such conditions see, for example, Sambrook et al., 1989, *Molecular Cloning, A Laboratory Manual*, Cold Springs Harbor Press, N.Y.; and Ausubel et al., 1989, *Current Protocols in Molecular Biology*, Green Publishing Associates and Wiley Interscience, N.Y.

Further, sequences from nucleic acids complementing Aegyptin, or portions thereof, can be used to make oligonucleotide primers by conventional oligonucleotide synthesis for use in isolation and diagnostic procedures that employ the Polymerase Chain Reaction (PCR) or other enzyme-mediated nucleic acid amplification techniques. An Aegyptin gene homolog can be isolated from a nucleic acid of the organism of interest by performing PCR using two degenerate oligonucleotide primer pools designed on the basis of amino acid sequences within the Aegyptin gene products disclosed herein. The template for the reaction can be cDNA obtained by reverse transcription of mRNA prepared from, for example, cells or tissue of an organism known or believed to express an Aegyptin. A variety of PCR techniques are familiar to those skilled in the art. For a review of PCR technology, see Molecular Cloning to Genetic Engineering White, B. A. Ed. in *Methods in Molecular Biology* 67: Humana Press, Totowa (1997), the disclosure of which is incorporated herein by reference in its entirety and the publication entitled "PCR Methods and Applications" (1991, Cold Spring Harbor Laboratory Press), the disclosure of which is incorporated herein by reference in its entirety.

For amplification of mRNAs, it is within the scope of the invention to reverse transcribe mRNA into cDNA followed by PCR (RT-PCR); or, to use a single enzyme for both steps as described in U.S. Pat. No. 5,322,770, the disclosure of which is incorporated herein by reference in its entirety. Another technique involves the use of Reverse Transcriptase Asymmetric Gap Ligase Chain Reaction (RT-AGLCR), as described by Marshall R. L. et al. (*PCR Methods and Applications* 4:80-84, 1994), the disclosure of which is incorporated herein by reference in its entirety. Briefly, RNA is isolated, following standard procedures, from an appropriate cellular or tissue source. A reverse transcription reaction is performed on the RNA using an oligonucleotide primer specific for the most 5' end of the amplified fragment as a primer of first strand synthesis. The resulting RNA/DNA hybrid is then "tailed" with guanines using a standard terminal transferase reaction. The hybrid is then digested with RNAse H, and second strand synthesis is primed with a poly-C primer. Thus, cDNA sequences upstream of the amplified fragment are easily isolated. For a review of cloning strategies which can be used, see e.g., Sambrook et al., 1989, supra.

In each of these amplification procedures, primers on either side of the sequence to be amplified are added to a suitably prepared nucleic acid sample along with dNTPs and a thermostable polymerase, such as Taq polymerase, Pfu polymerase, or Vent polymerase. The nucleic acid in the sample is denatured and the primers are specifically hybridized to complementary nucleic acid sequences in the sample. The hybridized primers are then extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188, the disclosure of which is incorporated herein by reference in their entirety.

The primers are selected to be substantially complementary to a portion of the nucleic acid sequence of (SEQ ID NOS: 1 and 3) that is unique to Aegyptin, thereby allowing the sequences between the primers to be amplified. Preferably, primers are 16, 17, 18, 19, 20, 21, 22, 23, 24, 25, 26, 27, 28, 29 and 30 nucleotides in length. The formation of stable hybrids depends on the melting temperature (Tm) of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers of the present invention preferably ranges between 10 and 75%, more preferably between 35 and 60%, and most preferably between 40 and 55%. The appropriate length for primers under a particular set of assay conditions can be empirically determined by one of skill in the art.

The spacing of the primers relates to the length of the segment to be amplified. In the context of the present invention, amplified segments carrying nucleic acid sequence encoding fragments of Aegyptin can range in size from at least about 25 bp to 35 kb. Amplification fragments from 25-1000 bp are typical, fragments from 50-1000 bp are preferred and fragments from 100-600 bp are highly preferred. It will be appreciated that amplification primers can be of any sequence that allows for specific amplification of a region of an Aegyptin and can, for example, include modifications such as restriction sites to facilitate cloning.

The PCR product can be subcloned and sequenced to ensure that the amplified sequences represent the sequences of an Aegyptin gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library. The identification and characterization of genomic clones from many different organisms (particularly humans) is helpful for designing diagnostic tests and clinical protocols for treating and preventing aberrations or diseases involving defects in platelet adhesion, activation and aggregation, and other thrombosis-related disorders. For example, sequences derived from regions adjacent to the intron/exon boundaries of human Aegyptin genes can be used to design primers for use in amplification assays to detect mutations within the exons, introns, splice sites (e.g. splice acceptor and/or donor sites), etc., that can be used in diagnostics.

The Aegyptin gene sequences can additionally be used to isolate mutant Aegyptin gene alleles. Such mutant alleles can be isolated from organisms either known or proposed to have a genotype that contributes to a disorder involving aberrant platelet adhesion, activation and aggregation. Mutant alleles and mutant allele products can then be utilized in the therapeutic and diagnostic systems described below. Additionally, such Aegyptin gene sequences can be used to detect Aegyptin gene regulatory (e.g., promoter or promotor/enhancer) defects that can affect platelet adhesion, activation and aggregation.

A cDNA of a mutant Aegyptin gene can be isolated, for example, by using PCR. In this case, the first cDNA strand can be synthesized by hybridizing an oligo-dT oligonucleotide to mRNA isolated from tissue known or suspected to be expressed in an individual putatively carrying the mutant Aegyptin allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and organised to DNA sequence analysis through methods well known to those of skill in the art. By comparing the DNA sequence of the mutant Aegyptin allele to that of the normal Aegyptin allele, the mutation(s) responsible for the loss or alteration of function of the mutant Aegyptin gene product can be ascertained.

Alternatively, a genomic library can be constructed using DNA obtained from an organism suspected of or known to carry the mutant Aegyptin allele, or a cDNA library can be constructed using RNA from a tissue known, or suspected, to express the mutant Aegyptin allele. The normal Aegyptin gene or any suitable fragment thereof can then be labeled and used as a probe to identify the corresponding mutant Aegyptin allele in such libraries. Clones containing the mutant Aegyptin gene sequences can then be purified and subjected to sequence analysis according to methods well known to those of skill in the art.

Additionally, an expression library can be constructed utilizing cDNA synthesized from, for example, RNA isolated from a tissue known, or suspected, to express a mutant Aegyptin allele in an organism suspected of, or known to carry, such a mutant allele. In this manner, gene products made by the putatively mutant tissue can be expressed and screened using standard antibody screening techniques in conjunction with antibodies raised against the normal Aegyptin gene product. (For screening techniques, see, for example, Harlow, E. and Lane, eds., 1988, *Antibodies: A Laboratory Manual*, Cold Spring Harbor Press, Cold Spring Harbor.) By using conventional antibody screening techniques and the anti-Aegyptin antibody described in Example 4, one can isolate Aegyptin from expression libraries of various organisms. In cases where an Aegyptin mutation results in an expressed gene product with altered function (e.g., as a result of a missense or a frameshift mutation), a polyclonal set of antibodies against Aegyptin are likely to cross-react with the mutant Aegyptin gene product. Library clones detected via their reaction with such labeled antibodies can be purified and subjected to sequence analysis according to methods well known to those of skill in the art.

The invention also encompasses (a) DNA vectors that contain any of the foregoing Aegyptin coding sequences and/or their complements (i.e., antisense or RNAi vectors); (b) DNA expression vectors that contain any of the foregoing Aegyptin coding sequences operatively associated with a regulatory element that directs the expression of the coding sequences; and (c) genetically engineered host cells that contain any of the foregoing Aegyptin coding sequences operatively associated with a regulatory element that directs the expression of the coding sequences in the host cell. These recombinant constructs are capable of replicating autonomously in a host cell. Alternatively, the recombinant constructs can become integrated into the chromosomal DNA of a host cell. Such recombinant polynucleotides typically comprise an Aegyptin genomic or cDNA polynucleotide of semi-synthetic or synthetic origin by virtue of human manipulation. Therefore, recombinant nucleic acids comprising Aegyptin sequences and complements thereof that are not naturally occurring are provided by embodiments of this invention.

Although nucleic acids encoding an Aegyptin or nucleic acids having sequences that complement an Aegyptin gene as they appear in nature can be employed, they will often be altered, e.g., by deletion, substitution, or insertion and can be accompanied by sequence not present in humans. As used herein, regulatory elements include, but are not limited to, inducible and non-inducible promoters, enhancers, operators and other elements known to those skilled in the art that drive and regulate expression. Such regulatory elements include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

In addition, recombinant Aegyptin-encoding nucleic acid sequences and their complementary sequences can be engineered so as to modify processing or expression of the Aegyptin. For example, and not by way of limitation, the Aegyptin gene can be combined with a promoter sequence and/or ribosome binding site, or a signal sequence can be inserted upstream of Aegyptin-encoding sequences to permit secretion of the Aegyptin and thereby facilitate harvesting or bioavailability. Additionally, a given Aegyptin nucleic acid can be mutated in vitro or in vivo, to create and/or destroy translation, initiation, and/or termination sequences, or to create variations in coding regions and/or form new restriction sites or destroy preexisting ones, or to facilitate further in vitro modification. Any technique for mutagenesis known in the art can be used, including but not limited to, in vitro site-directed mutagenesis. (Hutchinson et al., *J. Biol. Chem.*, 253:6551 (1978), herein incorporated by reference).

Further, nucleic acids encoding other proteins or domains of other proteins can be joined to nucleic acids encoding an Aegyptin so as to create a fusion protein. Nucleotides encoding fusion proteins can include, but are not limited to, a full length Aegyptin, a truncated Aegyptin or a peptide fragment of an Aegyptin fused to an unrelated protein or peptide, such as for example, a transmembrane sequence, which better anchors the Aegyptin peptide fragment to the cell membrane; an Ig Fc domain which increases the stability and half life of the resulting fusion protein (e.g., Aegyptin-Ig); or an enzyme, fluorescent protein, luminescent protein which can be used as a marker (e.g., an Aegyptin-Green Fluorescent Protein ("Aegyptin-GFP") fusion protein). The fusion proteins are useful as biotechnological tools or pharmaceuticals or both, as will be discussed infra. The section below describes several of the polypeptides of the invention and methods of making these molecules.

Aegyptin Polypeptides

Aegyptins, Aegyptin polypeptides, fragments of these molecules, and chemicals that resemble these molecules including, but not limited to peptidomimetics, modified Aegyptins, and derivatives or variants of Aegyptins are also embodiments. Aegyptin polypeptides can be present either naturally or through genetic engineering in a number of organisms (e.g., plants, insects, amphibians, reptiles, birds, other animals, cats, dogs, rodents, primates, humans, and other mammals). The Aegyptin family members have a novel structure that contains an acidic N-terminal region and a basic C-terminal region.

Aegyptin has a cleaved, N-terminal signal peptide that allows for insertion into membranes via a conventional ER-to-Golgi routing (FIG. 1A).

The nucleic acids encoding an Aegyptin or fragments thereof, described in the previous section, can be manipulated using conventional techniques in molecular biology so as to create recombinant constructs that express Aegyptin protein or fragments of Aegyptin protein. The Aegyptin polypeptides or derivatives thereof, include but are not limited to, those containing as a primary amino acid sequence all of the amino acid sequence substantially as depicted in the Sequence Listing (SEQ ID NO: 2) and fragments of SEQ ID NO: 2 at least three amino acids in length including altered sequences in which functionally equivalent amino acid residues are substituted for residues within the sequence resulting in a silent change. Preferred fragments of a sequence of SEQ ID NO: 2 are at least three amino acids and comprise amino acid sequence unique to Aegyptins including altered sequences in which functionally equivalent amino acid residues are substituted for residues within the sequence resulting in a silent change. The Aegyptin peptide fragments can comprise, consist, or consist essentially of peptides that are less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 115, 130, 150, 175, 200, 225, 250, 270 or 273 amino acids in length.

Embodiments encompass proteins that are functionally equivalent to the Aegyptins encoded by the nucleotide sequences described in SEQ ID NO: 2, as judged by any of a number of criteria, including but not limited to the ability to bind collagen, the binding affinity for a particular matrix protein, the resulting biological effect of Aegyptin interaction, e.g., change in platelet adhesion, activation and aggregation. Such functionally equivalent Aegyptins include, but are not limited to, additions or substitutions of amino acid residues within the amino acid sequence encoded by the Aegyptin nucleotide sequences described above but, which result in a silent change, thus producing a functionally equivalent gene product. For example, embodiments include Aegyptins that have one or more amino acid residues within the Aegyptin polypeptide of SEQ ID NO: 2 and fragments of SEQ ID NO: 2 that are substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

Additional embodiments include mutant Aegyptins (e.g., Aegyptin), wherein one or more amino acid residues within the Aegyptin polypeptide of SEQ ID NO: 2 and fragments of SEQ ID NO: 2 are substituted by another amino acid resulting in a non-conservative change. While random mutations can be made to Aegyptin DNA (using random mutagenesis techniques well known to those skilled in the art) and the resulting mutant Aegyptins tested for activity, site-directed mutations of the Aegyptin coding sequence can be engineered (using site-directed mutagenesis techniques well known to those skilled in the art) to generate mutant Aegyptins with increased function, e.g., higher binding affinity for a specific matrix protein, and/or greater fibrinolysis promotion capability; or decreased function, e.g., lower binding affinity for a particular matrix protein, and/or decreased fibrinolysis promotion capability.

Non-conservative changes can be engineered at these variable positions to alter function, e.g., collagen binding affinity or capability to inhibit platelet adhesion, activation and aggregation promotion, or both. Alternatively, where alteration of function is desired, deletion or non-conservative alterations of the conserved regions can be engineered. For example, deletion or non-conservative alterations (substitutions or insertions) of amino acid residues in regions of the polypeptide can be engineered to produce a mutant Aegyptin that binds collagen but does not inhibit platelet adhesion, activation and aggregation.

Other embodiments include polypeptides that have homology to an Aegyptin and function as a membrane bound modulator of platelet adhesion, activation and aggregation. The term "homology to Aegyptin" is meant to include nucleic acid or protein sequence homology or three-dimensional homology. Several techniques exist to determine nucleic acid or protein sequence homology and/or three-dimensional homology of proteins. These methods are routinely employed to discover the extent of homology that one sequence, domain, or model has to a target sequence, domain, or model. Because the region of Aegyptin that modulates fibrinolysis can be quite small (e.g., 3, 4, 5, 6, 7, 8, 9, 10, 12, 15, 18, 20, 22, 25, 30 amino acids in length), embodiments of the invention can exhibit a vast degree of homology to full-length Aegyptin. For example, a fusion protein having a small region of Aegyptin can exhibit a low degree of overall homology to Aegyptin yet retain the ability to function as a modulator of platelet adhesion, activation and aggregation equivalent to Aegyptin. Thus, some embodiments can have from 1% homology to 100% homology to full-length Aegyptin. That is, embodiments can comprise, consist, or consist essentially of 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, 21.0%, 22.0%, 23.0%, 24.0%, 25.0%, 26.0%, 27.0%, 28.0%, 29.0%, 30.0%, 31.0%, 32.0%, 33.0%, 34.0%, 35.0%, 36.0%, 37.0%, 38.0%, 39.0%, 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% homology to a full-length Aegyptin (e.g., Aegyptin).

Therefore, embodiments include polypeptides varying in size from 3 amino acids up to and including the full-length Aegyptin protein that have 1%-100% homology to an Aegyptin and exhibit the ability to function as a membrane-bound modulator of platelet adhesion, activation and aggregation. Several homology searching programs based on nucleic acid or amino acid sequence are known in the art and can be used to identify molecules that are homologous to Aegyptin. Some approaches to identify molecules homologous to Aegyptins are provided infra.

The Aegyptins and Aegyptin-like hybrids can be prepared by chemical synthesis methods (such as solid phase peptide synthesis) using techniques known in the art such as those set forth by Merrifield et al., *J. Am. Chem. Soc.* 85:2149 (1964), Houghten et al., *Proc. Natl. Acad. Sci. USA,* 82:51:32 (1985), Stewart and Young (*Solid phase peptide synthesis*, Pierce Chem Co., Rockford, Ill. (1984), and Creighton, 1983, *Proteins: Structures and Molecular Principles*, W.H. Freeman & Co., N.Y. herein incorporated by reference. Such polypeptides can be synthesized with or without a methionine on the amino terminus. Chemically synthesized Aegyptin and fragments of Aegyptin can be oxidized using methods set forth in these references to form disulfide bridges. Aegyptins and fragments of Aegyptin can be employed as biologically active or immunological substitutes for natural, purified Aegyptin and fragments of Aegyptin.

While the Aegyptins and hybrids can be chemically synthesized, it can be more effective to produce these polypeptides by recombinant DNA technology using techniques well known in the art. Such methods can be used to construct expression vectors containing the Aegyptin nucleotide sequences, for example, and appropriate transcriptional and translational control signals. These methods include, for example, in vitro recombinant DNA techniques, synthetic techniques, and in vivo genetic recombination. Alternatively, RNA capable of encoding an Aegyptin nucleotide sequences can be chemically synthesized using, for example, synthesizers. See, for example, the techniques described in *Oligonucleotide Synthesis,* 1984, Gait, M. J. ed., IRL Press, Oxford, which is incorporated by reference herein in its entirety.

In several embodiments, Aegyptins, fragments of Aegyptins, and Aegyptin-like hybrids are expressed in a cell line. For example, some cells are made to express the Aegyptin polypeptide of SEQ ID NO: 2 or fragments of SEQ ID NO: 2. The sequences, constructs, vectors, clones, and other materials comprising the present invention can advantageously be in enriched or isolated form. As used herein, "enriched" means that the concentration of the material is at least about 2, 5, 10, 100, or 1000 times its natural concentration (for example), advantageously 0.01%, by weight, preferably at least about 0.1% by weight. Enriched preparations from about 0.5%, 1%, 5%, 10%, and 20% by weight are also contemplated. The term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. It is also advantageous that the sequences be in purified form. The term "purified" does not require absolute purity; rather, it is intended as a relative definition. Isolated proteins have been conventionally purified to electrophoretic homogeneity by Coomassie staining, for example. Purification of starting material or natural material to at least one order of magnitude, preferably two or three orders, and more preferably four or five orders of magnitude is expressly contemplated.

A variety of host-expression vector systems can be utilized to express the Aegyptins of the invention. Where the Aegyptin or hybrid is a soluble derivative (e.g., hybrids having a truncated or deleted hydrophobic domain) it can be recovered from the culture, i.e., from the host cell in cases where the peptide or polypeptide is not secreted, and from the culture media in cases where the peptide or polypeptide is secreted by the cells. However, the expression systems also encompass engineered host cells that express the Aegyptin or functional equivalents in situ, i.e., anchored in the cell membrane. Purification or enrichment of the Aegyptin from such expression systems can be accomplished using appropriate detergents and lipid micelles and methods well known to those skilled in the art. However, such engineered host cells themselves can be used in situations where it is important not only to retain the structural and functional characteristics of the Aegyptin, but to assess biological activity, e.g., in drug screening assays.

The expression systems that can be used for purposes of the invention include, but are not limited to, microorganisms such as bacteria (e.g., *E. coli* or *B. subtilis*) transformed with recombinant bacteriophage DNA, plasmid DNA or cosmid DNA expression vectors containing Aegyptin nucleotide sequences; yeast (e.g., *Saccharomyces, Pi chia*) transformed with recombinant yeast expression vectors containing the Aegyptin nucleotide sequences; insect cell systems infected with recombinant virus expression vectors (e.g., baculovirus) containing the Aegyptin sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Aegyptin nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the Aegyptin gene product being expressed. For example, when a large quantity of such a protein is to be produced, for the generation of pharmaceutical compositions of Aegyptin protein or for raising antibodies to the Aegyptin protein, for example, vectors which direct the expression of high levels of fusion protein products that are readily purified can be desirable. Such vectors include, but are not limited, to the *E. coli* expression vector pUR278 (Ruther et al., *EMBO J.,* 2:1791 (1983), in which the Aegyptin coding sequence can be ligated individually into the vector in frame with the lacZ coding region so that a fusion protein is produced; pIN vectors (Inouye & Inouye, *Nucleic Acids Res.,* 13:3101-3109 (1985); Van Heeke & Schuster, *J. Biol. Chem.,* 264:5503-5509 (1989)); and the like. pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The Aegyptin gene coding sequence can be cloned individually into non-essential regions (for example, the polyhedrin gene) of the virus and placed under control of an AcNPV promoter (for example, the polyhedrin promoter). Successful insertion of Aegyptin gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al., *J. Virol.* 46: 584 (1983); and Smith, U.S. Pat. No. 4,215,051).

In mammalian host cells, a number of viral-based expression systems can be utilized. In cases where an adenovirus is used as an expression vector, the Aegyptin nucleotide sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the Aegyptin gene product in infected hosts. (E.g., See Logan & Shenk, *Proc. Natl. Acad. Sci. USA* 81:3655-3659 (1984)). Specific initiation signals can also be required for efficient translation of inserted Aegyptin nucleotide sequences. These signals include the ATG initiation codon and adjacent sequences. In cases where an entire Aegyptin gene or cDNA, including its own initiation codon and adjacent sequences, is inserted into the appropriate expression vector, no additional translational control signals are needed.

However, in cases where only a portion of the Aegyptin coding sequence is inserted, exogenous translational control signals, including, perhaps, the ATG initiation codon, should be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See Bittner et al., *Methods in Enzymol.*, 153:516-544 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products are important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, and WI38.

For long-term, high-yield production of recombinant proteins, stable expression is preferred. For example, cell lines that stably express the Aegyptin sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express the Aegyptin gene product. Such engineered cell lines are particularly useful in screening and evaluation of compounds that affect the endogenous activity of the Aegyptin gene product.

A number of selection systems can be used, including but not limited to the herpes simplex virus thymidine kinase (Wigler, et al., *Cell* 11:223 (1977), hypoxanthine-guanine phosphoribosyltransferase (Szybalska & Szybalski, *Proc. Natl. Acad. Sci. USA* 48:2026 (1962), and adenine phosphoribosyltransferase (Lowy, et al., *Cell* 22:817 (1980) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., *Proc. Natl. Acad. Sci. USA* 77:3567 (1980); O'Hare, et al., *Proc. Natl. Acad. Sci. USA* 78:1527 (1981); gpt, which confers resistance to mycophenolic acid (Mulligan & Berg, *Proc. Natl. Acad. Sci. USA* 78:2072 (1981); neo, which confers resistance to the aminoglycoside G-418 (Colberre-Garapin, et al., *J. Mol. Biol.* 150:1 (1981); and hygro, which confers resistance to hygromycin (Santerre, et al., *Gene* 30:147 (1984)).

Alternatively, any fusion protein can be readily purified by utilizing an antibody specific for the fusion protein being expressed. For example, a system described by Janknecht et al. allows for the ready purification of non-denatured fusion proteins expressed in human cell lines. (Janknecht, et al., *Proc. Natl. Acad. Sci. USA* 88: 8972-8976 (1991)). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers. Example 2 provides a more detailed description of methods to express the proteins encoded by the nucleic acids of the invention.

The Aegyptin gene products can also be expressed in plants, insects, and animals so as to create a transgenic organism. Plants and insects of almost any species can be made to express an Aegyptin, fragments of Aegyptin, or Aegyptin-like hybrid. Desirable transgenic plant systems having an Aegyptin, fragments of Aegyptin, or Aegyptin-like hybrid include *Arabadopsis*, maize, and chlamydomonas. Desirable insect systems an Aegyptin, fragments of Aegyptin, or Aegyptin-like hybrid include, for example, *D. melanogaster* and *C. elegans*. Animals of any species, including, but not limited to, amphibians, reptiles, birds, mice, rats, rabbits, guinea pigs, pigs, micro-pigs, goats, dogs, cats, and non-human primates, e.g., baboons, monkeys, and chimpanzees can be used to generate Aegyptin transgenic animals. Transgenic organisms of the invention desirably exhibit germline transfer of wild-type or mutant Aegyptins, fragments of Aegyptin, or Aegyptin-like hybrids. Other transgenic organisms are engineered to express human Aegyptins, fragments of Aegyptins, or Aegyptin-like hybrids. Still other transgenic organisms of the invention exhibit complete knockouts or point mutations of one or more existing Aegyptin genes. For example, in one embodiment, a transgenic animal comprises a knockout of Aegyptin and in another embodiment, a transgenic animal comprises at least one point mutation in Aegyptin.

Any technique known in the art is preferably used to introduce the Aegyptin transgene into animals to produce the founder lines of transgenic animals or to knock out or replace existing Aegyptin genes. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., *Proc. Natl. Acad. Sci., USA* 82:6148-6152 (1985); gene targeting in embryonic stem cells (Thompson et al., *Cell* 56:313-321 (1989); electroporation of embryos (Lo, *Mol Cell. Biol.* 3:1803-1814 (1983); and sperm-mediated gene transfer (Lavitrano et al., *Cell* 57:717-723 (1989); etc. For a review of such techniques, see Gordon, *Transgenic Animals, Intl. Rev. Cytol.* 115:171-229 (1989), which is incorporated by reference herein in its entirety.

Aspects of the invention provide for transgenic animals that carry an Aegyptin transgene in all their cells, as well as animals that carry the transgene in some, but not all their cells, i.e., mosaic animals. The transgene can be integrated as a single transgene or in concatamers, e.g., head-to-head tandems or head-to-tail tandems. The transgene can also be selectively introduced into and activated in a particular cell type by following, for example, the teaching of Lasko et al. (Lasko, M. et al., *Proc. Natl. Acad. Sci. USA* 89: 6232-6236 (1992)). The regulatory sequences required for such a cell-type specific activation will depend upon the particular cell type of interest, and will be apparent to those of skill in the art.

When it is desired that the Aegyptin gene transgene be integrated into the chromosomal site of the endogenous Aegyptin gene, gene targeting is preferred. Briefly, when such a technique is to be utilized, vectors containing some nucleotide sequences homologous to the endogenous Aegyptin gene are designed for the purpose of integrating, via homologous recombination with chromosomal sequences, into and disrupting the function of the nucleotide sequence of the endogenous Aegyptin gene. The transgene can also be selectively introduced into a particular cell type, thus inactivating the endogenous Aegyptin gene in only that cell type, by following, for example, the teaching of Gu et al. (Gu, et al., Science 265: 103-106 (1994)). The regulatory sequences required for such a cell-type specific inactivation will depend upon the particular cell type of interest, and will be apparent to those of skill in the art.

Once transgenic animals have been generated, the expression of the recombinant Aegyptin gene can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and RT-PCR. Samples of Aegyptin gene-expressing tissue can also be evaluated immunocytochemically using antibodies specific for the Aegyptin transgene product.

In addition to the naturally occurring Aegyptins or peptide-based hybrids, embodiments include derivative or modified molecules that produce a more desirable cellular response. For example, a derivative Aegyptin can include a polypeptide that has been engineered to have one or more cystine residues incorporated into the protein so as to promote the formation of a more stable derivative through disulfide bond formation. (See e.g., U.S. Pat. No. 4,908,773). In the past, investigators have employed computers and computer graphics programs to aid in assessing the appropriateness of potential cystine linkage sites. (Perry, L. J., & Wetzel, R., Science, 226:555-557 (1984); Pabo, C. O., et al., Biochemistry, 25:5987-5991 (1986); Bott, R., et al., European Patent Application Ser. No. 130,756; Perry, L. J., & Wetzel, R., Biochemistry, 25:733-739 (1986); Wetzel, R. B., European Patent Application Ser. No. 155,832). The introduction of a cystine residue in a polypeptide can be accomplished using conventional molecular biology techniques.

Additional Aegyptin and hybrid derivatives include peptidomimetics that resemble a polypeptide of interest. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a particular peptide, e.g., an oligopeptide, once such peptide has been found, but that avoids the undesirable features, e.g., flexibility (loss of conformation) and bond breakdown are known as a "peptidomimetics". (See, e.g., Spatola, A. F. Chemistry and Biochemistry of Amino Acids. Peptides, and Proteins (Weistein, B, Ed.), Vol. 7, pp. 267-357, Marcel Dekker, New York (1983), which describes the use of the methylenethio bioisostere [$CH_2S$] as an amide replacement in enkephalin analogues; and Szelke et al., In peptides: Structure and Function, Proceedings of the Eighth American Peptide Symposium, (Hruby and Rich, Eds.); pp. 579-582, Pierce Chemical Co., Rockford, Ill. (1983), which describes renin inhibitors having both the methyleneamino [$CH_2NH$] and hydroxyethylene [$CHOHCH_2$] bioisosteres at the Leu-Val amide bond in the 6-13 octapeptide derived from angiotensinogen).

In general, the design and synthesis of a peptidomimetic involves starting with the amino acid sequence of the peptide and conformational data (e.g., geometry data, such as bond lengths and angles) of a desired peptide (e.g., the most probable simulated peptide). That data is then used to determine the geometries that should be designed into the peptidomimetic. Numerous methods and techniques are known in the art for performing this step, any of which could be used. (See, e.g., Farmer, P. S., Drug Design, (Ariens, E. J. ed.), Vol. 10, pp. 119-143 (Academic Press, New York, London, Toronto, Sydney and San Francisco) (1980); Farmer, et al., in TIPS, 9/82, pp. 362-365; Verber et al., in TINS, 9/85, pp. 392-396; Kaltenbronn et al., in J. Med. Chem. 33: 838-845 (1990); and Spatola, A. F., in Chemistry and Biochemistry of Amino Acids. Peptides, and Proteins, Vol. 7, pp. 267-357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of beta-sheets and alpha-helices in Peptides," Tibech, Vol. 8, pp. 249-255 (1990). Additional teachings can be found in U.S. Pat. Nos. 5,288,707; 5,552,534; 5,811,515; 5,817,626; 5,817, 879; 5,821,231; and 5,874,529. The section below describes antibodies of the invention and methods of making these molecules.

Anti-Aegyptin Antibodies

Following synthesis or expression and isolation or purification of the Aegyptin protein or a portion thereof, the isolated or purified protein can be used to generate antibodies and tools for identifying agents that interact with Aegyptin and fragments of Aegyptin. Depending on the context, the term "antibodies" can encompass polyclonal, monoclonal, chimeric, single chain, Fab fragments and fragments produced by a Fab expression library. Antibodies that recognize Aegyptin and fragments of Aegyptin have many uses including, but not limited to, biotechnological applications, therapeutic/prophylactic applications, and diagnostic applications.

For the production of antibodies, various hosts including goats, rabbits, rats, mice, etc. can be immunized by injection with Aegyptin or any portion, fragment or oligopeptide that retains immunogenic properties. Depending on the host species, various adjuvants can be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and Corynebacterium parvum are also potentially useful adjuvants.

Peptides used to induce specific antibodies can have an amino acid sequence consisting of at least three amino acids, and preferably at least 10 to 15 amino acids. Preferably, short stretches of amino acids encoding fragments of Aegyptin are fused with those of another protein such as keyhole limpet hemocyanin such that an antibody is produced against the chimeric molecule. While antibodies capable of specifically recognizing Aegyptin can be generated by injecting synthetic 3-mer, 10-mer, and 15-mer peptides that correspond to a protein sequence of Aegyptin into mice, a more diverse set of antibodies can be generated by using recombinant Aegyptin, purified Aegyptin, or fragments of Aegyptin.

To generate antibodies to Aegyptin and fragments of Aegyptin, substantially pure Aegyptin or a fragment of Aegyptin is isolated from a transfected or transformed cell. The concentration of the polypeptide in the final preparation is adjusted, for example, by concentration on an Amicon filter device, to the level of a few micrograms/ml. Monoclonal or polyclonal antibody to the polypeptide of interest can then be prepared as follows:

Monoclonal antibodies to Aegyptin or a fragment of Aegyptin can be prepared using any technique that provides for the production of antibody molecules by continuous cell lines in culture. These include, but are not limited to, the hybridoma technique originally described by Koehler and Milstein (*Nature* 256:495-497 (1975), the human B-cell hybridoma technique (Kosbor et al. *Immunol Today* 4:72 (1983); Cote et al *Proc Natl Acad Sci* 80:2026-2030 (1983), and the EBV-hybridoma technique Cole et al. *Monoclonal Antibodies and Cancer Therapy*, Alan R. Liss Inc, New York N.Y., pp 77-96 (1985). In addition, techniques developed for the production of "chimeric antibodies", the splicing of mouse antibody genes to human antibody genes to obtain a molecule with appropriate antigen specificity and biological activity can be used. (Morrison et al. *Proc Natl Acad Sci* 81:6851-6855 (1984); Neuberger et al. Nature 312:604-608 (1984); Takeda et al. *Nature* 314:452-454(1985). Alternatively, techniques described for the production of single chain antibodies (U.S. Pat. No. 4,946,778) can be adapted to produce Aegyptin-specific single chain antibodies. Antibodies can also be produced by inducing in vivo production in the lymphocyte population or by screening recombinant immunoglobulin libraries or panels of highly specific binding reagents as disclosed in Orlandi et al., *Proc Natl Acad Sci* 86: 3833-3837 (1989), and Winter G. and Milstein C; *Nature* 349:293-299 (1991).

Antibody fragments that contain specific binding sites for Aegyptin can also be generated. For example, such fragments include, but are not limited to, the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries can be constructed to allow rapid and easy identification of monoclonal Fab fragments with the desired specificity. (Huse W. D. et al. *Science* 256:1275-1281 (1989)).

By one approach, monoclonal antibodies to Aegyptin or fragments thereof are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, N.Y. Section 21-2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and can require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. (See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980)). Antibody preparations prepared according to either protocol are useful in quantitative immunoassays that determine concentrations of antigen-bearing substances in biological samples; they are also used semi-quantitatively or qualitatively (e.g., in diagnostic embodiments that identify the presence of Aegyptin in biological samples). In the discussion that follows, several methods of molecular modeling and rational drug design are described. These techniques can be applied to identify additional Aegyptin family members, compounds that resemble an Aegyptin or fragment or derivative thereof, and molecules that interact with Aegyptins and, thereby modulate their function.

Rational Drug Design

Rational drug design involving polypeptides requires identifying and defining a first peptide with which the designed drug is to interact, and using the first target peptide to define the requirements for a second peptide. With such requirements defined, one can find or prepare an appropriate peptide or non-peptide that meets all or substantially all of the defined requirements. Thus, one goal of rational drug design is to produce structural or functional analogs of biologically active polypeptides of interest or of small molecules with which they interact (e.g., agonists, antagonists, null compounds) in order to fashion drugs that are, for example, more or less potent forms of the ligand. (See, e.g., Hodgson, *Bio. Technology* 9:19-21 (1991)). An example of rational drug design is shown in Erickson et al., *Science* 249:527-533 (1990). Combinatorial chemistry is the science of synthesizing and testing compounds for bioactivity en masse, instead of one by one, the aim being to discover drugs and materials more quickly and inexpensively than was formerly possible. Rational drug design and combinatorial chemistry have become more intimately related in recent years due to the development of approaches in computer-aided protein modeling and drug discovery. (See e.g., U.S. Pat. Nos. 4,908,773; 5,884,230; 5,873,052; 5,331,573; and 5,888,738).

The use of molecular modeling as a tool for rational drug design and combinatorial chemistry has dramatically increased due to the advent of computer graphics. Not only is it possible to view molecules on computer screens in three dimensions but it is also possible to examine the interactions of macromolecules such as enzymes and receptors and rationally design derivative molecules to test. (See Boorman, *Chem. Eng. News* 70:18-26 (1992). A vast amount of userfriendly software and hardware is now available and virtually all pharmaceutical companies have computer modeling groups devoted to rational drug design. Molecular Simulations Inc., for example, sells several sophisticated programs that allow a user to start from an amino acid sequence, build a two or three-dimensional model of the protein or polypeptide, compare it to other two and three-dimensional models, and analyze the interactions of compounds, drugs, and peptides with a three dimensional model in real time. Accordingly, in some embodiments of the invention, software is used to compare regions of Aegyptins (e.g., Aegyptin) and molecules that interact with Aegyptins (collectively referred to as "binding partners"—e.g., anti-Aegyptin antibodies, and collagen), and fragments or derivatives of these molecules with other molecules, such as peptides, peptidomimetics, and chemicals, so that therapeutic interactions can be predicted and designed. (See Schneider, *Genetic Engineering News* December: page 20 (1998), Tempczyk et al., *Molecular Simulations Inc. Solutions* April (1997) and Butenhof, *Molecular Simulations Inc. Case Notes* (August 1998) *for a discussion of molecular modeling*).

For example, the protein sequence of an Aegyptin or binding partner, or domains of these molecules (or nucleic acid sequence encoding these polypeptides or both), can be entered onto a computer readable medium for recording and manipulation. It will be appreciated by those skilled in the art that a computer readable medium having these sequences can interface with software that converts or manipulates the sequences to obtain structural and functional information, such as protein models. That is, the functionality of a software program that converts or manipulates these sequences includes the ability to compare these sequences to other sequences or structures of molecules that are present on publicly and commercially available databases so as to conduct rational drug design.

The Aegyptin or binding partner polypeptide or nucleic acid sequence or both can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on a computer readable medium to generate manufactures comprising the nucleotide or polypeptide sequence information of this embodiment. A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments of the invention utilize computer-based systems that contain the sequence information described herein and convert this information into other types of usable information (e.g., protein models for rational drug design). The term "a computer-based system" refers to the hardware, software, and any database used to analyze an Aegyptin or a binding partner nucleic acid or polypeptide sequence or both, or fragments of these biomolecules so as to construct models or to conduct rational drug design. The computer-based system preferably includes the storage media described above, and a processor for accessing and manipulating the sequence data. The hardware of the computer-based systems of this embodiment comprise a central processing unit (CPU) and a database. A skilled artisan can readily appreciate that any one of the currently available computer-based systems are suitable.

In one particular embodiment, the computer system includes a processor connected to a bus that is connected to a main memory (preferably implemented as RAM) and a variety of secondary storage devices, such as a hard drive and removable medium storage device. The removable medium storage device can represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein can be inserted into the removable storage device. The computer system includes appropriate software for reading the control logic and/or the data from the removable medium storage device once inserted in the removable medium storage device. The Aegyptin or binding partner nucleic acid or polypeptide sequence or both can be stored in a well known manner in the main memory, any of the secondary storage devices, and/or a removable storage medium. Software for accessing and processing these sequences (such as search tools, compare tools, and modeling tools etc.) reside in main memory during execution.

As used herein, "a database" refers to memory that can store an Aegyptin or binding partner nucleotide or polypeptide sequence information, protein model information, information on other peptides, chemicals, peptidomimetics, and other agents that interact with Aegyptin proteins, and values or results from functional assays. Additionally, a "database" refers to a memory access component that can access manufactures having recorded thereon Aegyptin or binding partner nucleotide or polypeptide sequence information, protein model information, information on other peptides, chemicals, peptidomimetics, and other agents that interact with Aegyptins, and values or results from functional assays. In other embodiments, a database stores an "Aegyptin functional profile" comprising the values and results (e.g., ability to associate with collagen or modulate platelet adhesion, activation and aggregation) from one or more "Aegyptin functional assays", as described herein or known in the art, and relationships between these values or results. The sequence data and values or results from Aegyptin functional assays can be stored and manipulated in a variety of data processor programs in a variety of formats. For example, the sequence data can be stored as text in a word processing file, an ASCII file, a html file, or a pdf file in a variety of database programs familiar to those of skill in the art.

A "search program" refers to one or more programs that are implemented on the computer-based system to compare an Aegyptin or binding partner nucleotide or polypeptide sequence with other nucleotide or polypeptide sequences and agents including but not limited to peptides, peptidomimetics, and chemicals stored within a database. A search program also refers to one or more programs that compare one or more protein models to several protein models that exist in a database and one or more protein models to several peptides, peptidomimetics, and chemicals that exist in a database. A search program is used, for example, to compare one Aegyptin functional profile to one or more Aegyptin functional profiles that are present in a database. Still further, a search program can be used to compare values or results from Aegyptin functional assays and agents that modulate platelet adhesion, activation and aggregation.

A "retrieval program" refers to one or more programs that can be implemented on the computer-based system to identify a homologous nucleic acid sequence, a homologous protein sequence, or a homologous protein model. A retrieval program can also used to identify peptides, peptidomimetics, and chemicals that interact with an Aegyptin protein sequence, or an Aegyptin protein model stored in a database. Further, a retrieval program is used to identify a specific agent that modulates Aegyptin-mediated inhibition of platelet adhesion, activation and aggregation to a desired set of values, results, or profile. That is, a retrieval program can also be used to obtain "a binding partner profile" that is composed of a chemical structure, nucleic acid sequence, or polypeptide sequence or model of an agent that interacts with an Aegyptin and, thereby modulates (inhibits or enhances) platelet adhesion, activation and aggregation. Further, a binding partner profile can have one or more symbols that represent these molecules and/or models, an identifier that represents one or more agents including, but not limited to peptides and peptidomimetics (referred to collectively as "peptide agents") and chemicals, and a value or result from a functional assay.

As a starting point to rational drug design, a two or three dimensional model of a polypeptide of interest is created (e.g., Aegyptin, or a binding partner, such as a collagen or an antibody). In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221-239 (1971). Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, 4th Edition, Prentice-Hall, N.J. (1972)).

Alternatively, protein models of a polypeptide of interest can be constructed using computer-based protein modeling techniques. By one approach, the protein folding problem is solved by finding target sequences that are most compatible with profiles representing the structural environments of the residues in known three-dimensional protein structures. (See, e.g., U.S. Pat. No. 5,436,850). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., U.S. Pat. Nos. 5,557,535; 5,884,230; and 5,873,052). Conventional homology modeling techniques have been used routinely to build models of proteases and antibodies. (Sowdhamini et al., *Protein Engineering* 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using a distance geometry program that constructs a low resolution model. A full-atom representation is then constructed using a molecular modeling package.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program, together with auxiliary information obtained from secondary structure predictions. The program combines the restraints in an unbiased manner and rapidly generates a large number of low resolution model confirmations. In a third step, these low resolution model confirmations are converted into full-atom models and organismed to energy minimization using the molecular modeling package. (See e.g., Aszódi et al., Proteins: Structure, Function, and Genetics, Supplement 1:38-42 (1997)).

In a preferred approach, a commercially available program (Molecular Simulations Inc.) and accompanying modules are used to create a two and/or three dimensional model of a polypeptide of interest from an amino acid sequence. A three-dimensional graphics program that can interface with several modules that perform numerous structural analysis and enable real-time rational drug design and combinatorial chemistry is commercially available. Modules allow one to rapidly create a two dimensional or three dimensional model of a polypeptide, carbohydrate, nucleic acid, chemical or combinations of the foregoing from their sequence or structure. The modeling tools associated with these programs support many different data file formats including Brookhaven and Cambridge databases; AMPAC/MOPAC and QCPE programs; Molecular Design Limited Molfile and SD files, Sybel Mol2 files, VRML, and Pict files.

Additionally, the techniques described above can be supplemented with techniques in molecular biology to design models of the protein of interest. For example, a polypeptide of interest can be analyzed by an alanine scan (Wells, Methods in Enzymol. 202:390-411 (1991)) or other types of site-directed mutagenesis analysis. In alanine scan, each amino acid residue of the polypeptide of interest is sequentially replaced by alanine in a step-wise fashion (i.e., only one alanine point mutation is incorporated per molecule starting at position #1 and proceeding through the entire molecule), and the effect of the mutation on the peptide's activity in a functional assay is determined. Each of the amino acid residues of the peptide is analyzed in this manner and the regions important for the modulation of platelet adhesion, activation and aggregation, for example, are identified. These functionally important regions can be recorded on a computer readable medium, stored in a database in a computer system, and a search program can be employed to generate a protein model of the functionally important regions.

Once a model of the polypeptide of interest is created, it can be compared to other models so as to identify new members of the Aegyptin family and binding partners. By starting with the amino acid sequence or protein model of Aegyptin or a binding partner, for example, molecules having two-dimensional and/or three-dimensional homology can be rapidly identified. In one approach, a percent sequence identity can be determined by standard methods that are commonly used to compare the similarity and position of the amino acid of two polypeptides. Using a computer program such as BLAST or FASTA, two polypeptides can be aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{[\text{length of the longer sequence within the matched span} + \text{number of gaps introduced into the longer sequence in order to align the two sequences}]} \times 100$$

Accordingly, the protein sequence corresponding to an Aegyptin or a binding partner or a fragment or derivative of these molecules can be compared to known sequences on a protein basis. Protein sequences corresponding to an Aegyptin, or a binding partner or a fragment or derivative of these molecules are compared, for example, to known amino acid sequences found in Swissprot release 35, PIR release 53 and Genpept release 108 public databases using BLASTP with the parameter W=8 and allowing a maximum of 10 matches. In addition, the protein sequences are compared to publicly known amino acid sequences of Swissprot using BLASTX with the parameter E=0.001. The molecules identified as members of the family of Aegyptins or candidate binding partners desirably have at least 35% homology and preferably have 40%, 45%, 50% or 55% or greater homology to Aegyptin The Aegyptin family members and candidate binding partners that interact with an Aegyptin can have the following degrees of homology or identity to Aegyptin or both, for example: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. The Aegyptin family members and candidate binding partners having greater than or equal to 35% homology are identified and are subsequently examined using an Aegyptin functional assay.

In another embodiment, computer modeling and the sequence-to-structure-to-function paradigm is exploited to identify more members of the Aegyptin family candidate binding partners. By this approach, first the structure of an Aegyptin (e.g., Aegyptin) or a candidate binding partner (e.g., somatomedin domain or antibody) having a known response in a characterization assay is determined from its sequence using a threading algorithm, which aligns the sequence to the best matching structure in a structural database. Next, the protein's active site (i.e., the site important for a desired response in the characterization assay) is identified and a "fuzzy functional form" (FFF)—a three-dimensional descriptor of the active site of a protein—is created. (See e.g., Fetrow et al., *J. Mol. Biol.* 282:703-711 (1998) and Fetrow and Skolnick, *J. Mol. Biol.* 281: 949-968 (1998).

The FFFs are built by iteratively superimposing the protein geometries from a series of functionally related proteins with known structures. The FFFs are not overly specific, however, and the degree to which the descriptors can be relaxed is explored. In essence, conserved and functionally important residues for a desired response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained. The ability to search three-dimensional structure databases for structural similarity to a protein of interest can also be accomplished by employing commercially available modules.

By using this computational protocol, genome sequence data bases such as maintained by various organizations can be rapidly screened for specific protein active sites and for identification of the residues at those active sites that resemble a desired molecule. Several other groups have developed databases of short sequence patterns or motifs designed to identify a given function or activity of a protein. Many of these databases can use short stretches of sequence information to identify sequence patterns that are specific for a given function; thus they avoid the problems arising from the necessity of matching entire sequences.

By a similar approach, a candidate binding partner can be identified and manufactured as follows. First, a molecular model of one or more molecules that are known to interact with an Aegyptin or portions of these molecules that interact with an Aegyptin are created using one of the techniques discussed above or as known in the art. Next, chemical libraries and databases are searched for molecules similar in structure to the known molecule. That is, a search can be made of a three dimensional data base for non-peptide (organic) structures (e.g., non-peptide analogs, and/or dipeptide analogs) having three dimensional similarity to the known structure of the target compound. (See, e.g., the Cambridge Crystal Structure Data Base, Crystallographic Data Center, Lensfield Road, Cambridge, CB2 1EW, England; and Allen, F. H., et al., *Acta Crystallogr.*, B35: 2331-2339 (1979).) The identified candidate binding partners that interact with Aegyptins can then be analyzed in a functional assay (e.g., a platelet adhesion, aggregation assay or both) and new molecules can be modeled after the candidate binding partners that produce a desirable response. By cycling in this fashion, libraries of molecules that interact with Aegyptins and produce a desirable or optimal response in a functional assay can be selected.

It is noted that search algorithms for three dimensional data base comparisons are available in the literature. (See, e.g., Cooper, et al., *J. Comput.-Aided Mol. Design*, 3: 253-259 (1989) and references cited therein; Brent, et al., *J. Comput.-Aided Mol. Design*, 2: 311-310 (1988) and references cited therein.) Commercial software for such searches is also available from vendors such as Day Light Information Systems, Inc., Irvine, Calif. 92714, and Molecular Design Limited, 2132 Faralton Drive, San Leandro, Calif. 94577. The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the receptor substrate interactions.

By another approach, protein models of binding partners that interact with an Aegyptin (e.g., a collagen molecule or an antibody) can be made by the methods described above and these models can be used to predict the interaction of new molecules. Once a model of a binding partner is identified, the active sites or regions of interaction can be identified. Such active sites might typically be ligand binding sites. The active site can be identified using methods known in the art including, for example, from the amino acid sequences of peptides, from the nucleotide sequences of nucleic acids, or from study of complexes of the Aegyptin with a ligand, such as a collagen molcule or specific matrix proteins. In the latter case, chemical or X-ray crystallographic methods can be used to find the active site by finding where on the Aegyptin the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method can be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site of the known binding partner, either experimentally, by modeling, or by a combination, candidate binding partners can be identified by searching databases containing compounds along with information on their molecular structure. Such a search seeks compounds having structures that match the determined active site structure and that interact with the groups defining the active site. Such a search can be manual, but is preferably computer assisted.

Alternatively, these methods can be used to identify improved binding partners from an already known binding partner. The composition of the known binding partner can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

A number of articles review computer modeling of drugs interactive with specific-proteins, such as Rotivinen, et al., 1988, Acta Pharmaceutical Fennica 97:159-166; Ripka, New Scientist 54-57 (Jun. 16, 1988); McKinaly and Rossmann, 1989, Annu. Rev. Pharmacol. Toxiciol. 29:111-122; Perry and Davies, OSAR: Quantitative Structure-Activity Relationships in Drug Design pp. 189-193 (Alan R. Liss, Inc. 1989); Lewis and Dean, 1989 Proc. R. Soc. Lond. 236:125-140 and 141-162; and, with respect to a model receptor for nucleic acid components, Askew, et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific for the modulation of platelet adhesion, activation and aggregation, and other Aegyptin functions.

Many more computer programs and databases can be used with embodiments of the invention to identify new members of the Aegyptin family and binding partners that modulate Aegyptin function. The following list is intended not to limit the invention but to provide guidance to programs and databases that are useful with the approaches discussed above. The programs and databases that can be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990), herein incorporated by reference), FASTA (Pearson and Lipman, *Proc. Natl. Acad Sci. USA,* 85: 2444 (1988), herein incorporated by reference), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217-241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), Biopendium (Inpharmatica), SBdBase (Structural Bioinformatics), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure.

Once candidate binding partners have been identified, desirably, they are analyzed in a functional assay. Further cycles of modeling and functional assays can be employed to more narrowly define the parameters needed in a binding partner. Each binding partner and its response in a functional assay can be recorded on a computer readable media and a database or library of binding partners and respective responses in a functional assay can be generated. These databases or libraries can be used by researchers to identify important differences between active and inactive molecules so that compound libraries are enriched for binding partners that have favorable characteristics. The section below describes several Aegyptin functional assays that can be used to characterize new Aegyptin family members and candidate binding partners.

Aegyptin Characterization Assays

The term "Aegyptin characterization assay" or "Aegyptin functional assay" or "functional assay" the results of which can be recorded as a value in a "Aegyptin functional profile", include assays that directly or indirectly evaluate the presence of an Aegyptin nucleic acid or protein in a cell and the ability of an Aegyptin to modulate platelet adhesion, activation and aggregation. Examples 5-6 and 8-10 teach assays that are considered for the purposes of this disclosure to be Aegyptin functional assays. Many more are provided in the discussion below.

Some functional assays involve binding assays that utilize multimeric agents. One form of multimeric agent concerns a manufacture comprising an Aegyptin, hybrid, binding partner, or fragment thereof disposed on a support. These multimeric agents provide the Aegyptin, hybrid, binding partner, or fragment thereof in such a form or in such a way that a sufficient affinity is achieved. A multimeric agent having an Aegyptin, hybrid, or binding partner or fragment thereof is obtained by joining the desired polypeptide to a macromolecular support. A "support" can be a termed a carrier, a protein, a resin, a cell membrane, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. An Aegyptin, hybrid, or binding partner or fragment thereof can also be joined to inorganic carriers, such as silicon oxide material (e.g., silica gel, zeolite, diatomaceous earth or aminated glass) by, for example, a covalent linkage through a hydroxy, carboxy or amino group and a reactive group on the carrier.

In several multimeric agents, the macromolecular support has a hydrophobic surface that interacts with a portion of the Aegyptin, hybrid, or binding partner or fragment thereof by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, an Aegyptin, hybrid, or binding partner or fragment thereof can be covalently bound to carriers including proteins and oligo/polysaccharides (e.g. cellulose, starch, glycogen, chitosane or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the Aegyptin, hybrid, or binding partner or fragment thereof. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

Additionally, a cell based approach can be used characterize new Aegyptin family members or Aegyptin hybrids or to rapidly identify binding partners that interact with an Aegyptin and, thereby, modulate fibrinolysis. Preferably, molecules identified in the support-bound Aegyptin assay described above are used in the cell based approach, however, randomly generated compounds can also be used.

Other Aegyptin characterization assays take advantage of techniques in molecular biology that are employed to discover protein:protein interactions. One method that detects protein-protein interactions in vivo, the two-hybrid system, is described in detail for illustration only and not by way of limitation. Other similar assays that can be adapted to identify binding partners include:
(1) the two-hybrid systems (Field & Song, *Nature* 340: 245-246 (1989); Chien et al., *Proc. Natl. Acad. Sci. USA* 88:9578-9582 (1991); and Young K H, *Biol. Reprod.* 58:302-311 (1998), all references herein expressly incorporated by reference);
(2) reverse two-hybrid system (Leanna & Hannink, *Nucl. Acid Res.* 24:3341-3347 (1996), herein incorporated by reference);
(3) repressed transactivator system (Sadowski et al., U.S. Pat. No. 5,885,779), herein incorporated by reference);
(4) phage display (Lowman H B, *Annu. Rev. Biophys. Biomol. Struct.* 26:401-424 (1997), herein incorporated by reference); and
(5) GST/HIS pull down assays, mutant operators (Granger et al., WO 98/01879) and the like (See also Mathis G., *Clin. Chem.* 41:139-147 (1995); Lam K. S. *Anticancer Drug Res.*, 12:145-167 (1997); and Phizicky et al., *Microbiol. Rev.* 59:94-123 (1995), all references herein expressly incorporated by reference).

An adaptation of the system described by Chien et al., 1991, Proc. Natl. Acad. Sci. USA, 88:9578-9582, herein incorporated by reference), which is commercially available from Clontech (Palo Alto, Calif.) is as follows. Plasmids are constructed that encode two hybrid proteins: one plasmid consists of nucleotides encoding the DNA-binding domain of a transcription activator protein fused to a nucleotide sequence encoding an Aegyptin or fragment thereof, and the other plasmid consists of nucleotides encoding the transcription activator protein's activation domain fused to a cDNA encoding an unknown protein that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, Aegyptins can be used as the bait gene product. Total genomic or cDNA sequences are fused to the DNA encoding an activation domain. This library and a plasmid encoding a hybrid of a bait gene encoding the Aegyptin product (Aegyptin) fused to the DNA-binding domain are cotransformed into a yeast reporter strain, and the resulting transformants are screened for those that express the reporter gene. For example, and not by way of limitation, a bait gene sequence encoding an Aegyptin can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait Aegyptin are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait Aegyptin gene-GAL4 fusion plasmid into a yeast strain which contains a lacZ gene driven by a promoter which contains GAL4 activation sequence. A cDNA encoded protein, fused to GAL4 transcriptional activation domain, which interacts with bait Aegyptin gene product will reconstitute an active GAL4 protein and thereby drive expression of the lacZ gene. Colonies that express lacZ can be detected and the cDNA can then be purified from these strains, and used to produce and isolate the binding partner by techniques routinely practiced in the art. In the section below, several diagnostic embodiments are described.

Pharmaceutical Preparations and Methods of Administration

The Aegyptins, hybrids, binding agents, and fragments thereof are suitable for incorporation into pharmaceuticals that treat organisms in need of a compound that modulates platelet adhesion, activation and aggregation. These pharmacologically active compounds can be processed in accordance with conventional methods of galenic pharmacy to produce medicinal agents for administration to organisms, e.g., plants, insects, mold, yeast, animals, and mammals including humans. The active ingredients can be incorporated into a pharmaceutical product with and without modification. Further, the manufacture of pharmaceuticals or therapeutic agents that deliver the pharmacologically active compounds of this invention by several routes are aspects of the invention. For example, and not by way of limitation, DNA, RNA, and viral vectors having sequence encoding the Aegyptins, hybrids, binding partners, or fragments thereof are used with embodiments. Nucleic acids encoding Aegyptins, hybrids, binding partners, or fragments thereof can be administered alone or in combination with other active ingredients.

The compounds described herein can be employed in admixture with conventional excipients, i.e., pharmaceutically acceptable organic or inorganic carrier substances suitable for parenteral, enteral (e.g., oral) or topical application that do not deleteriously react with the pharmacologically active ingredients of this invention. Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable vehicles are described in *Remmington's* Pharmaceutical Sciences, 15th Edition, Easton:Mack Publishing Company, pages 1405-1412 and 1461-1487(1975) and The National *Formulary* XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular pharmaceutical formulation having Aegyptins, hybrids, binding partners, or fragments thereof can vary based on the individual needs of the patient and the treatment or preventative measure sought. Therapeutic efficacy and toxicity of such compounds can be determined by standard pharmaceutical procedures in cell cultures or experimental animals, e.g., ED50 (the dose therapeutically effective in 50% of the population). For example, the Aegyptins, hybrids, binding partners, or fragments thereof discussed above, can be administered to the knockout mice of the invention and the effect on platelet adhesion, activation and aggregation can be determined. The data obtained from these assays is then used in formulating a range of dosage for use with other organisms, including humans. The dosage of such compounds lies preferably within a range of circulating concentrations that include the ED50 with no toxicity. The dosage varies within this range depending upon type of Aegyptin, hybrid, binding partner, or fragment thereof, the dosage form employed, sensitivity of the organism, and the route of administration.

Normal dosage amounts of various Aegyptins, hybrids, binding partners, or fragments thereof can vary from approximately 1 to 100,000 micrograms, up to a total dose of about 10 grams, depending upon the route of administration. Desirable dosages include 250 µg, 500 µg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g.

In some embodiments, the dose of Aegyptins, hybrids, binding partners, or fragments thereof preferably produces a tissue or blood concentration or both from approximately 0.1 µM to 500 mM. Desirable doses produce a tissue or blood concentration or both of about 1 to 800 µM. Preferable doses produce a tissue or blood concentration of greater than about 10 µM to about 500 µM. Preferable doses are, for example, the amount of Aegyptins, hybrids, binding partners, or fragments thereof required to achieve a tissue or blood concentration or both of 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 110 µM, 120 µM, 130 µM, 140 µM, 145 µM, 150 µM, 160 µM, 170 µM, 180 µM, 190 µM, 200 µM, 220 µM, 240 µM, 250 µM, 260 µM, 280 µM, 304 µM, 320 µM, 340 µM, 360 µM, 380 µM, 400 µM, 420 µM, 440 µM, 460 µM, 480 µM, and 500 µM. Although doses that produce a tissue concentration of greater than 800 µM are not preferred, they can be used with some embodiments of the invention. A constant infusion of the Aegyptins, hybrids, binding partners, or fragments thereof can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease, age of the organism, and weight or size of the organism; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the pharmaceuticals of the invention include, but are not limited to, topical, intranasal, transdermal, parenteral, gastrointestinal, transbronchial, and transalveolar. Transdermal administration is accomplished by application of a cream, rinse, gel, etc. capable of allowing the pharmacologically active compounds to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the pharmacologically active compounds of this invention that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein incorporated by reference.

Compositions having the pharmacologically active compounds of this invention that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having the pharmacologically active compounds of this invention that are suitable for transbronchial and transalveolar administration include, but not limited to, various types of aerosols for inhalation. Devices suitable for transbronchial and transalveolar administration of these are also embodiments. Such devices include, but are not limited to, atomizers, vaporizers, and nasal sprays. Many forms of currently available atomizers and vaporizers can be readily adapted to deliver compositions having the pharmacologically active compounds of the invention.

Compositions having the pharmacologically active compounds of this invention that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment.

Compositions having the pharmacologically active compounds of this invention may be administered by parenteral administration including, but not limited to, electrical or direct injection. Accordingly, nucleic acids encoding Aegyptin or fragments thereof, and preferably codon-optimized nucleic acids or fragments thereof to optimize expression in a suitable host (e.g., human, horse, dog, cat, pig, chicken or rodent), can be administered by electroporation or direct injection. Suitable systems for delivery of the above-described nucleic acids include electroporation systems such as the MEDPULSAR® electroporation therapy system, microneedle injection devices, and powder injection (ballistic gene transfer) devices, which are commercially available.

Once the pharmaceutical comprising the Aegyptin, hybrid, binding partner, or fragment thereof has been obtained, it can be administered to an organism in need to treat or prevent a defect in platelet adhesion, activation and aggregation.

Vaccine Compositions

Various nucleic acid-based vaccine therapeutics are known and it is contemplated that these compositions and approaches to immunotherapy can be used in a number of animals. By one approach, for example, a gene encoding one of the Aegyptin proteins can be optimized for expression in a particular animal (e.g., domestic animals, such as dogs, cats, or horses, or humans (see Example 12). By one approach, SEQ ID NO.: 1 is cloned into an expression vector capable of expressing the polypeptide when introduced into a subject. The expression construct is introduced into the subject in a mixture of an adjuvant. For example, the adjuvant is administered shortly after the expression construct at the same site. Alternatively, RNA encoding the Aegyptin polypeptide antigen of interest is provided to the subject in a mixture with ribavirin or in conjunction with an adjuvant.

Where the antigen is to be DNA (e.g., preparation of a DNA vaccine composition), suitable promoters include Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine and human metalothionein can be used. Examples of polyadenylation signals useful with some embodiments, especially in the production of a genetic vaccine for humans, include but are not limited to, SV40 polyadenylation signals and LTR polyadenylation signals. In particular, the SV40 polyadenylation signal, which is in pCEP4 plasmid (Invitrogen, San Diego Calif.), referred to as the SV40 polyadenylation signal, is used.

Delivery of said DNA vaccines, preferably codon-optimized DNA vaccines for optimized expression in a suitable host (e.g., human, horse, dog, cat, pig, chicken or rodent), can be accomplished using a variety of methods (e.g., MEDPULSAR® electroporation therapy system, microneedle injection devices, and ballistic gene transfer devices, such as powder injection devices), which are commercially available. Constructs comprising Aegyptin nucleic acids or fragments thereof (e.g., SEQ ID NO: 3, codon-optimized for expression in human) can be provided for any one or more of the uses described herein because the host animal can produce the protein from the nucleic acid. Accordingly, treatments such as nucleic acid-based vaccine therapeutics can be accomplished by delivering a construct comprising one or more of the nucleic acids described herein.

In addition to the regulatory elements required for gene expression, other elements may also be included in a gene construct. Such additional elements include enhancers. The enhancer may be selected from the group including but not limited to: human actin, human myosin, human hemoglobin, human muscle creatine and viral enhancers such as those from CMV, RSV and EBV. Gene constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region, which produces high copy episomal replication without integration. All forms of DNA, whether replicating or non-replicating, which do not become integrated into the genome, and which are expressible, can be used. Preferably, the genetic vaccines comprise an adjuvant and a nucleic acid encoding Aegyptin, or a fragment or mutant thereof (SEQ ID NOS: 1 and 3). Example 12 below describes the preparation of a genetic vaccine suitable for use in humans.

Treatment of Platelet Aggregation

Provided herein are methods of treating or inhibiting platelet aggregation in an animal by selecting or identifying an animal in need of treatment or inhibition of platelet aggregation and providing to the animal a therapeutically effective dose of a Aegyptin or fragment thereof or nucleic acid encoding one of these molecules. In certain embodiments, the animal is human. In certain embodiments, the Aegyptin polypeptide is Aegyptin.

Without being limited to a particular theory, Aegyptin can be useful as an antithrombogenic therapy targeting collagen-dependent platelet aggregation by disrupting platetet adhesion, activation and aggregation, as well as a procoagulant activity by limiting the generation of thrombin and assembly of coagulation factors.

Delivery of Aegyptin, preferably codon-optimized nucleic acid for optimized expression in a suitable host (e.g., human, horse, dog, cat, pig, chicken or rodent), can be accomplished using a variety of methods (e.g., MEDPULSAR® electroporation therapy system, microneedle injection devices, and ballistic gene transfer devices, such as powder injection devices), which are commercially available. Constructs comprising Aegyptin nucleic acids or fragments thereof (e.g., SEQ ID NO: 3, codon-optimized for expression in human) can be provided for platelet aggregation therapy because the host animal can produce the protein from the nucleic acid. Accordingly, treatments such as nucleic acid-based therapeutics can be accomplished by delivering a construct comprising one or more of the nucleic acids described herein.

Methods of Reducing Clot Formation

Several embodiments also concern methods of reducing clot formation comprising providing to an animal a therapeutically effective dose of an Aegyptin disclosed herein. In certain embodiments, the animal is human. In certain embodiments, the Aegyptin polypeptide is Aegyptin, fragments or mutants thereof.

In certain embodiments, the method of reducing clot formation can be part of a treatment regimen where an antithrombogenic would be used. Nonlimiting examples include: coronary thrombosis, pulmonary embolism, myocardial infarction, deep vein thrombosis, cerebral thrombosis, unstable angina, disseminated intravascular coagulation (DIC), postoperative fibrinolytic shutdown, or a rapid thrombogenic action which can occur following implantation of a medical device. The compositions provided herein may be used in combination with a variety of compositions that have been reported for use in reducing clot formation, including antithrombogenic agents. Antithrombogenic, as this term is used herein, is intended to encompass essentially any composition or medical device with the ability to inhibit thrombin-catalyzed fibrin clot formation, its ability to inhibit the amidolytic activity of thrombin, or by its ability to cause a substantial reduction in other known measures of the thrombogenic response when compared with a medical device that has not been so treated.

Antithrombogenic agents are well known and readily available to the individual skilled in this art. Examples of antithrombogenic or nonthrombogenic agents and materials suitable for use in combination, mixed with, or co-administered with an Aegyptin-like polypeptide, as described herein, may include or be at least partly comprised of heparin, hirudin, albumin, phospholipids, streptokinase, tissue plasminogen activator (tPA), urokinase (uPA), hydrophilic polymers such as hyaluronic acid, chitosan, methyl cellulose, poly(ethylene oxide), poly(vinyl pyrrolidone), growth factors such as endothelial cell growth factor, epithelial growth factor, osteoblast growth factor, fibroblast growth factor, platelet derived growth factor (PDGF), and angiogenic growth factor, other like compounds, or functionally equivalent variants and/or derivatives thereof. The section below describes several medical devices that incorporate one or more of the embodied molecules described herein.

Delivery of Aegyptin, preferably codon-optimized nucleic acid for optimized expression in a suitable host (e.g., human, horse, dog, cat, pig, chicken or rodent), can be accomplished using a variety of methods (e.g., MEDPULSAR® electroporation therapy system, microneedle injection devices, and ballistic gene transfer devices, such as powder injection devices), which are commercially available. Constructs comprising Aegyptin nucleic acids or fragments thereof (e.g., SEQ ID NO: 3, codon-optimized for expression in human) can be provided for reducing clot formation because the host animal can produce the protein from the nucleic acid. Accordingly, treatments such as nucleic acid-based therapeutics can be accomplished by delivering a construct comprising one or more of the nucleic acids described herein.

Methods of Healing Wounds and Inhibiting Scar Formation

Several embodiments also concern methods of healing wounds and/or inhibiting scar formation comprising providing to an animal a therapeutically effective dose of an Aegyptin disclosed herein. In certain embodiments, the animal is human.

An Aegyptin, such as an Aegyptin polypeptide or nucleic acid, is clinically useful as an agent in wound healing, and thus an inhibitor of scar formation such as excessive or hypertrophic scar formation in the dermis occurring during wound healing, including healing of trauma wounds, surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites.

In one embodiment, wound healing and/or scar inhibiting compositions having the pharmacologically active compounds of this invention, such as Aegyptin polypeptides or nucleic acids, are suitable for transdermal or topical administration as described above. In certain embodiments, the Aegyptin polypeptide is Aegyptin, fragments or mutants thereof.

Methods of Blocking Integrin Cell Receptor Interaction, Preventing Metastasis and/or Inhibiting Angiogenesis Several embodiments also concern methods of blocking integrin cell receptor interaction and/or preventing metastasis comprising providing to a subject a therapeutically effective dose of an Aegyptin disclosed herein. "Preventing metastasis" includes partially or fully preventing metastasis.

Without being bound by theory, an Aegyptin inhibits extracellular surface proteins, such as cellulose, which interact with integrins, which are involved in cellular or tissue proliferation. In addition, without being bound by theory, an Aegyptin acts as an anti-angiogenic agent that may work through a variety of mechanisms including, but not limited to, inhibiting integrin receptors expressed on proliferating endothelial cells. Integrins regulate the cell cycle. These integral membrane proteins are attached to the cellular plasma membrane through a single transmembrane helix.

Integrin plays a role in the attachment of cells to other cells, and also plays a role in the attachment of a cell to the material part of a tissue that is not part of any cell (the extracellular matrix). Besides the attachment role, integrin also plays a role in signal transduction, a process by which a cell transforms one kind of signal or stimulus into another. The signal that the integrin converts comes from the extracellular matrix to the cell.

There are many types of integrin, and many cells have multiple types on their surface. Integrins are of vital importance to all animals and have been found in many animals tested, from sponges to mammals. Integrins have been extensively studied in humans.

An Aegyptin, such as an Aegyptin polypeptide or nucleic acid, is useful in blocking integrin cell receptor interaction, inhibiting the metastasis of proliferative cells or tissues, and inhibiting angiogenesis. Inhibition may occur, for example, as a direct result of administering an Aegyptin, such as an Aegyptin polypeptide or nucleic acid, or antibodies directed to an Aegyptin polypeptides as described elsewhere herein, or indirectly, such as activating the expression of proteins known to inhibit metastasis, for example integrins. Such therapeutic affects of the present invention may be achieved either alone, or in combination with small molecule drugs or adjuvants.

Medical Devices

Medical devices, such as stents, catheters and the like may be treated with Aegyptin alone or in combination with another antithrombogenic agent. The approach by which an antithrombogenic agent is incorporated into or onto some or all of a medical device is not limiting, and may be selected from any of a number of methods available in the art, some illustrative examples of which are described in U.S. Pat. No. 6,528,107, the entirety of which is expressly incorporated by reference herein.

For example, U.S. Pat. No. 5,679,659, assigned to Medtronic Inc., the disclosure of which is incorporated herein by reference, describes a method for making a heparinized medical device. In this method, heparin is reacted with a periodate compound and this mixture is reacted and then applied to immobilized amine groups on a medical device surface. The application to the immobilized amine groups causes a reaction between the aldehyde groups on the heparin and the immobilized amine groups to form a Schiff base. A mild reducing agent is used to stabilize the Schiff base into a secondary amine.

Other methods for providing antithrombogenic surfaces, for example, as described in U.S. Pat. Nos. 5,512,329 and 5,741,551, the disclosures of which are incorporated herein by reference, and other related patents assigned to BSI Corporation, relate to methods for modifying substrate surfaces by bonding molecules, e.g., protein molecules, to substrates through external activation of latent reactive groups carried on the molecules. The latent reactive groups are groups which respond to specific applied external stimuli to undergo active specie generation with resultant covalent bonding to an adjacent support surface. Latent reactive groups are those groups of atoms in a molecule which retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups are generally well known and may be chosen to be responsive to various portions of the electromagnetic spectrum.

In addition to the examples described above, many other antithrombogenic treatment methods are similarly known and available to the skilled individual in the art for use in conjunction with the compositions of this invention, including, but not limited to, methods for providing substrate surfaces with agents such as heparin, e.g., U.S. Pat. Nos. 3,511,684, 3,585,647, 4,254,180, 4,331,697, 4,676,974, 4,526,714, 4,634,762, 4,678,660, 4,678,671 and 5,877,263, phospholipids, e.g., U.S. Pat. No. 5,556,632, chitosan, e.g., U.S. Pat. No. 4,326,532, antithrombogenic polymers, e.g., U.S. Pat. Nos. 4,521,564, 4,600,652 and 4,642,242, and others, e.g., U.S. Pat. Nos. 4,973,493, 4,979,959, 5,263,992, 5,414,075, 5,512,329 and 5,741,551, the disclosures of which are incorporated herein by reference.

EXAMPLE 1

Identification and Cloning of Aegyptin

Aegyptin displays sequence similarity to members of 30-kDa salivary allergens found in salivary glands of blood-sucking arthopods whose function has remained elusive so far.[16-19,21,22] Extensive sequence comparison and phylogenetic analysis have been reported for this family of proteins.[17] FIG. 1A shows a diagram displaying highly acidic N-terminus containing 28 negatively charged amino acids Glu or Asp and 5 Gly-Glu-Glu-Asp-Ala (GEEDA, SEQ ID NO: 7) repeats. The repeats are followed by 19 residues of Glu or Asp and a high content of Gly. The C-terminus is typically basic and display 25 positive amino acids Arg or Lys and 18 negative residues. Overall, Gly, Asp, and Glu content of aegyptin is ≈45%, while Arg and Lys represent 11.5% of the protein, which also displays 4 cysteines.

In order to characterize the function of aegyptin, salivary glands of 20 female mosquitoes (non-blood fed) were dissected. Total RNA was extracted with TRIZOL reagent (Invitrogen, San Diego, Calif.), and specific cDNA was amplified using OneStep RT-PCR kit (Qiagen, Chatsworth, Calif.) and the gene-specific primers Aegyptin-For 5'-AGGCCCATGC-CCGAAGATGAAGAACCAG-3' (SEQ ID NO: 4) and Aegyptin-Rev 5'-TTAGTGGTGGTGGTGGTGGT-GACGTCCTTTGGATGAAA CAC-3' SEQ ID NO: 5). These two primers were designed based on Aegyptin sequence (NCBI accession number gi 94468546, presented herein as the DNA sequence SEQ ID NO: 1 encoding the protein sequence SEQ ID NO: 2) to amplify the DNA fragment encoding the mature protein and a 6× His tag before the stop codon. The PCR-amplified product was cloned into VR2001-TOPO vector (modified version of the VR1020 vector; Vical Incorporated, San Diego, Calif.) and sequence and orientation verified by DNA sequencing. Approximately 1 mg of plasmid DNA (VR2001-Aegyptin construct) was obtained using GeneElute™ HP endotoxin-free plasmid MEGA prep kit (Sigma). The plasmid was purified through a 0.22 µm filter.

The following example describes expression and purification of Aegyptin for further use in studies to characterize its function.

EXAMPLE 2

Expression and Purification of Aegyptin

In an attempt to identify the function of aegyptin, cDNA was cloned in a VR2001 expression vector subsequently used for transfection of 293-F cells as follows. Recombinant protein was produced by transfecting FreeStyle™ 293-F cells (Invitrogen) with 240 µg of purified VR2001-Aegyptin plasmid, following manufacturer's recommendations (Invitrogen). After 72 hours, transfected cell culture was harvested. Supernatant containing the secreted recombinant protein was centrifuged (100×g, 15 minutes), frozen, and stored at −30° C. until use.

Medium containing the secreted recombinant protein was centrifuged and supernatant loaded in a $Ni^{2+}$-column and eluted with a buffer containing increments of imidazole concentration as follows. 293-F cells supernatant containing the recombinant protein was loaded onto a $Ni^{2+}$ column (5 ml bed volume; Amersham Biotech, Piscataway, N.J.) following the manufacturer's directions. Fractions were eluted with 10, 40, and 300 mM imidazole (in 50 mM Tris, 300 mM NaCl, pH 8.0), and the fraction eluted at 300 mM was pooled and concentrated in an Amicon (10 MWMCO) to 1 mL and then loaded onto a size-exclusion column (Superdex 75 HR10/30; Amersham Biotech) using the AKTA purifier system (Amersham Biotech). Proteins were eluted at a flow rate of 0.5 ml/minute in 50 mM Tris, 150 mM NaCl, pH 7.4.

The results of the gel-filtration chromatography are shown in FIG. 1B. Purified Aegyptin was analyzed by NU-PAGE and the gel stained with Coomassie blue. The gel revealed purified Aegyptin as a pure material of ≈30 kDa (FIG. 1B, inset).

Purified recombinant protein was submitted to automated Edman degradation for N-terminal sequencing. The amino terminal obtained by Edman degradation yielded the sequence RPMPEDEEVAEG (SEQ ID NO: 6), which is in agreement with the N-terminus predicted for the mature protein, according to the corresponding cDNA.

Concentration of purified Aegyptin (NCBI accession number gi 94468546, presented herein as SEQ ID NO: 2) was estimated by its absorbance at 280 nm using a NanoDrop ND 1000 spectrophotometer (NanoDrop Technologies, Wilmington, Del.) and corrected according to the molar extinction coefficient $\epsilon_{280\ nm}$=5600 $M^{-1} \cdot cm^{-1}$; $A_{280\ nm/cm}$ (1 mg/mL)=0.220. Other calculated parameters are: $M_r$, 27038.09; pI, 3.96. Prediction of N-linked glycosylation sites was obtained at http://ca.expasy.org/tools.

With purified Aegyptin proteins, functional assays were performed, as set forth in the following examples.

EXAMPLE 3

Characterization of Aegyptin Protein

Because Aegyptin has no significant matches to proteins with known function in the databases, and considering that this protein is female specific[17] and therefore potentially involved with blood-feeding capabilities of the mosquito, screening using anticoagulant assays was initially carried out. A series of experiments demonstrated that Aegyptin does not affect coagulation tests (partial prothrombin time, prothrombin time, and thrombin time), esterolytic activity of purified enzymes (e.g. FXa, FIXa, FXIa, FXIIa, kallikrein), and multimolecular coagulation complex assembly (extrinsic Xase, intrinsic Xnase, and prothrombinase) (data not shown). Preliminary experiments also demonstrated that Aegyptin was without effect on platelet aggregation induced by thrombin, ADP, and thromboxane A2 mimetic (U46619); however, inhibition was observed when collagen was tested as a platelet agonist suggesting that Aegyptin could operate either as a platelet receptor antagonist or as collagen-binding protein.

Therefore, experiments were performed to investigate whether recombinant Aegyptin could directly interact with collagen using Surface Plasmon Reonance (SPR) experiments. Aegyptin was found to bind to soluble collagen I-III, but no interaction was observed with other matrix proteins including laminin, vitronectin, fibronectin, vWf, and fibrinogen (FIG. 1C). It was concluded that recombinant Aegyptin inhibits platelet aggregation because it specifically binds to collagen, thus preventing its interaction with platelets.

Female Swiss Webster mice, 8-12 weeks old, were purchased from the Division of Cancer Treatment, National Cancer Institute, NIH. Mice were maintained in the NIAID Animal Care Facility under pathogen-free conditions. Three mice were anesthetized with 100 µl of 20 mg/ml ketamine HCl (Fort Dodge [IA] Animal Health) and immunized with DNA plasmids intradermally in the right ear using a 29.5-gauge needle. DNA plasmids (1 µg/µl) were injected in 10 µl volume, 3 times at 2-week intervals. Two weeks after the last DNA immunization, sera were collected and stored at −30° C. until use. Western blot was performed using anti-Aegyptin antibodies at 1:200 dilution.

EXAMPLE 4

Identification of Aetyptin as a Secreted Salivary Gland Protein

To determine whether the salivary gland homogenate of Ae. aegypti contains a collagen-binding activity, 100 pairs were sonicated and centrifuged, and supernatant was loaded in a gel-filtration column as described below.

One hundred salivary gland extracts were loaded onto a size-exclusion column (Superdex 75 HR10/30; Amersham Biotech) using the AKTA purifier system (Amersham Biotech). Proteins were eluted at a flow rate of 0.5 ml/minute in HBS-N (10 mM HEPES, pH 7.4, 150 mM NaCl). The active fraction (detected by surface plasmon resonance, see below) containing the collagen-binding protein was further purified by ion-exchange chromatography using a MonoQ column HR 5/5 (Amersham Biotech) Proteins were eluted with a linear gradient of NaCl (0-1M) over 60 minute at a flow rate of 0.5 ml/minute. Eluted proteins were again tested for collagen binding activity as described below.

Figures 1D, 1E:
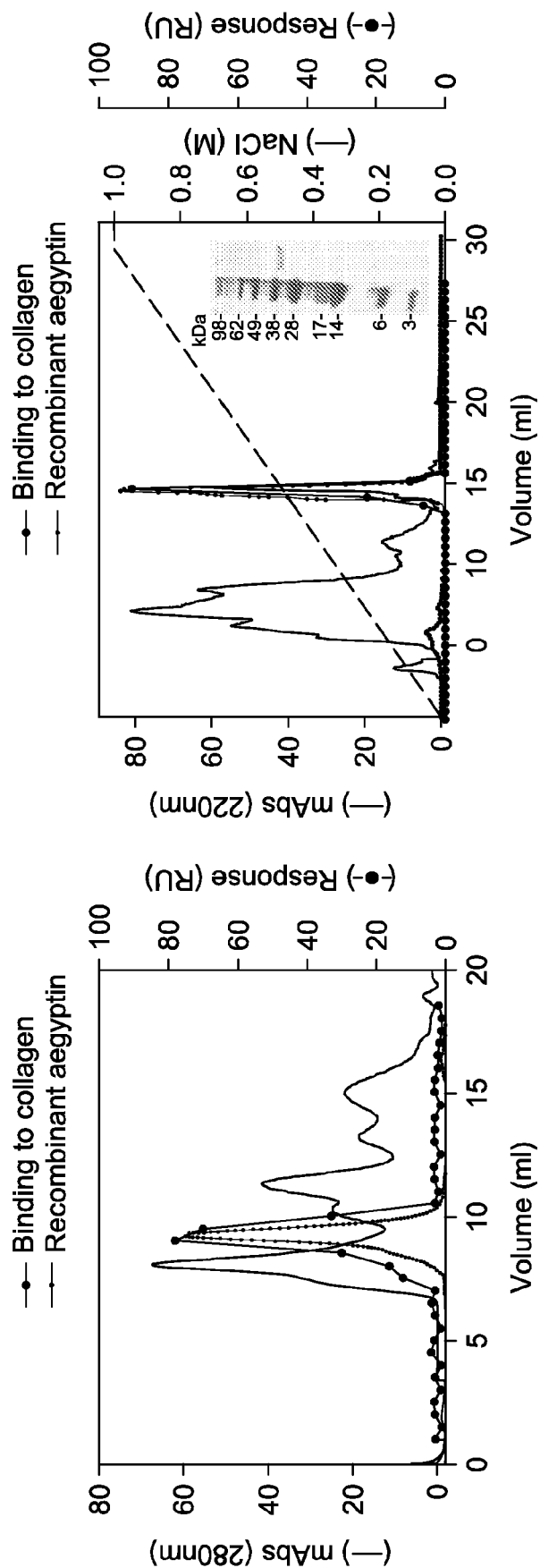

Fractions were tested for collagen-binding activity by SPR and the active fraction found at a retention volume of ≈8.5 ml (FIG. 1D). For comparative purposes, recombinant Aegyptin was applied to the same column and also eluted at ≈8.5 ml retention volume. In an attempt to isolate native Aegyptin from salivary glands, the active fractions obtained above were combined, concentrated, and loaded in an anion-exchange column. The active fraction was eluted at approximately 0.4 M NaCl, which was the same salt concentration needed to elute recombinant Aegyptin (FIG. 1E). In addition, Edman degradation of native Aegyptin present in the active fraction identified three amino acids, Arg, Pro, and Met, which are identical to the N-terminus for the mature protein as predicted by cDNA. Finally, western blot analysis of the salivary gland homogenate using a polyclonal antibody generated by DNA vaccination identified a protein of 30 kDa whose migration pattern is identical to that of recombinant aegyptin. Therefore, it was concluded that Aegyptin is expressed in salivary glands of Ae. aegypti and behaves as a collagen-binding protein. In addition, both recombinant and native inhibitor display identical chromatographic and functional properties. These results validated use of recombinant Aegyptin for further experimentation.

EXAMPLE 5

Platelet Aggregation Assay

Figure 2A:
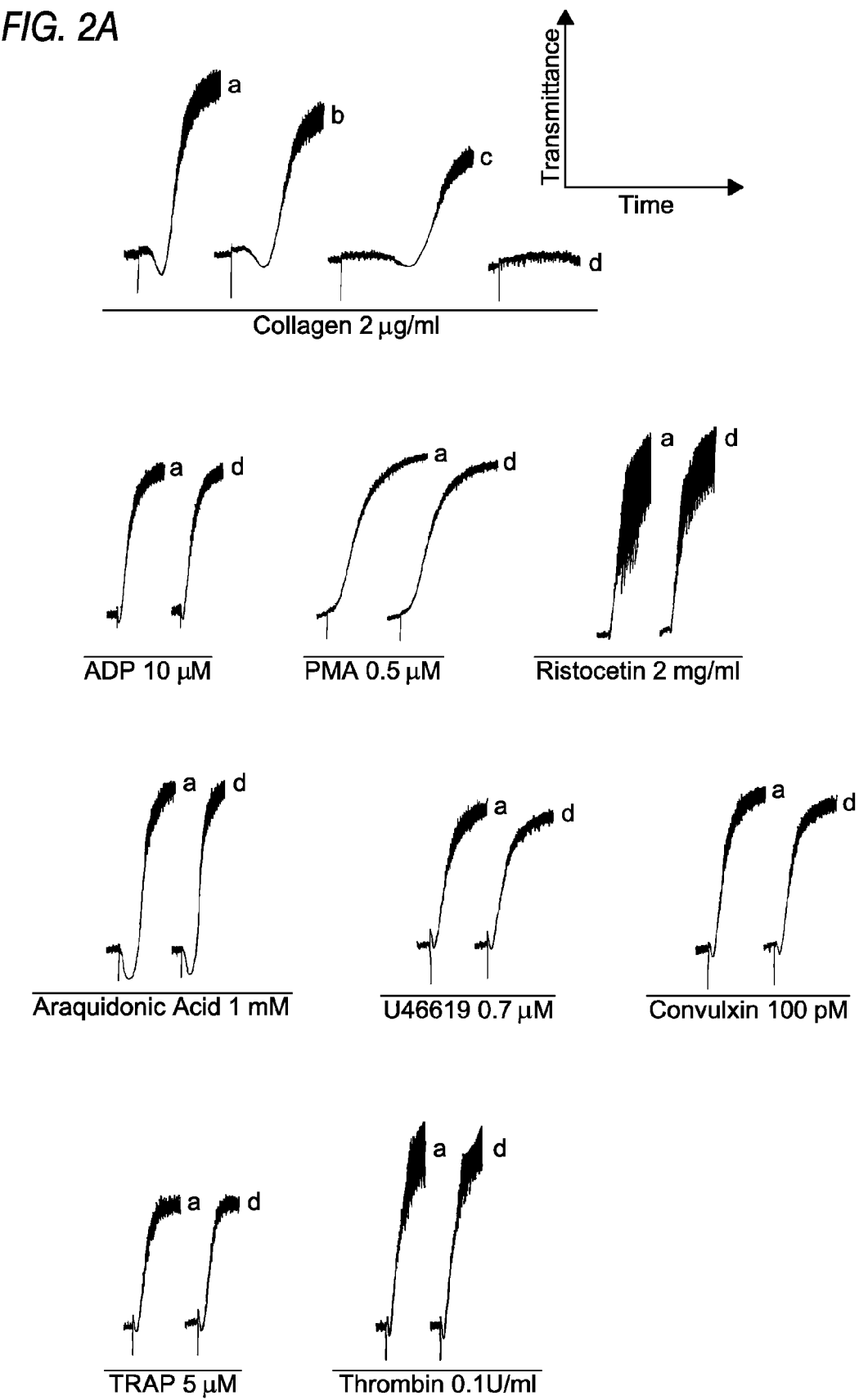
FIGS. 2A-B show platelet aggregation assay data demonstrating that Aegyptin specifically inhibits human platelet aggregation and granule secretion induced by collagen.

The effect of Aegyptin on collagen-induced human platelet aggregation was tested using test-tube stirring conditions as follows. Human platelet-rich plasma ($2 \times 10^5$/ml) was incubated with increasing concentrations of Aegyptin for 1 minute followed by addition of platelet agonists as indicated. Platelet aggregation was estimated by turbidimetry under test-tube stirring conditions. Washed human platelets were used when thrombin was used as an agonist. FIG. 2A shows that Aegyptin inhibits collagen-induced platelet aggregation, but does not inhibit platelet aggregation induced by other agonists ADP, PMA, ristocetin, araquidonic acid, U46619, convulxin, TRAP and thrombin.

Figure 2B:
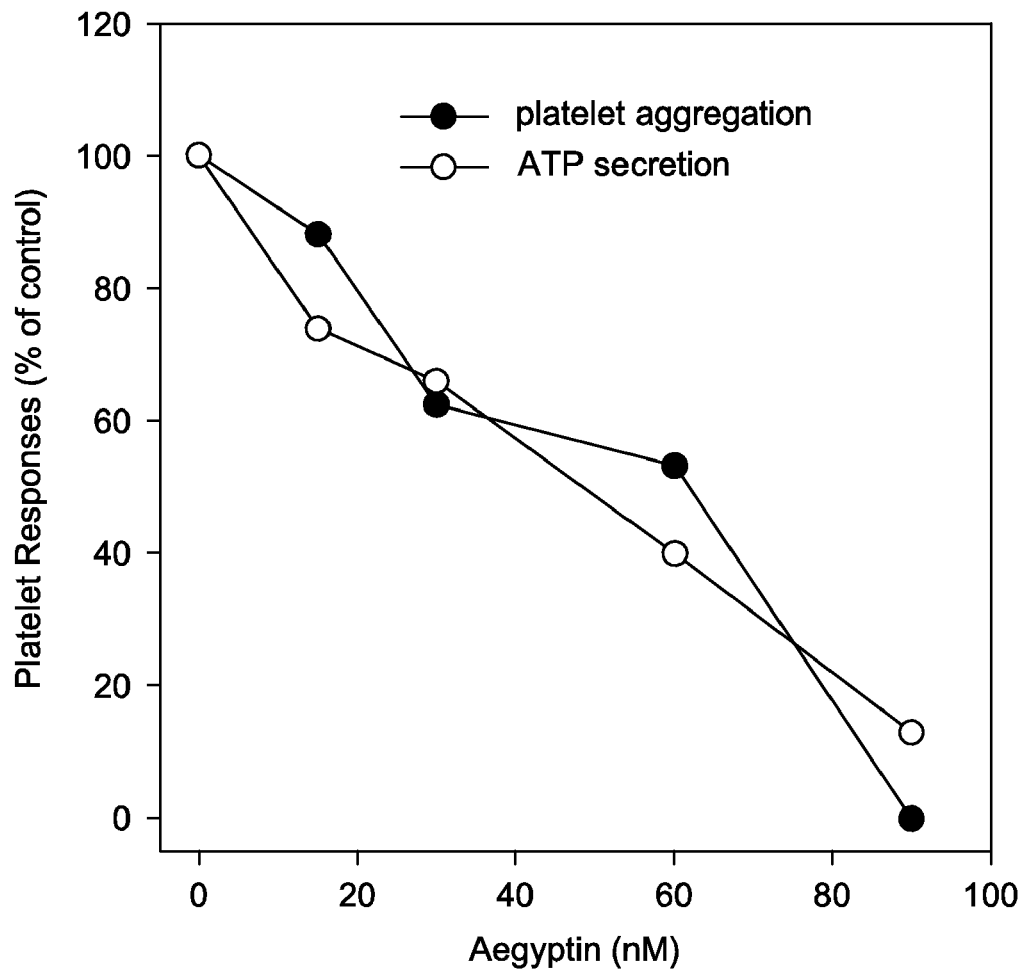

The results show that Aegyptin dose-dependently inhibits onset time for shape change and decreases the extent of platelet aggregation (FIG. 2A) and ATP secretion with an $IC_{50}$ of ≈50 nM (FIG. 2B). Additionally, Aegyptin (300 nM) did not affect platelet aggregation induced by ADP, PMA, ristocetin, araquidonic acid, U46619, convulxin, TRAP, and thrombin (FIG. 2A).

EXAMPLE 6

Aegyptin Displays High-Affinity Binding to Collagens

To investigate binding kinetics of aegyptin-collagen interaction, SPR experiments were performed as follows. All SPR experiments were carried out in a T100 instrument (Biacore Inc., Uppsala, Sweden) following the manufacturer's instructions. This instrument features an integrated degasser, allowing problem-free kinetic measurements at temperatures up to 45° C., as well as a temperature-controlled flow cell and sample compartment. The Biacore T100 evaluation software was utilized for kinetic and thermodynamic evaluation. Sensor CM5, amine coupling reagents, and buffers were also purchased from Biacore Inc (Piscataway, N.J.). HBS-P (10 mM Hepes, pH 7.4, 150 mM NaCl, and 0.005% (v/v) P20 surfactant) was used as the running buffer for all SPR experiments. All SPR experiments were carried out three times.

Immobilization and kinetic analysis. Collagen type I or type III (30 µg/ml) in acetate buffer pH 4.5 was immobilized over a CM5 sensor via amine coupling. The immobilization target was aimed to 1500 resonance units (RU), resulting in a final immobilization of 1737.5 RU for collagen type I and 1613.3 RU for collagen type III. Blank flow cells were used to subtract the buffer effect on sensorgrams. Kinetic experiments were carried out with a contact time of 180 seconds at a flow rate of 30 µl/min at 25° C. Aegyptin-collagen I/III complex dissociation was monitored for 1800 seconds, and the sensor surface was regenerated by a pulse of 20 seconds of 10 mM HCl at 40 µl/minute. Sensorgrams were fitted using the two-state reaction (conformational change) interaction model, and a linked-reactions control experiment was carried out to confirm the multiphase binding kinetics of aegyptin-collagen I interaction.

Figure 3A:
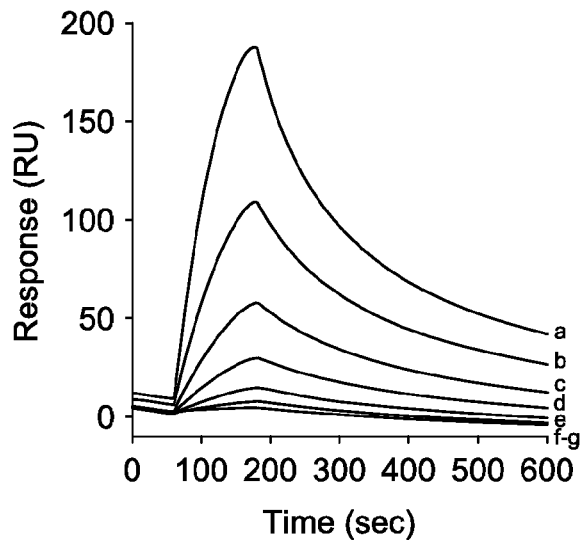
FIGS. 3A-C are sensorgrams showing that Aegyptin binds to collagen I (FIG. 3A) and type III (FIG. 3B). Different concentrations of recombinant Aegyptin (in nM: a, 5; b, 2.5; c, 1.25; d, 0.625; and e, 0.31) were injected over immobilized collagen for 180 seconds. Dissociation of aegyptin-collagen complex was monitored for 1800 seconds, and a global two-state binding model was used to calculate kinetic parameters.
Figure 3B:
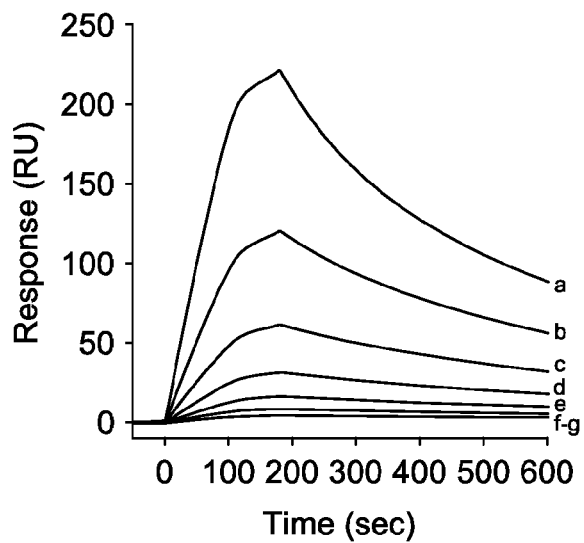

Typical sensorgrams obtained for recombinant Aegyptin interaction with collagen I and III, respectively, are shown in FIGS. 3A and 3B. In both cases, the best fit was attained using a two-state reaction model (Table 1), suggesting that Aegyptin undergoes a conformational change after interaction with collagens. Using this model, Kd of 1.22 nM for collagen type I and Kd of 1.40 nM for collagen III was calculated (Table 1). Aegyptin also binds to soluble collagen types II, IV, and V (data not shown). Next, saliva was collected from *Ae. aegypti* mosquitoes, and the secretion obtained by salivation was used to verify whether it contains collagen-binding properties.

TABLE 1

Kinetics of Aegyptin collagen interaction

|  | Ka1 (1/Ms) | Kd1 (1/s) | Ka2 (1/Ms) | Kd2 (1/s) | KD (nM) | $\chi^2$ |
|---|---|---|---|---|---|---|
| Collagen Type I | 4.237E+6 | 0.015400 | 9.818E−4 | 0.0193 | 1.22 | 1.26 |
| Collagen Type III | 2.490E+6 | 0.006055 | 4.889E−4 | 9.101E−4 | 1.40 | 2.50 |

Identification of collagen-binding protein from salivary gland homogenate and saliva. In some experiments, saliva was used as an analyte. Saliva from female *Ae. aegypti* mosquitoes was collected by oil-induced salivation. An aliquot of 10 µl obtained after size-exclusion or anion-exchange chromatographies were dissolved in 100 µl of HBS-P (10 mM Hepes, pH 7.4, 150 mM NaCl, 0.05% surfactant P-20) and injected over collagen type I and III immobilized on a CM5 sensor chip for 120 seconds at a flow rate of 20 µl/minute. Complex dissociation was monitored for 400 seconds, and the sensor chip surface was regenerated with a 10-second pulse of 10 mM HCl at 30 µl/minute.

Figure 3C:
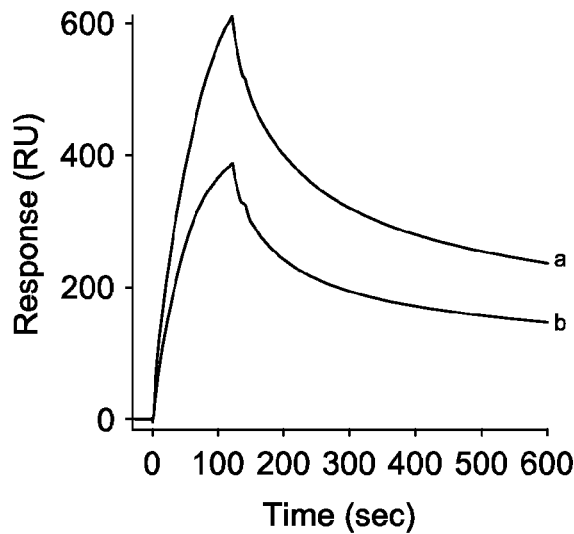

FIG. 3C shows that saliva readily interacts with collagen I (sensorgram a) and III (sensorgram b). Kinetics of interaction were comparable to the pattern obtained with 0.25 nM recombinant Aegyptin (Table 2). Based on these results, it was confirmed that Aegyptin is a protein secreted in the saliva of *Ae. aegyptii* with an estimated concentration of ≈0.2 nM.

TABLE 2

Comparison between *Ae. aegypti* saliva and recombinant aegyptin

|  | Response (RU) | |
|---|---|---|
|  | Collagen type I | Collagen type III |
| Saliva (0.07 µg/ml) | 556.4 | 348.5 |
| Aegyptin (0.25 nM) | 590.3 | 397.9 |

Responses were obtained by injecting saliva or recombinant Aegyptin over immobilized collagen type I and III for 120 sec at a flow rate of 20 µl/min.

EXAMPLE 7

Thermodynamic Analysis of Aegyptin-Collagen I Interaction

Thermodynamic parameters for aegyptin-collagen type I interaction were obtained from independent kinetic experiments using the Thermo Wizard assay program. Briefly, different concentrations of recombinant Aegyptin (0.1 to 3 nM) were injected over immobilized collagen type I at 15° C., 20° C., 25° C., 30° C., 35° C., and 40° C. The sample compartment was kept at 25° C. Contact time, dissociation time, and regeneration of the sensor surface were done as described above. Resulting sensorgrams were fitted to the two-state reaction (conformational change) interaction model with local Rmax. The association (Ka) and dissociation (Kd) rate constants, as well as the affinity constant (KD), were obtained and fitted to a linear form of the van't Hoff and Eyring equations to estimate the ΔH and ΔS as well as $\Delta H^{\circ \ddagger}$ and $\Delta S^{\circ \ddagger}$, respectively.

Affinity and kinetic data (two-state binding model) collected at 5 temperatures (15, 20, 25, 30, 35, and 40° C.) were fitted using Biacore evaluation software to obtain equilibrium and transition-state thermodynamic parameters for the aegyptin-collagen interaction. The van't Hoff plot is linear over a temperature range of 15-40° C., and the calculated free energy difference (ΔG°) of −48±0.013 kJ/mol indicates that the binding reaction occurs spontaneously. Both entropic and enthalpic components of the interaction are favorable, as indicated by a positive value for TΔS° (28±0.83 kJ/mol) and a negative value for ΔH° (−20±0.85 kJ/mol). This suggests that both hydrophobic and hydrogen-bonding interactions contribute significantly to the aegyptin-collagen binding reaction. Table 3 summarizes the results.

TABLE 3

Thermodynamic parameters of Aegyptin interaction with collagen type I

| Parameter name | Value (±SE) |
|---|---|
| ΔH° [kJ/mol] | −20 (0.85) |
| ΔS° [J/(K*mol)] | 95 (2.8) |
| TΔS° [kJ/mol] | 28 (0.83) |
| ΔG° [kJ/mol] | −48 (0.013) |

EXAMPLE 8

Binding Analysis of Effect on GPVI-Collagen Interaction

GPVI plays a crucial role in platelet responses to collagen and directly participates in platelet activation and supports platelet adhesion[23-25] To ascertain whether Aegyptin interferes with GPVI-collagen interaction, GPVI was immobilized in a CM5 chip followed by injection of collagen I in the flow cell, previously incubated with or without inhibitor.

Solution competition assays. Experiments were performed in an attempt to detect whether Aegyptin blocks collagen interaction with GPVI. Recombinant GPVI (25 µg/ml) in acetate pH 4.5 buffer was immobilized on a CM5 sensor with a final surface density of 1753.2 RU. A blank flow cell was used to subtract any effect of buffer in the refractory index change. Then different concentrations (3.175, 6.125, 12.5, 25, and 50 µg/ml) of collagen I alone (control) or previously incubated (15 minutes at room temperature) with 500 nM of Aegyptin in HBS-P buffer was injected over immobilized GPVI for 120 seconds at 20 µl/minute. Complex dissociation was monitored for 400 seconds. Sensor surface was regenerated between runs with by a 30-second pulse of glycine solution, pH 1.5. To verify that immobilized GPVI was still active after all the injection-regeneration cycles, 50 µg/ml of collagen I was injected for 120 seconds at a flow rate of 20 µl/minute and the resulting sensorgram compared with the one obtained before. Additionally, a control experiment was carried out using convulxin at different concentrations (2.5, 5, and 10 nM) incubated with buffer or saturating concentrations of Aegyptin (500 nM) followed by injection of the mixture over immobilized GPVI, as described above.

Figure 4A:
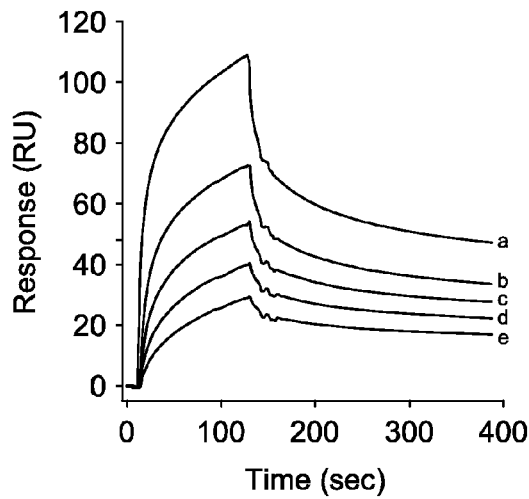
FIGS. 4A-D are sensorgrams showing that Aegyptin inhibits collagen, but not convulxin, interaction with GPVI.
Figure 4B:
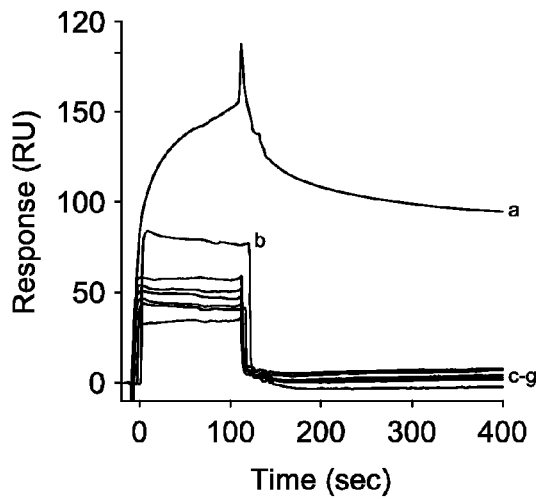
Figure 4C:
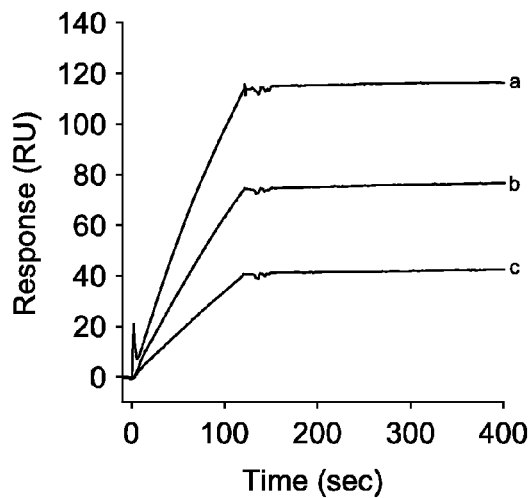
Figure 4D:
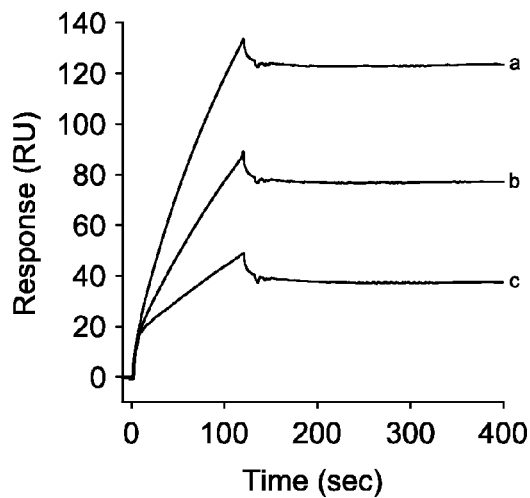

FIG. 4A shows that increasing concentrations of collagen effectively binds to GPVI (sensorgrams a-e). FIG. 4B shows that when collagen I was incubated with buffer (sensorgram a) or increasing concentrations of Aegyptin (sensorgrams c-f), collagen-GPVI interaction was abrogated only in the presence of inhibitor. As a control, sensorgram b shows that Aegyptin alone does not interact with GPVI. Additional control experiments depicted in FIG. 4C demonstrate that convulxin displays high-affinity binding to GPVI (sensorgrams a-c) that was not affected by high concentrations (500 nM) of recombinant Aegyptin (FIG. 4D, sensorgrams a-c).

EXAMPLE 9

Analysis of Effect on Platelet Adhesion to Collagen

Aegyptin Interferes with Platelet Interaction with Collagen I
Integrin α2β1 is known to mediate adhesion in $Mg^{2+}$-dependent manner. It is now recognized that the type of collagen largely determines the requirement for α2β1. Whereas α2β1 is essential for platelet adhesion and activation on monomeric type I collagen in stasis and flow, it is dispensable for these processes on native fibrillar collagen.[42-44] To investigate whether Aegyptin blocks integrin α2β1-collagen interaction, platelets were added to coverslips coated with either fibrillar or soluble collagen.

Platelet Adhesion Assay Under Static Conditions

Coverslips (22×22 mm, no. 0) were treated with $H_2SO_4$: $H_2O_2$ (4:1) for 20 minutes to remove contaminants,[39] followed by ultrasonic washing with deionized water and ultravioletcleaning. Coverslips were coated with fibrillar (100 µg/ml; Chronolog-Par) or soluble collagen type I (100 µg/ml) for 10 minutes, rinsed in deionized water, and incubated overnight with denatured BSA (7 mg/ml). Coverslips were treated with 100 µl of Aegyptin (0-3 µM) for 15 minutes, and inhibitor was removed by inverting and touching the borders of coverslips with precision wipes (Kimberly-Clark, Ontario, Canada). Platelets (200 µl, $2 \times 10^5$/ml) were applied to coverslips, incubated for 45 minutes at room temperature followed by washing in Tyrode-BSA, and mounted for imaging. Differential interference contrast images were obtained with a Leica DMI6000 microscope (Leica Microsystems, Inc., Bannockburn, Ill.) using 100× objective with NA=1.30, and an ORCA ER digital camera (Hamamatsu Photonic Systems, Bridgewater, N.J.). Image acquisition and the digital camera were controlled by ImagePro 5.1 software (Media Cybernetics, Silver Spring, Md.). Extent of platelet adhesion was expressed as percent area covered by platelets.

Figure 5B:
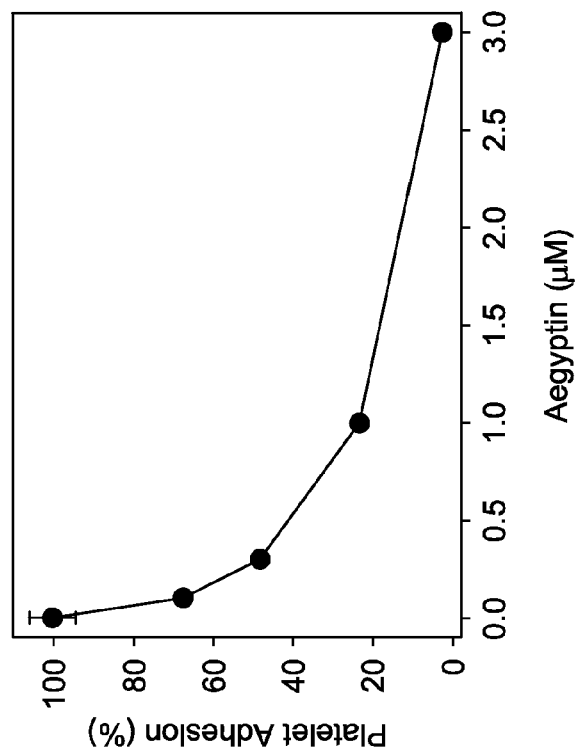
FIGS. 5A-D show that Aegyptin prevents platelet adhesion to fibrillar and soluble collagen under static conditions. Washed human platelets ($2\times10^5$/ml) incubated with (FIG. 5A) fibrillar or (FIG. 5C) soluble collagen for 45 minutes in presence of Aegyptin at various concentrations: a, 0 µM; b, 0.1 µM; c, 0.3 µM; d, 1 µM; and e, 3 µM. In f, coverslips were coated with denatured BSA in absence of collagen.
Figure 5A:
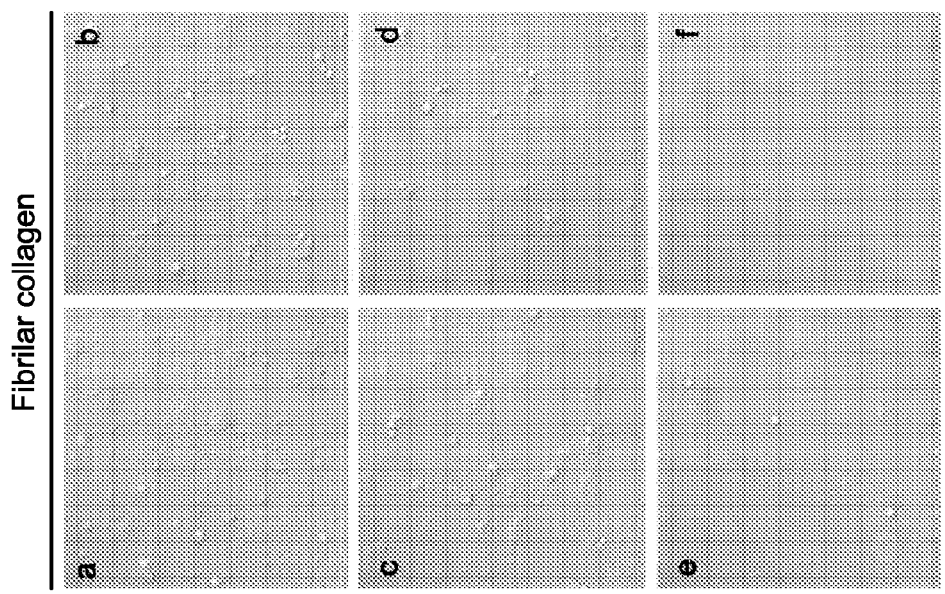
Figure 5D:
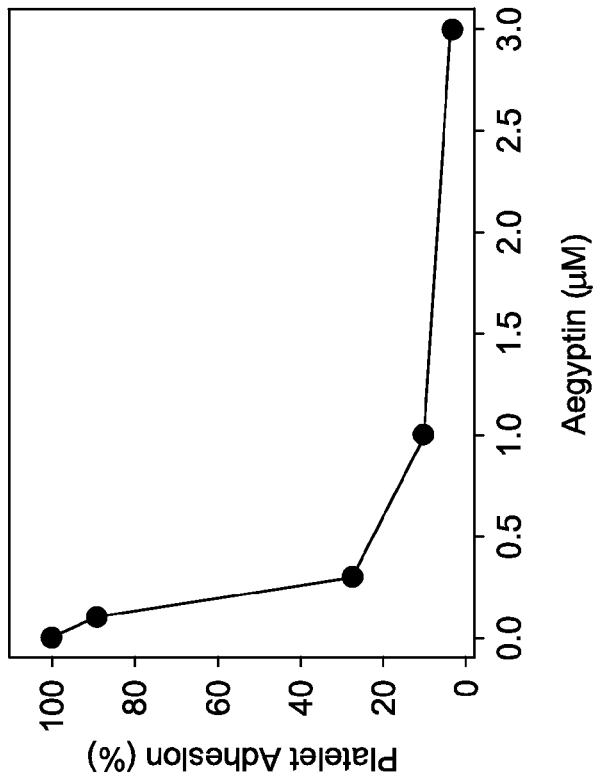
Figure 5C:
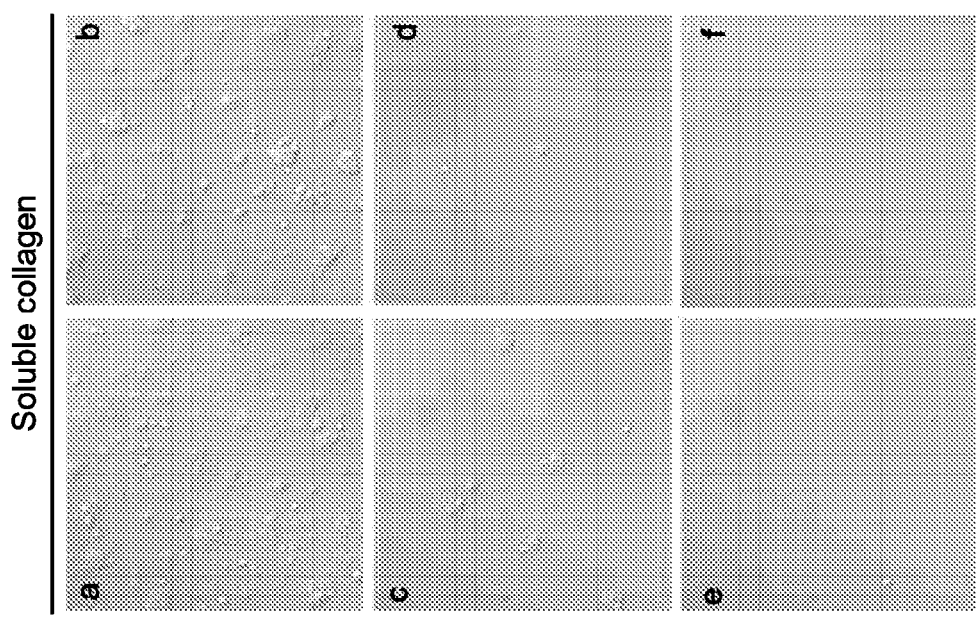

FIG. 5A shows that Aegyptin dose-dependently inhibits platelet deposition to fibrillar collagen ($IC_{50} \approx 250$ nM) (FIG. 5B), while FIG. 5C demonstrates that it prevents platelet adhesion to soluble collagen with an $IC_{50} \approx 200$ nM (FIG. 5D).

EXAMPLE 10

Binding Analysis of Effect of vWf Interaction with Collagen III

Platelet-collagen interactions are believed to have the greatest significance at the medium and high shear rates found in arteries. At the very high shear rates found in small arteries and arterioles, the rapid onset of interaction between GPIb-V-IX and vWf immobilized on collagen is crucial for initial tethering (or capture) of flowing platelets.[23-26] Interaction between vWf and GPIb-IX-V, however, is rapidly reversible and insufficient for stable adhesion. At low shear rates or static condition, vWf plays a secondary role, but interactions can be detected using in vitro assays. In order to determine whether Aegyptin interferes with vWf interaction, the following experiments were performed with collagen III under static and flow conditions.

Figure 6A:
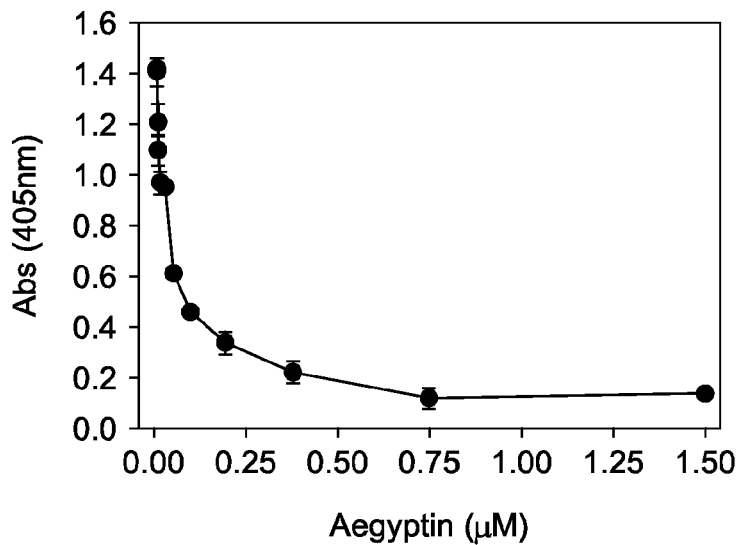
FIGS. 6A-C show that Aegyptin inhibits interaction of vWf with collagen under static and flow conditions.

To estimate the effects of Aegyptin in vWf-collagen interaction, an ELISA assay was optimized as follows. Polystyrene plates were coated with 100 µl of collagen type III (3 µg/ml) or a 2% (w/v) solution of bovine serum albumin (BSA) diluted in PBS for 2 hours at 37° C. After washing twice with PBS to remove unbound protein, residual binding sites were blocked by adding 5 mg/ml denatured BSA overnight at 4° C. After washing 3 times with 50 mM Tris-HCl, 150 mM NaCl, and 0.05% (v/v) Tween 20, pH 7.4 (TBS-T), increasing concentrations of recombinant Aegyptin (ranging from 0.0015 to 1.5 µM) was added to the well and incubated at 37° C. for 1 hour. Wells were washed again and incubated with 3 nM of vWf factor VIII-free (Haematologic Technologies Inc) in TBS-T supplemented with 2% (w/v) BSA. After 1 hour at 37° C., wells were washed 3 times with TBS-T, and a polyclonal rabbit anti-human vWf (DakoCytomation, Glostrup, Denmark) was added (1:500 in TBS-T) and incubated for 1 hour at 37° C. After 3 washes with TBS-T, an alkaline phosphatase conjugate anti-rabbit IgG (whole molecule; Sigma) was added (1:10000) and incubated at 37° C. for 45 minutes. Before adding the stabilized p-nitrophenyl phosphate liquid substrate (Sigma), wells were washed 6 times with TBS-T. After 30 minutes of substrate conversion, the reaction was stopped with 3 N NaOH and absorbance read at 405 nm using a Thermomax microplate reader (Molecular Devices, Sunnyvale, Calif.). Net specific binding was obtained by subtracting optical density values from wells coated only with BSA from the total binding measured as described above. All experiments were performed in triplicate. The results presented in FIG. 6A show that Aegyptin dose-dependently inhibits vWf interaction with soluble collagen III with an $IC_{50}$ of ≈50 nM.

Figure 6B:
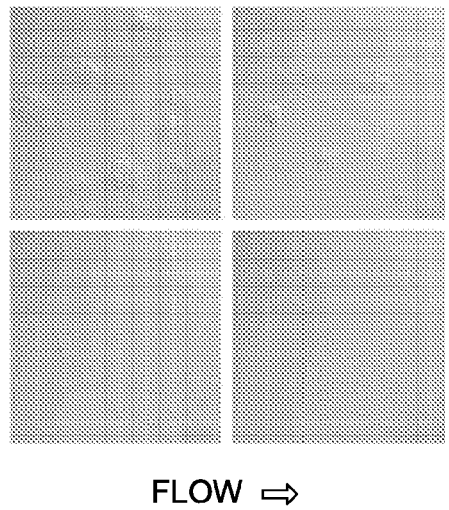
Figure 6C:
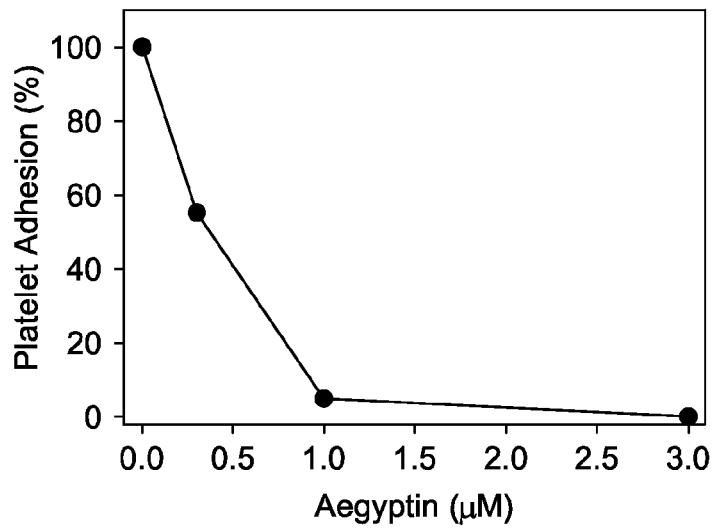

Next, the effects of Aegyptin in platelet adhesion to collagen under flow conditions were evaluated as follows. Glass slides were coated with fibrillar collagen (300 μl, 100 μg/ml) for 10 min, washed in TBS and incubated overnight with denatured BSA (7 mg/ml). Coated slides were treated with Aegyptin (300 μl in Tyrode-BSA; 0-3 μM) for 15 minutes, and excess removed by inversion. The slides was placed in the bottom of the parallel-plate flow chamber (Glycotech, Rockville, Md.), and a silicone rubber gasket determined the flow path height of 254 μm as described[40]. Anticoagulated blood (50 μM PPACK) was mixed with Aegyptin and aspirated using a infusion/withdrawal pump with multi-speed Transmission (Model 940; Harvard Apparatus, Dover, Mass.) through the flow chamber at a flow rate of 0.65 ml/minute, producing a shear rate of $1,500\ s^{-1}$.[40] Blood was perfused for 240 seconds followed by immediate perfusion with Tyrode-BSA (0.65 ml/min) for 120 sec to remove blood, and slides subsequently washed in Tyrode-BSA. Platelet adhesion under flow conditions was recorded using differential interference contrast imaging as described above. Extent of platelet adhesion was expressed as percent area covered by platelets. FIG. 6B demonstrates that Aegyptin dose-dependently inhibits platelet adhesion at shear rates of 1500 s−1; complete blockade was attained at ≈1 μM inhibitor. FIG. 6C shows a dose-response curve with an $IC_{50}$≈300 nM.

Figure 7:
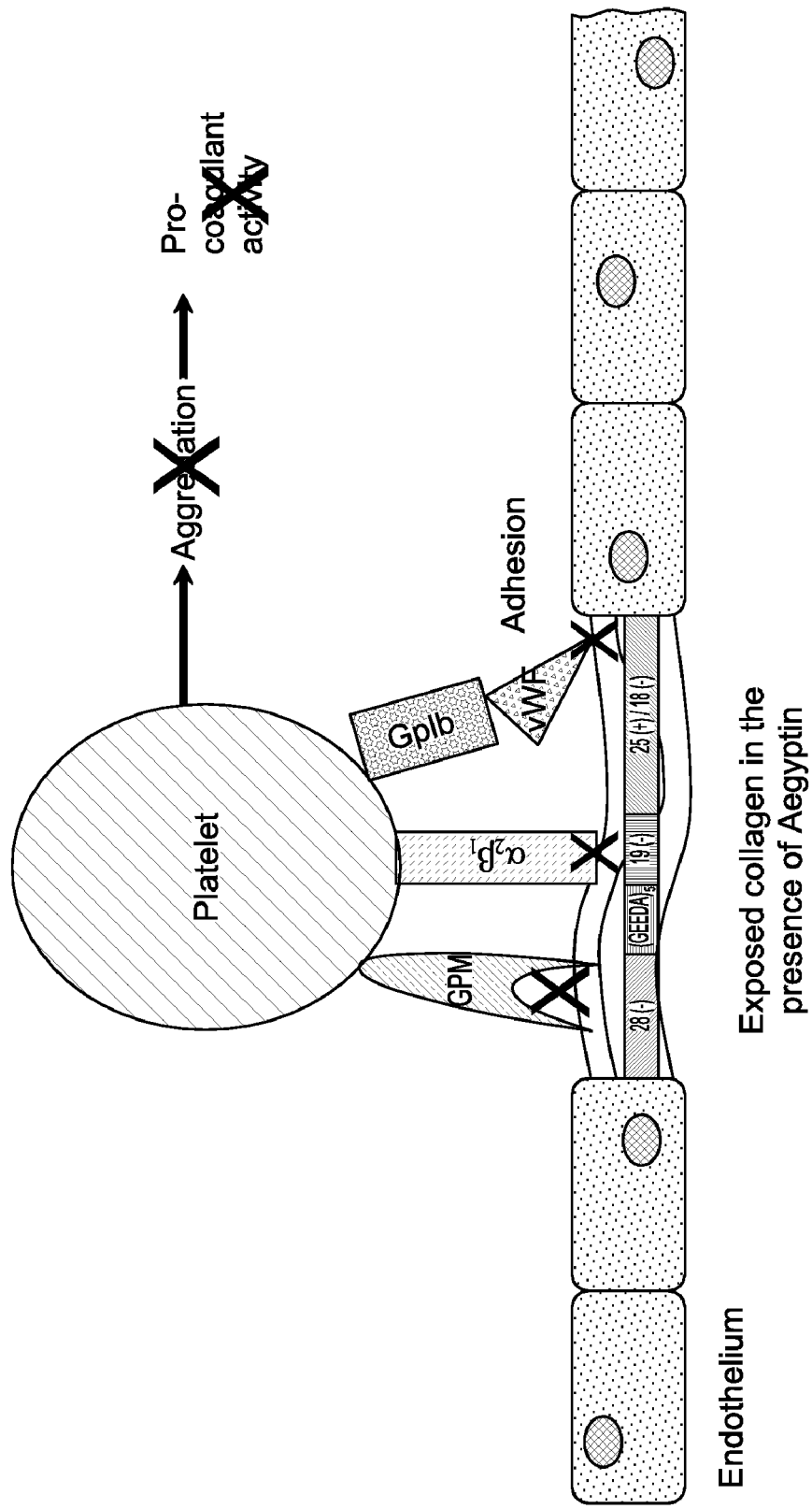
FIG. 7 is a schematic model for Aegyptin-collagen interaction.

FIG. 7 diagrammatically shows the mechanism of platelet inhibition by aegyptin.

EXAMPLE 11

Angiogenesis Inhibition (Aortic Ring) Assay

Aortic Ring Assay

Twelve day old chick eggs are cracked and the embryo is removed from its surroundings. The chick ventral is arranged side up and the head is removed. Tweezers are used to lift the tissue above the breastbone, and scissors are used to trim the tissue above the thoracic cavity to exposure the heart and the aortic arch. The heart and aortic arch are carefully removed and placed in PBS plus 1% Penstrep. Under the dissection microscope, excess tissue is removed, and the clean arches are cut into ~0.8 mm pieces as described in Brassard, D. L., Maxwell, E., Malkowski, M., Nagabhushan, T. L., Kumar, C. C. and Armstrong, L. Integrin alpha(v)beta(3)-mediated activation of apoptosis. Exp Cell Res. 1999; 251:33-45; and Ingber, D. E. 1990. Fibronectin controls capillary endothelial cell growth by modulating cell shape. Proc. Natl. Acad. Sci. USA 87:3579-3583. Because the ends of the aortas are held by forceps during the cleaning and cutting and may become damaged, they are discarded. Plates (96 well) are coated with 3 μl of Matrigel; after gelling, rings are placed into the wells and sealed in place with a 2×10 μl overlay of Matrigel. Then, 100 μl EBM 2 with 1% Pentrep is added, followed by addition of saliva or salivary gland (up to 10 μl). Sprouting is observed for 3 days, and pictures are taken taken using a digital camera coupled to an inverted microscope. Each data point is assayed in triplicate, and each experiment is repeated at least three times. A blinded observer scores outgrowth by comparing responses with media alone (positive control) to that observed with saliva. Results are scored as follows. ++++ (or 100%), sprouting comparable to positive control; +++ (or 75%), significant sprouting but lower than positive control; ++ (or 25%), significant sprouting above background levels; + (or 10%), low levels of sprouting; and ± (<10%), some sprouting above negative control levels.

Aegyptin Inhibits Chick Aorta Ring Sprouting

The sprouting of vessels from aortic ring explants is used next to determine whether the Aegyptin inhibited in vitro angiogenesis. Chick aortic rings are placed in Matrigel and incubated with EBM 2 (100 μl). Aegyptin inhibits sprouting formation.

EXAMPLE 12

Codon Optimization for Expression in Human Cells

The nucleotide sequences encoding the full-length Aegyptin protein was modified to generate sequences optimized for expression in human cells without altering the encoded polypeptide sequences, according to Sharp et al. (1988) Nucleic Acids Res. 16:8207-11, hereby incorporated by reference. The optimized sequence for Aegyptin (SEQ ID NO: 3) bears 74% identity to the original *Ae. aegypti* sequence.

EXAMPLE 13

Aegyptin DNA Vaccines and Therapeutics

An expression plasmid is designed to express aegyptin (SEQ ID NO: 2). The aegyptin coding sequence (SEQ ID NO: 1) is inserted into plasmid A so that it is under the transcriptional control of the CMV promoter and the RSV enhancer element. (See U.S. Pat. No. 6,235,888 to Pachuk, et al., herein expressly incorporated by reference in its entirety). Plasmid Plasmid backbone A is 3969 base pairs in length; it contains a PBR origin of replication for replicating in *E. coli* and a kanamycin resistance gene. Inserts such as aegyptin, are cloned into a polylinker region, which places the insert between and operably linked to the promoter and polyadenylation signal. Transcription of the cloned inserts is under the control of the CMV promoter and the RSV enhancer elements. A polyadenylation signal is provided by the presence of an SV40 polyA signal situated just 3' of the cloning site. An Aegyptin containing vaccine composition is then made by mixing 500 μg of the Aegyptin construct with 1 mg of ribavirin.

Said vaccine composition can be used to raise antibodies in a mammal (e.g., mice or rabbits) or can be injected intramuscularly into a human so as to to raise antibodies. The recipient preferably receives three immunization boosts of the mixture at 4-week intervals, as well. By the third boost, the titer of antibody specific for Aegyptin will be significantly increased.

EXAMPLE 14

In Vivo Clot Lysing Activity

An in vivo experiment is performed in rabbits to demonstrate the dose response of aegyptin either alone or in combination with t-PA. Thrombolytic activities are determined in rabbits using an extracorporeal shunt which contains a thrombus labeled with I-125 fibrinogen. Lysis is measured by the disappearance of radioactivity, measured by an external sodium iodine crystal. Wild type t-PA is given as a 10% bolus with the remainder of the dose infused over the following 90 min. Aegyptin is tested at single dose of 0.1 mg/kg using a 0.05 mg/kg bolus followed by an infusion of 0.05 mg/kg for 90 min. All lysis is determined at the end of the 90 min. infusion.

The results will show that aegyptin has a surprisingly high clot lysing activity, and enhances the clot lysing activity of tPA.

EXAMPLE 15

Treatment of Thrombosis in a Human Patient

Aegyptin may be parenterally administered to subjects suffering from cardiovascular diseases or conditions, including acute thrombosis. Dosage or dose rate may parallel that currently in use in clinical investigations of other cardiovascular, thrombolytic agents, e.g. about 1-2 mg/kg body weight as an intravenous or intra-arterial dose over 1.5-12 hours in patients suffering from conditions, such as myocardial infarction and pulmonary embolism.

EXAMPLE 16

Treatment of a Human Patient Using an Aegyptin-Impregnated Stent

A human patient is diagnosed with cardiovascular disease. During an angioplasty procedure, a drug-eluting mesh stent impregnated with aegyptin and tPA is placed in an occluded artery. The treated artery is monitored periodically after the procedure, and the patient will experience improved cardiovascular health.

Although the invention has been described with reference to embodiments and examples, it should be understood that various modifications can be made without departing from the spirit of the invention. Accordingly, the invention is limited only by the following claims. All references cited herein are hereby expressly incorporated by reference.

EXAMPLE 17

Aegyptin Inhibits Platelet Aggregation by a Novel Mechanism

Recognition of Specific Sequences Involved in Collagen Interaction with Physiological Ligands and Unwinding of the Triple Helix Materials Horse tendon insoluble fibrillar (quaternary, polymeric structure) Horm collagen (Chrono-Log Corp., Haverstown, Pa.) composed of collagen I (95%) and III (5%) was used because this microscopically visible collagen is routinely employed in platelet aggregation studies and in shear-controlled perfusion studies. Pepsin-digested, soluble non-fibrillar (tertiary structure, triple helical) collagen type I-V (BD Biosciences, San Jose, Calif.) was used because it is the collagen of choice to study molecular interactions between human collagen and vWf. ADP, phorbol myristate acetate (PMA) was obtained from Sigma Chemical Co. (St. Louis, Mo.). Ristocetin, arachidonic acid, and Chrono Lumi-reagent were from Chronolog. 9,11-dideoxy-9α,11α-methanoepoxy prostaglandin $F_{2\alpha}$ (U46619) was purchased from Cayman Chemical (Ann Arbor, Mich.), thrombin receptor activating peptide (TRAP) was from EMD (San Diego, Calif.), and thrombin from Haematologic Technologies (Essex Junction, Vt.).

Cloning, Expression and Purification of Aegyptin Domains.

This was performed as described in Examples 1 and 2 above.

Dynamic Light Scattering Plot.

The purity, identity, and solution state of the purified Aegyptin was analyzed using analytical size exclusion chromatography with on-line multi-angle light scattering (SEC-MALS-QELS-HPLC), refractive index (RI) and ultraviolet (UV) detection. The instrument was used as directed by the manufacturer, Waters Corporation (Milford, Mass.) HPLC (model 2695) and photodiodoarray (PDA) detector (model 2996) operated by Waters Corporation Empower™ software connected in series to a Wyatt Technology (Santa Barbara, Calif.) Dawn EOS Light Scattering Detector and Optilab DSP refractive index detector. Wyatt Technology's Astra V software suite was used for data analysis and processing. For separation, a Tosoh Biosciences TSK gel G3000PW×1 column (7.8 mm×30 cm, 6 μm particle size) was used with a TSK gel Guard PW×1 column (6.0 mm×4.0 cm, 12 μm particle size). The column was equilibrated in mobile phase (1.04 mM $KH_2PO_4$, 2.97 mM $Na_2HPO_4.7H_2O$, 308 mM NaCl, 0.5 M urea, pH 7.4, 0.02% sodium azide) for at least 60 min at 0.5 ml/min prior to sample injection. SEC-MALS-HPLC analysis was performed on the Aegyptin using an isocratic elution at 0.5 ml/min in mobile phase. Bio-Rad (Hercules, Calif.) Gel Filtration Standards were run for size comparisons.

Circular Dichroism (CD) of Aegyptin and Collagen in the Presence of Aegyptin

Solutions of Aegyptin, soluble collagen type I and denatured collagen type I (65° C.) were dialyzed against PBS and their concentration adjusted to 3 μM. CD spectra were measured by a Jasco J-715 spectropolarimeter with the solutions in a 0.1-cm path length quartz cuvette in a cell holder thermostated by a Neslab RTE-111 circulating water bath. Spectra were scanned four times, from 330 to 210 nm and averaged (speed 50 nm/min, time constant 1 s). Spectra were obtained at 25° C. To study the effect of Aegyptin on collagen type I, 3 μM (final concentration) of each protein were incubated at room temperature for 15 min before the CD spectrum was measured. After baseline correction, the CD spectra were converted into mean residue ellipticity values using the formula:

$$[theta]=(10 \times mdegs \times MRW)/l.c.100$$

where mdegs is the measured ellipticity, MRW the mean residue weight, l the pathlength (cm) and c the protein concentration (mg/mL).

Atomic Force Microscopy 0.1 mg/ml of collagen (Chronolog) in TBS (50 mM Tris, 150 mM NaCl, pH 7.4) was applied onto the freshly cleaved V-1 grade mica (SPI supplies, West Chester, Pa.), incubated for 10 min, and followed by quick drying by airgun. Micas, with immobilized collagen, were treated with 100 μl of Aegyptin (0.5 μM) for 15 min followed by 3× rinse in TBS to remove the excess of the inhibitor. Micas were dried by airgun. Imaging was performed in ambient condition using Tapping Mode at room temperature at scanning rate of 0.5 Hz with a Multimode AFM, Type J scanner, and Nanoscope IIIa controller (Veeco Instruments, Santa Barbara, Calif.). All images were acquired using silicon TESP probes (Veeco Instruments) with a nominal spring constant of 42 N/m and stored in 512×512 pixel element format and converted to uncompressed TIF formed for further analyses.

Synthesis of Collagen-Related Peptides

Collagen-related peptides (CRP) [(GPO)$_{10}$ (SEQ ID NO: 10), GCO-(GPO)10-GCOG-NH2) (SEQ ID NO: 11)] that recognizes GPVI and the GFOGER peptide (SEQ ID NO: 8), GPC(GPP)5GFOGER(GPP)5GPC) (SEQ ID NO: 12) that recognizes the integrin $\alpha_2\beta_1$ was synthesized by Synbiosci Co. (Livermore, Calif.). The RGQOGVMGFO (SEQ ID NO: 9) peptide, GPC-(GPP)5-GPOGPSGPRGQOGVMGFOGP-KGNDGAO-(GPP)5-GPC-NH2) (SEQ ID NO: 13) that recognizes the vWF binding site was synthesized by Biosynthesis, Inc. (Lewisville, Tex.). All peptides were purified by HPLC and the molecular mass estimated by mass spectrometry: (GPO)$_{10}$ (SEQ ID NO: 10) (mass spectrum, 3294.7 da, theoretical, 3293.6 da); GFOGER (SEQ ID NO: 8) (mass spectrum, 3705.3 da, theoretical, 3704.2 da); RGQOGVMGFO (SEQ ID NO: 9) (mass spectrum, 5573.2 da; theoretical, 5571.27 da).

For cross-linking, the peptides were re-suspended in PBS and incubated at 4° C. for 48 hours, or incubated with SPDP (N-succinimidyl-3-[2-Pyridyldithiol]propionate) reagent from Pierce Co. (Rockford, Ill.), as described (Knight C. G. et al, 1999, Cardiovasc Res 41:450-457). Control experiments show that all peptides were biologically active according to appropriate in vitro assays.

Surface Plasmon Resonance (SPR) Analysis

All SPR experiments were carried out in a T100 instrument (Biacore Inc., Uppsala, Sweden) following the manufacturer's instructions. The Biacore T100 evaluation software was utilized for kinetic analysis. Sensor CM5, amine coupling reagents, and buffers were also purchased from Biacore Inc (Piscataway, N.J.). HBS-P (10 mM Hepes, pH 7.4, 150 mM NaCl, and 0.005% (v/v) P20 surfactant) was used as the running buffer for all SPR experiments. All SPR experiments were carried out three times. Immobilization and kinetic analysis. Soluble collagen I (30 μg/ml) in acetate buffer pH 4.5 was immobilized over a CM5 sensor via amine coupling, resulting in a final immobilization of 1778.5 RU. Peptides were immobilized over a CM5 sensor via amine coupling as recommended by Biacore. The final immobilized levels are as follows: (GPO)$_{10}$ (SEQ ID NO: 10), 662.4 RU; GFOGER (SEQ ID NO: 8), 572.1 RU and RGQOGVMGFO (SEQ ID NO: 9), 534.4 RU. In some experiments, soluble collagen I was heat-denatured for 90 min at 98° C. in a thermocycler and immobilized at 1871.7 RU. Blank flow cells were used to subtract the buffer effect on sensorgrams. Kinetic experiments were carried out with a contact time of 180 s at a flow rate of 30 μl/min at 25° C. Aegyptin-collagen and Aegyptin-peptide complex dissociation was monitored for 1800 s, and the sensor surface was regenerated by a pulse of 20 s of 10 mM HCl at 40 μl/minute. Sensorgrams were fitted using the two-state reaction (conformational change) interaction model, and a linked-reactions control experiment was carried out to confirm the multiphase binding kinetics of Aegyptin-collagen interaction (not shown).

Platelet Preparation

Platelet aggregation and ATP release were performed as described in Example 5 above.

vWf Binding to RGQOGVMGFO Peptide

Polystyrene plates were coated with 100 μl of collagen type III vWf-related peptide (30 μg/ml) or a 2% (w/v) solution of bovine serum albumin (BSA) diluted in PBS for 2 hours at 37° C. After washing twice with PBS to remove unbound protein, residual binding sites were blocked by adding 5 mg/ml denatured BSA overnight at 4° C. After washing 3 times with 50 mM Tris-HCl, 150 mM NaCl, and 0.05% (v/v) Tween 20, pH 7.4 (TBS-T), increasing concentrations of recombinant Aegyptin (ranging from 0.05 to 3 μM) was added to the well and incubated at 37° C. for 1 hour. Wells were washed again and incubated with 3 nM of vWf factor VIII-free (Haematologic Technologies Inc) in TBS-T supplemented with 2% (w/v) BSA. After 1 hour at 37° C., wells were washed 3 times with TBS-T, and a polyclonal rabbit anti-human vWf (DakoCytomation, Glostrup, Denmark) was added (1:500 in TBS-T) and incubated for 1 hour at 37° C. After 3 washes with TBS-T, an alkaline phosphatase conjugate anti-rabbit IgG (whole molecule; Sigma) was added (1:10000) and incubated at 37° C. for 45 minutes. Before adding the stabilized p-nitrophenyl phosphate liquid substrate (Sigma), wells were washed 6 times with TBS-T. After 30 minutes of substrate conversion, the reaction was stopped with 3 N NaOH and absorbance read at 405 nm using a Thermomax microplate reader (Molecular Devices, Sunnyvale, Calif.). Net specific binding was obtained by subtracting optical density values from wells coated only with BSA from the total binding measured as described above. All experiments were performed in triplicate.

Platelet Adhesion Assay Under Static Conditions

Inhibition of platelet adhesion to immobilized collagen or integrin related peptide was examined by fluorometry. Microfluor black microtiter 96-well plate (ThermoLabsystems, Franklin, Mass., USA) was coated with 1 μg of collagen (Chronolog) or 5 μg of GFOGER (SEQ ID NO: 8) overnight at 4° C. in PBS pH 7.2. Wells were washed twice with TBS and then incubated with 2% BSA in Tyrode buffer to block nonspecific binding sites. After 1 h the plate was washed twice with Tyrode buffer. Different concentrations of recombinant Aegyptin in Tyrode buffer were transferred into wells and incubated for 1 h at room temperature. Wells were washed three times with Tyrode buffer and 50 μl calcein-AM labeled platelets were transferred to the well and incubated for 1.5 h at room temperature. After six washes with Tyrode buffer the platelet adhesion was estimated by measuring the fluorescence of the associated cells to the wells using a SpectraMax GeminiXPS fluorimeter (Molecular Devices, Sunnyvale, Calif., USA) with 490/560·nm (excitation/emission) filters.

Binding of Aegyptin-FITC to Fibrillar Collagen.

The fluorescein-EX dye (Molecular Probes) was utilized for labeling of approximately 250 μg of recombinant Aegyptin, following the manufacture's recommendation.

Coverslips (22×22 mm, no. 1.5) were treated with $H_2SO_4$: $H_2O_2$ (4:1) for 20 minutes to remove contaminants, followed by ultrasonic washing with deionized water and ultraviolet cleaning. Coverslips were coated with fibrillar collagen (100 μg/ml; Chronolog-Par) for 10 minutes, rinsed in deionized water, and incubated for 30 min with denaturated BSA (7 mg/ml). Coverslips were treated with 100 μl of Aegyptin-FITC (0.1 μM) for 15 minutes, and inhibitor was removed by inverting and touching the borders of coverslips with precision wipes (Kimberly-Clark, Ontario, Canada) and mounted for imaging. Differential interference contrast (DIC) and fluorescent (488 nm) images were obtained with a Leica DMI6000 microscope (Leica Microsystems, Inc., Bannockburn, Ill.) using 100× objective with NA=1.30, and an ORCA ER digital camera (Hamamatsu Photonic Systems, Bridgewater, N.J.). Image acquisition and the digital camera were controlled by ImagePro 5.1 software (Media Cybernetics, Silver Spring, Md.).

Animals

Adult Wistar rats (males) weighing 200-250 g were housed under controlled conditions of temperature (24±1° C.) and light (12 h light starting at 07:00 am), and all experiments were conducted in accordance with standards of animal care defined by the Institutional Committee.

Photochemically Induced Carotid Artery Thrombosis in Rats

Rats were anesthetized with xylazin (16 mg/kg, intramuscularly) followed by ketamine (100 mg/kg, intramuscularly). The right common carotid artery was isolated through a midline cervical incision, and the blood flow was continuously monitored using a 1PRB Doppler flow probe coupled to a TS420 flowmeter (Transonic Systems, Ithaca, N.Y.) as described (79). Fifteen minutes before induction of thrombosis, animals were injected in the cava vein with Aegyptin (50 or 100 µg/kg) or PBS (control). Thrombosis was induced by slow injection (over 2 min) of 90 mg/kg body weight of rose bengal dye (Fisher Scientific, Pittsburgh, Pa.) into the cava vein at a concentration of 60 mg/ml. Just before injection, a 1.5 mW, 540 nm green light laser (Melles Griot, Carlsbad, Calif.) was applied to the desired site of injury from a distance of 3 cm and remained on for 80 minutes or until stable occlusion occurred (blood flow of 0 ml/min for at least 10 min).

Predictions of Intrinsic Disorder Regions and Three-Dimensional Structure.

Prediction of the intrinsic disorder propensity was performed using PONDR VL-XT (Predictor Of Naturally Disordered Regions), which combines the merger of three predictors, one trained on Variously characterized Long disordered regions and two trained on X-ray characterized Terminal disordered regions (references, see at the end or the document). Three-dimensional structure predictions for Aegyptin were obtained using the algorithm Phyre v 0.2 (protein homology/analogy recognition engine) (see Kelly et al 2000, J. Mol. Biol. 299:499-520).

Statistical analysis-Results are expressed as mean±SEM.

Aegyptin Displays an Elongated Structure

The predicted molecular weight of Aegyptin (mature peptide) predicted by cDNA is 27 kDa (Calvo, E., Andersen, J., Francischetti, I. M., de, L. C. M., deBianchi, A. G., James, A. A., Ribeiro, J. M., and Marinotti, O. 2004. The transcriptome of adult female *Anopheles darlingi* salivary glands. *Insect Mol Biol* 1 3:73-88). However, it elutes as a higher molecular weight protein of 112 kDa (retention time 14.75 min) when loaded on a gel filtration column (FIG. 8A). In an attempt to obtain further insights related to Aegyptin structure, a series of experiments were designed. SEC-MALS-QELS-HPLC was used to analyze the hydrodynamic radius ($R_h$) of the recombinant Aegyptin given the significant increase in the apparent weight average mass. Multi-angle light scattering confirmed its presence as a monomer of 33 kDa (±1.67) (FIG. 8B) with a hydrodynamic radius of 4.8 nm (±0.29), indicating that it is a non-globular protein with a molecular mass of 33.4 kDa. This result also indicates that Aegyptin is highly extended compared to a more typical globular protein such as BSA ($R_h$ 3.4 nm). The CD spectrum shows that Aegyptin contains 50% of α-helices, 20% of β-sheet and 25% unordered structures (FIG. 8C). FIG. 8D depicts a plot using the PONDR VL-XT software which identified that Aegyptin has unordered structures mostly found in the N-terminus of the molecule. The elongated pattern with high contents of α-helix and β-sheet was also predicated by Phyre v 0.2 algorithm (FIG. 8E).

Aegyptin Induces Unwinding of the Collagen Molecule

Figure 9A:
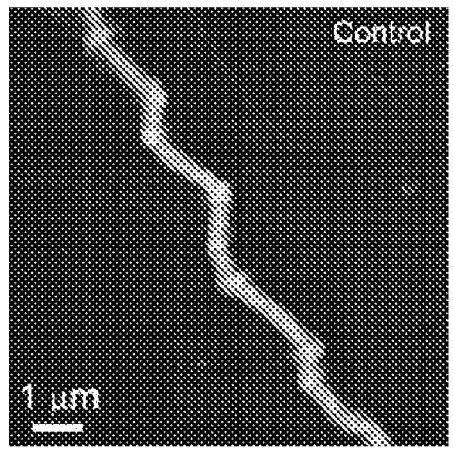
FIGS. 9A-9E show Aegyptin induces unwinding of collagen. Atomic force microscopy of Horm collagen fibrils. (A) control shows collagen fibrils on a freshly cleaved V-1 grade mica. Scale bar, 1 µm. (B) shows collagen incubated with Aegyptin (0.5 µM) displays "birdcaging" ropes which is typical of unwinding of the collagen molecule (23), as indicated by the arrows. (C) and (D) display the surface plot of selected areas of (A) and (B). (E) Circular dichroism of collagen in the presence of Aegyptin. CD spectrum of collagen in the presence of Aegyptin shows that the structural changes by a reduction in poly-proline II structure, resembling the CD spectrum of denatured soluble collagen type I (Coll-I 65° C.-denatured).
Figure 9B:
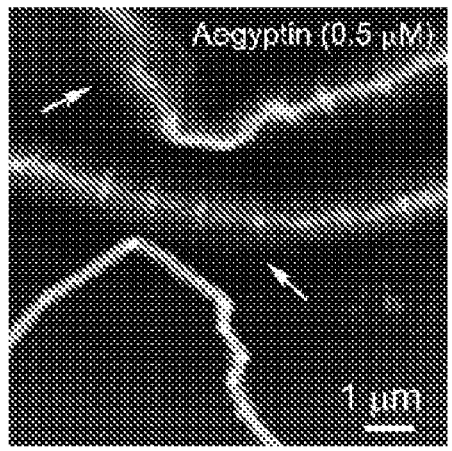
Figure 9C:
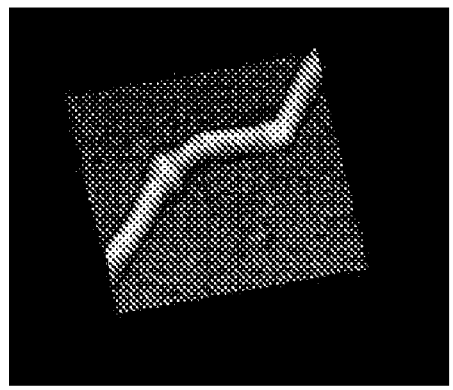
Figure 9D:
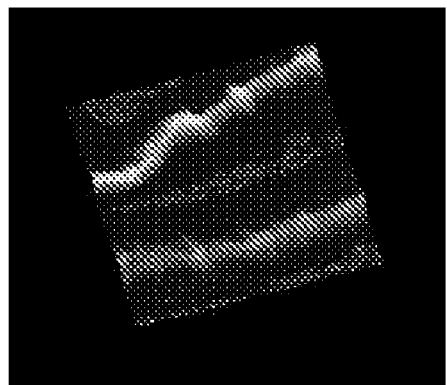
Figure 9E:
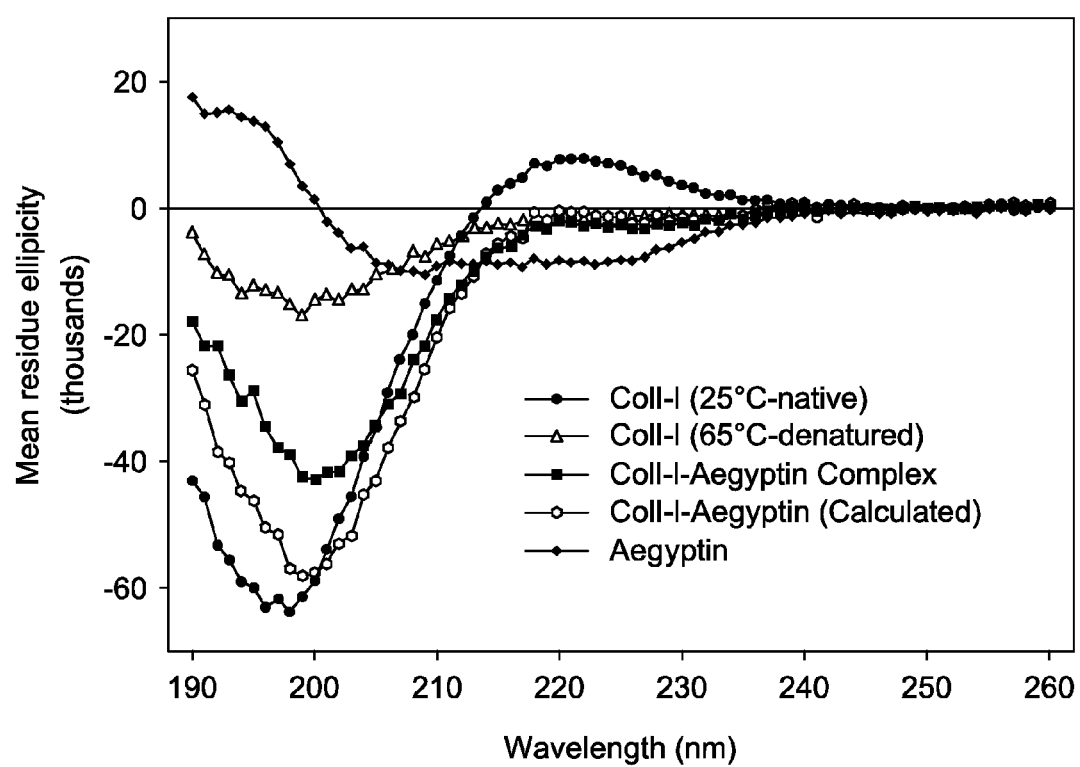

The interaction of Aegyptin with collagen is visualized, using atomic force microscopy (AFM). AFM is particularly useful technique to visualize the morphology of molecules and cells under aqueous environment without fixation, and has previously been used to dissect the structure of collagen. The AFM images of collagen fibrils in FIG. 9A (control) shows D-banding pattern and features characteristic of a rope-like structure. (Bozec, L., van der Heijden, G., and Horton, M. 2007. Collagen fibrils: nanoscale ropes. *Biophys J* 92:70-75) and FIG. 9B (Aegyptin 0.5 µM) depicts the phenomenon of the so-called "birdcaging" of a rope when Aegyptin is present, in which the strands making up the rope separate and open up in the presence of the inhibitor. In the absence of Aegyptin, the apparent average diameter of collagen was calculated as 0.614 nm±0.1 Å, while in the presence of Aegyptin it was of 1.022±0.3 Å. FIGS. 9C and 9D show the surface plot of selected areas of FIGS. 9A and 9B. To confirm that Aegyptin induces unwinding by a second and independent technique, CD spectra of collagen in the presence of Aegyptin were performed and compared with the spectra of heat-denatured collagen. FIG. 9E shows CD spectra of Aegyptin (3 µM) and native collagen type I (3 µM) at 25° C., and the spectrum of the mixture containing Aegyptin and collagen. The calculated spectrum is just the sum of the first two. As expected, there is a sizeable loss of signal in the collagen region, but not at longer wavelengths. FIG. 9E also shows the CD spectra of soluble collagen type I at 65° C. (denatured) where most of the CD signal is lost. Assuming that the change of collagen ellipticity at 200 nm in this figure (44.2 mdegs) shows complete unfolding, then the amount of signal lost in the Aegyptin-collagen-complex (14.9 mdegs), suggests that 34% of the collagen is unfolded in the complex, by reduction in poly-proline II structure, resembling the CD spectrum of denatured collagen.

Aegyptin Interacts with Specific Sequences Involved in Collagen Interaction with GPVI, vWF and Integrin α2β1

Figure 10D:
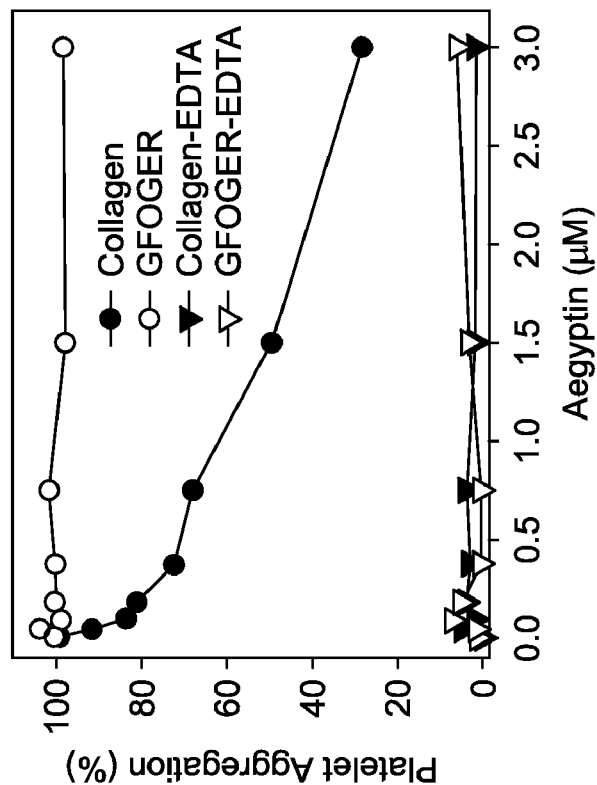
Figure 10C:
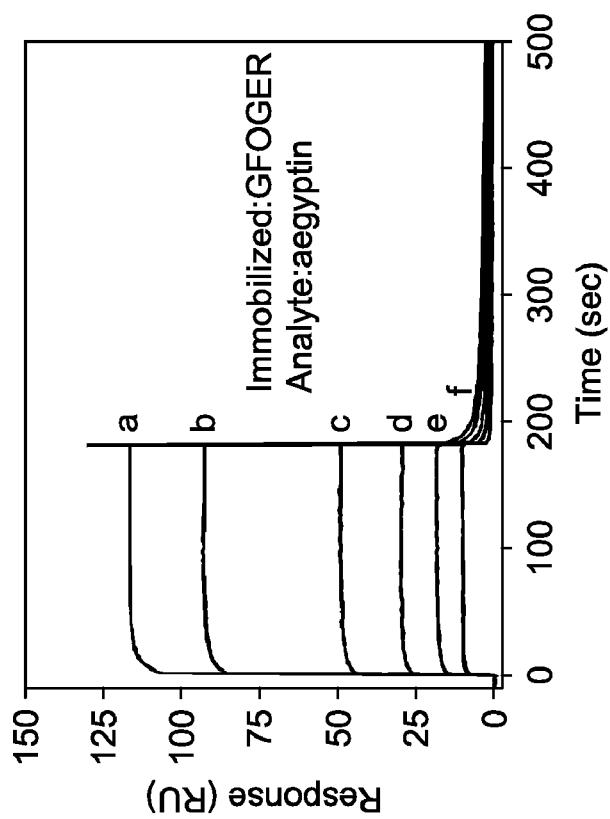
Figures 10E, 10F:
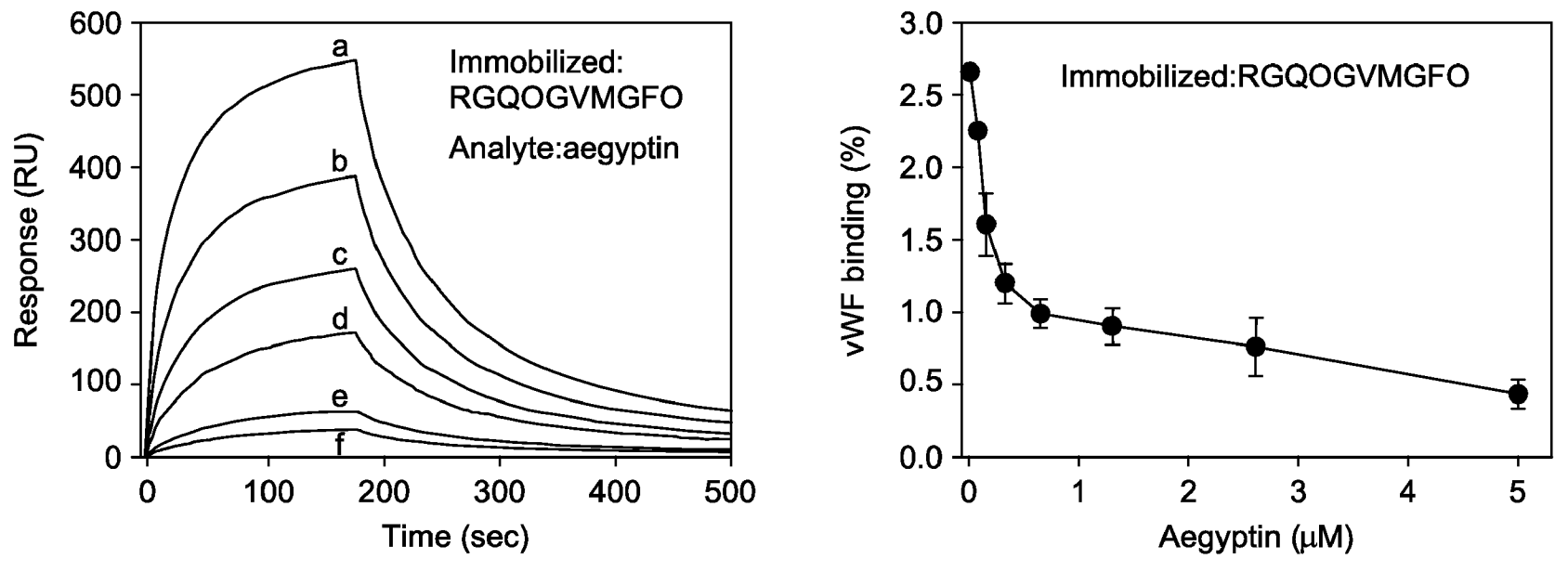

In an attempt to identify the binding sequences involved in collagen interaction with Aegyptin, a series of peptides based on collagen sequences which reportedly mediate collagen interaction with physiological ligands were synthesized. The peptides (GPO)$_{10}$ (SEQ ID NO: 10), GFOGER (SEQ ID NO: 8) and RGQOGVMGFO (SEQ ID NO: 9) were then cross-linked and used for SPR experiments and functional assays in vitro, as described hereinabove. FIG. 10A shows typical sensorgrams of Aegyptin binding to (GPO)$_{10}$. The data was fitted with a two-state binding model and yields a $K_D$ of 5.01 µM. Functionally, Aegyptin prevents collagen-induced platelet aggregation under test-tube stirring conditions with an IC50≈100 nM (see Example 5 above) but was ineffective to inhibit (GPO)$_{10}$-induced platelet aggregation (FIG. 10B), consistent with a low affinity interaction. FIG. 10C demonstrates that Aegyptin recognizes the integrin binding site in collagen with a $K_D$ of 2.4 µM and FIG. 10F shows that Aegyptin prevents platelet adhesion to immobilized collagen in a dose-dependent manner, but was ineffective when GFOGER (SEQ ID NO: 8) was immobilized, due to low affinity. FIG. 10E shows that Aegyptin interacts with RGQOGVMGFO (SEQ ID NO: 9) with a calculated $K_D$ of 0.1 µM while FIG. 10F shows that the inhibitor prevents vWF interaction with the peptide with an IC$_{50}$≈300 nM. Table 4 summarizes the kinetic findings.

TABLE 4

Kinetics of Aegyptin interaction with soluble collagen type I, collagen mimetics and heat-denatured collagen. Responses were obtained by injecting recombinant Aegyptin over immobilized peptides and proteins for 180 s at a flow rate of 30 μl/min.

|  | Ka1 ($M^{-1}s^{-1}$) | Kd1 ($s^{-1}$) | Ka1 ($M^{-1}s^{-1}$) | Kd2 ($s^{-1}$) | $K_D$ | $\chi^2$ |
|---|---|---|---|---|---|---|
| Collagen type I | $3.630 \times 10^6$ | 0.01027 | 0.0016670 | 0.000883 | 0.980 nM | 0.625 |
| $(GPO)_{10}$ | $2.055 \times 10^5$ | 1.1940 | 0.004015 | 0.028880 | 5.101 μM | 0.139 |
| GFOGER | $4.058 \times 10^5$ | 0.9432 | 0.0003662 | 0.002613 | 2.400 μM | 0.800 |
| RGQOGVMGF | $6.191 \times 10^4$ | 0.01299 | 0.0009806 | 0.001937 | 0.139 μM | 11.90 |
| Collagen denatured | $6.742 \times 10^5$ | 0.01876 | 0.002062 | 0.000274 | 3.320 nM | 2.75 |

Aegyptin Exhibits High Affinity Binding to Heat-Denatured Collagen. Aegyptin-FITC Displays Throughout Binding to Collagen.

Figure 10H:
Figure 10G:
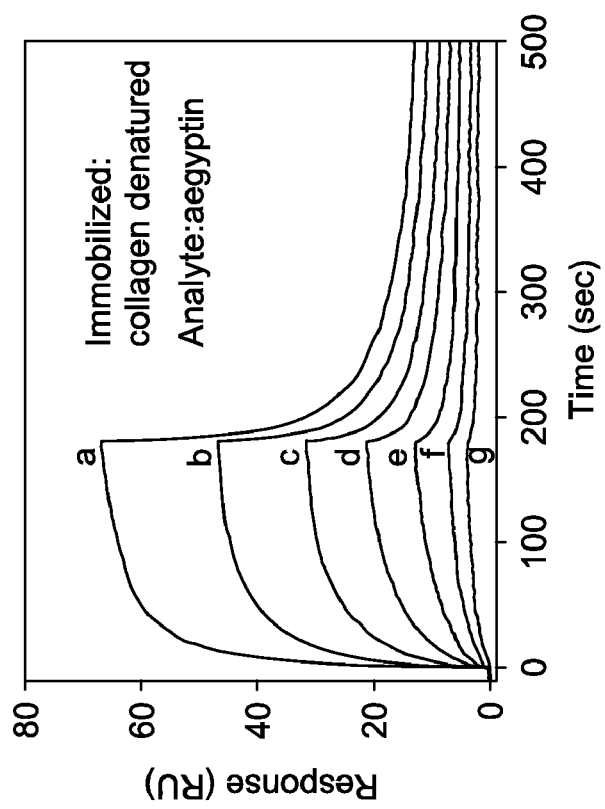

Individual collagen molecules maintain their integrity by non covalent bonds, and denaturation leads to unraveling of the coiled-coil and dissociation of the three chains. Heating the collagens above a critical temperature causes denaturation, reflected in a rapid loss of the triple helical structure. (Khoshnoodi, J., Cartailler, J. P., Alvares, K., Veis, A., and Hudson, B. G. 2006. Molecular recognition in the assembly of collagens: terminal noncollagenous domains are key recognition modules in the formation of triple helical protomers. *J Biol Chem* 281:38117-38121; Heino, J. 2007. The collagen family members as cell adhesion proteins. *Bioessays* 29:1001-1010.) Therefore, experiments were performed to determine whether the triple helical structure of collagen is needed for high affinity binding. FIG. 10G shows that Aegyptin binds to heat-denatured collagen with affinity comparable to the native molecule (Table 4) indicating that the primary sequence is sufficient for the interaction. To determine the pattern of aegytin binding to collagen fiber, Aegyptin was labeled with FITC as described in Methods. FIG. 10B shows the collagen fibers detected by DIC and FIG. 10H demonstrates that Aegyptin-FITC interacts throughout with fibrillar Horm collagen which was confirmed by bright field microscopy observed under DIC (not shown). Specificity was checked using 25× molar excess of unlabeled Aegyptin, and no auto fluorescence was detectable for collagen alone (not shown).

Collagen Behaves as a Tight Ligand to Immobilized Aegyptin

Figure 11A:
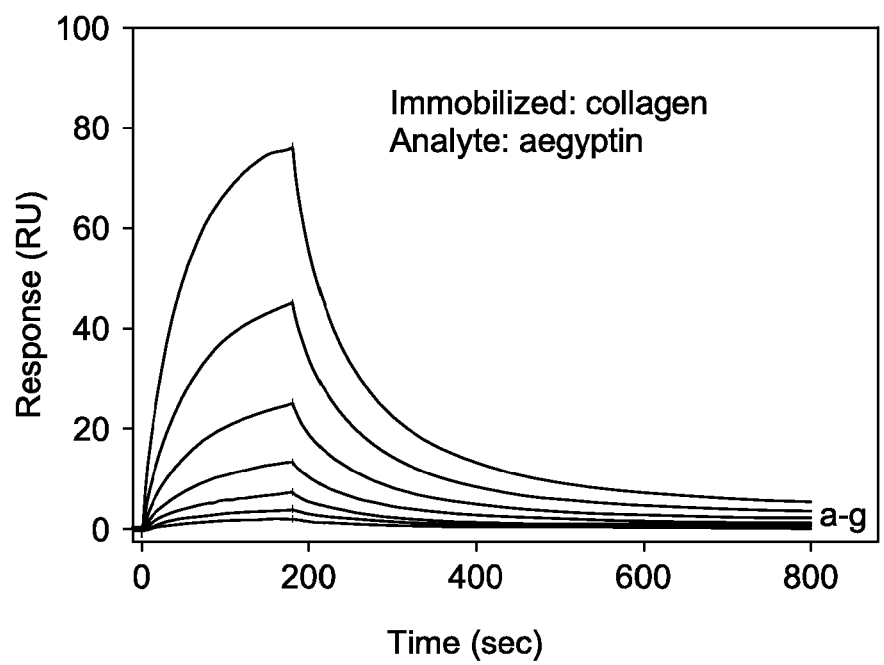
FIGS. 11A-11B show irreversible binding of collagen to immobilized Aegyptin. (A) typical sensograms of Aegyptin-collagen interaction were observed when Aegyptin was injected (in nM: a, 10; b, 5; c, 2.5; d, 1.25; e, 0.6; f, 0.3 and g, 0.15) over immobilized collagen type I. The slow dissociation was described before (20). (B) Collagen behaves as a tight binding partner, showing no dissociation to immobilized Aegyptin over the monitored time (1800 sec). Collagen concentrations (in nM: a, 5; b, 2.5, c, 1.25; d, 0.625; e, 0.3; f, 0.15 and g, 0.075) were randomly injected for 180 sec and the sensor's surface regenerate with 30 sec pulses of 20 mM HCl at 30 µl/min.
Figure 11B:
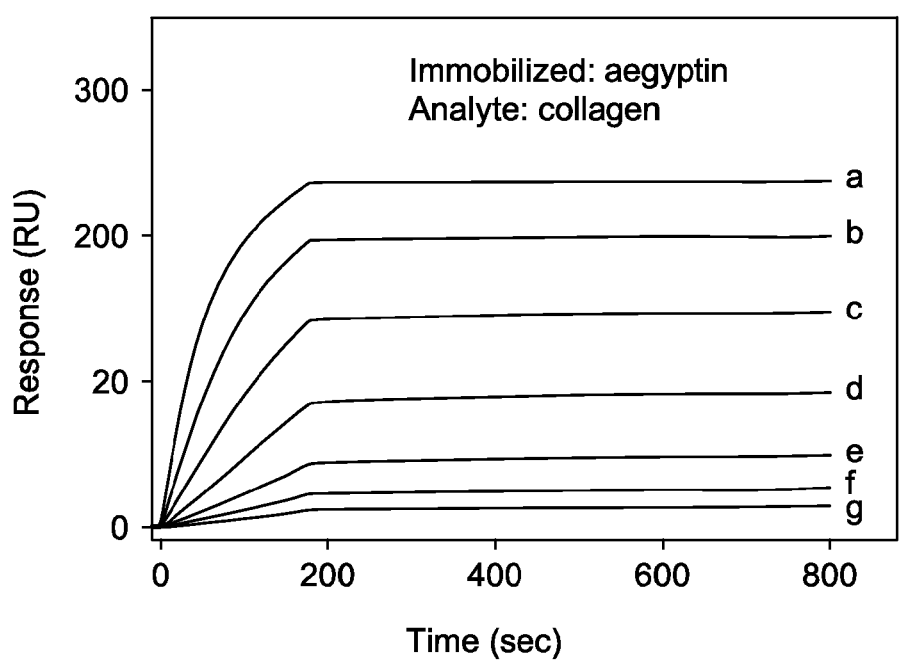

Next, an independent experiment was performed to confirm that Aegyptin interacts with multiple binding sites in collagen. Sensorgrams in FIG. 11A show that Aegyptin binding to immobilized collagen is followed by slow dissociation phase, as described previously (Calvo, E., Tokumasu, F., Marinotti, O., Villeval, J. L., Ribeiro, J. M., and Francischetti, I. M. 2007). Aegyptin, a novel mosquito salivary gland protein, specifically binds to collagen and prevents its interaction with platelet glycoprotein VI, integrin alpha2beta1, and von Willebrand factor. *J Biol Chem* 282:26928-26938). Notably, however, when Aegyptin was immobilized in the sensor chip and collagen used as an analyte, interaction displayed irreversible binding (FIG. 11B, see Discussion below).

Identification of C-Terminal as a Functional Domain of Aegyptin

Figure 12A:
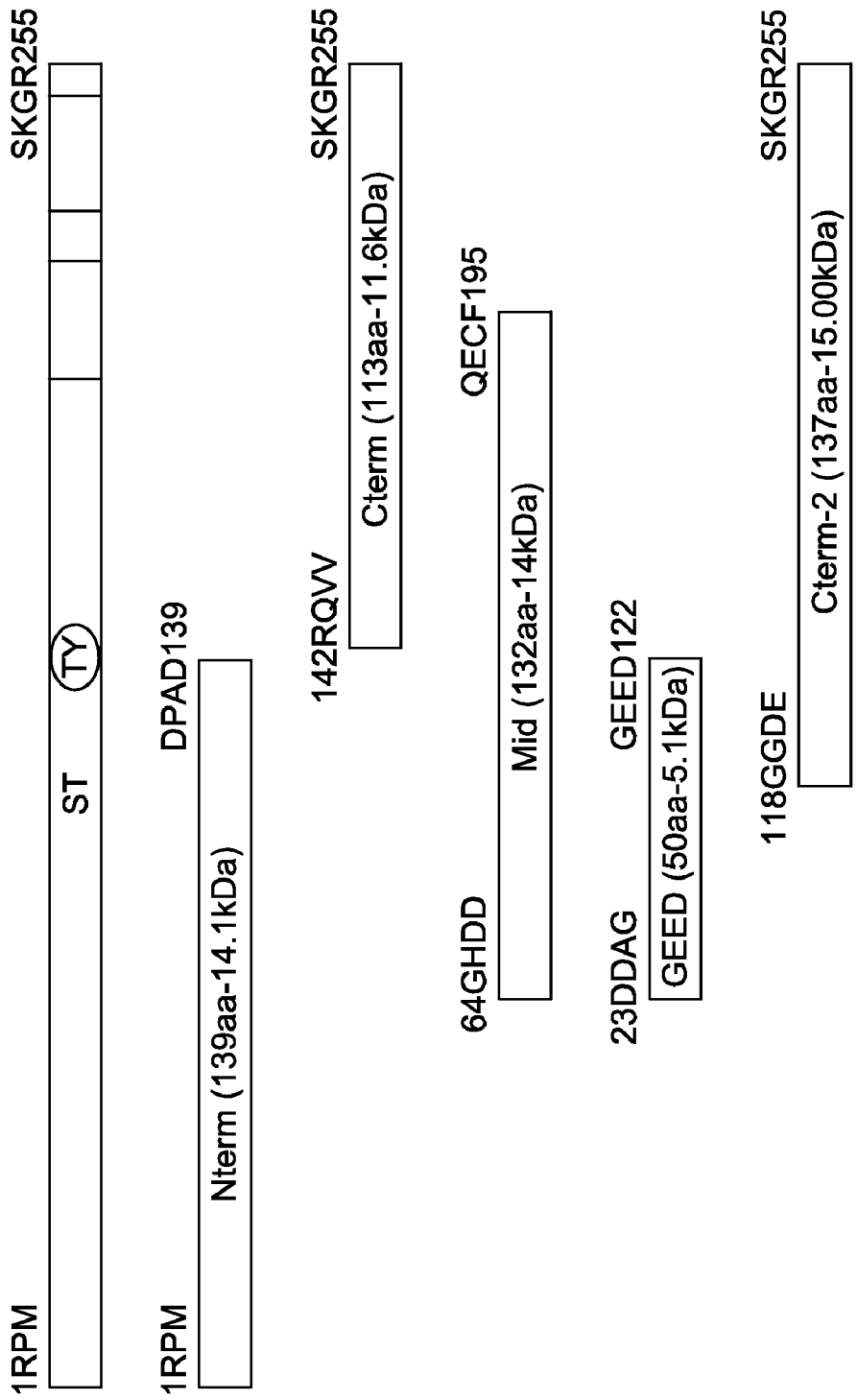
FIGS. 12A-12D show identification of the C-terminal-2 of Aegyptin without GEEDA (SEQ ID NO: 7) repeats as a high-affinity collagen binding domain. (A) Diagram of the constructs used for cloning and expression. (B) Identification of C-terminus 2 domain of Aegyptin as collagen binding motif. (C) Different concentrations of recombinant C-terminus-2 (in nM: a, 250; b, 120; c, 60; d, 30; e, 15 and f, 5) were injected over immobilized soluble collagen type I. Dissociation of Aegyptin-collagen complex was monitored for 1800 seconds, and a global two-state binding model was used to calculate kinetic parameters. (D) Human platelet-rich plasma ($2\times10^5$/ml) was incubated with C-terminus-2 (in µM: a, 0; b, 3; and c, 10) for 1 minute followed by addition of fibrillar Horm collagen (2 µg/ml, final concentration). Platelet aggregation was estimated by turbidimetry under test-tube stirring conditions. The tracings represent a typical experiment (n=6).
Figure 12B:
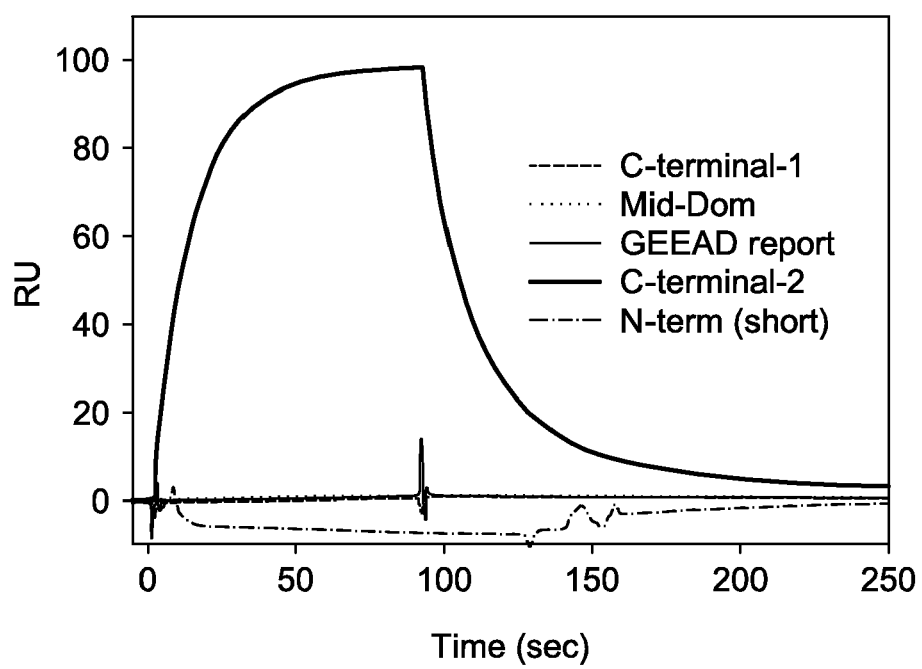
Figure 12C:
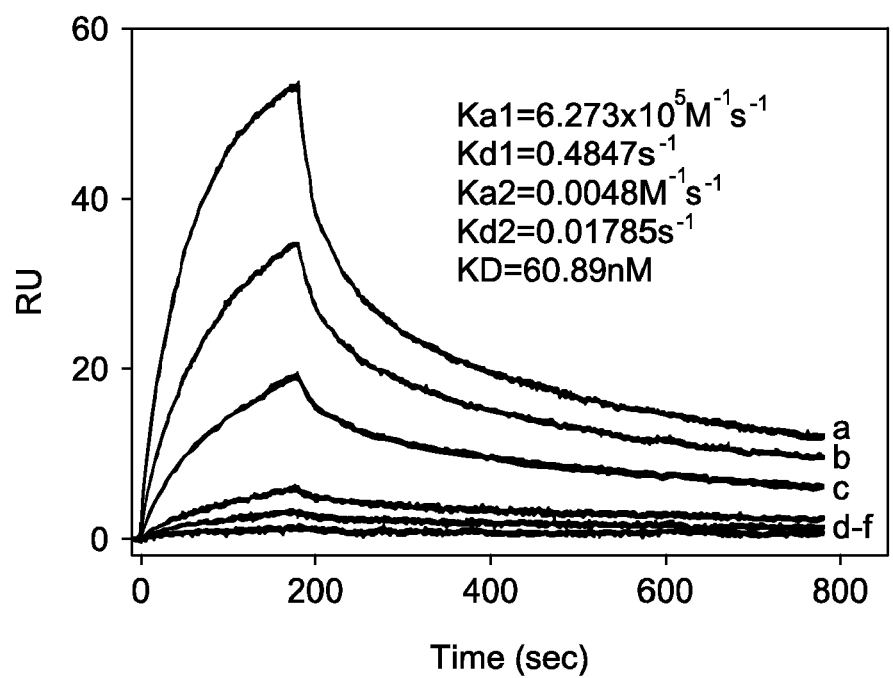
Figure 12D:
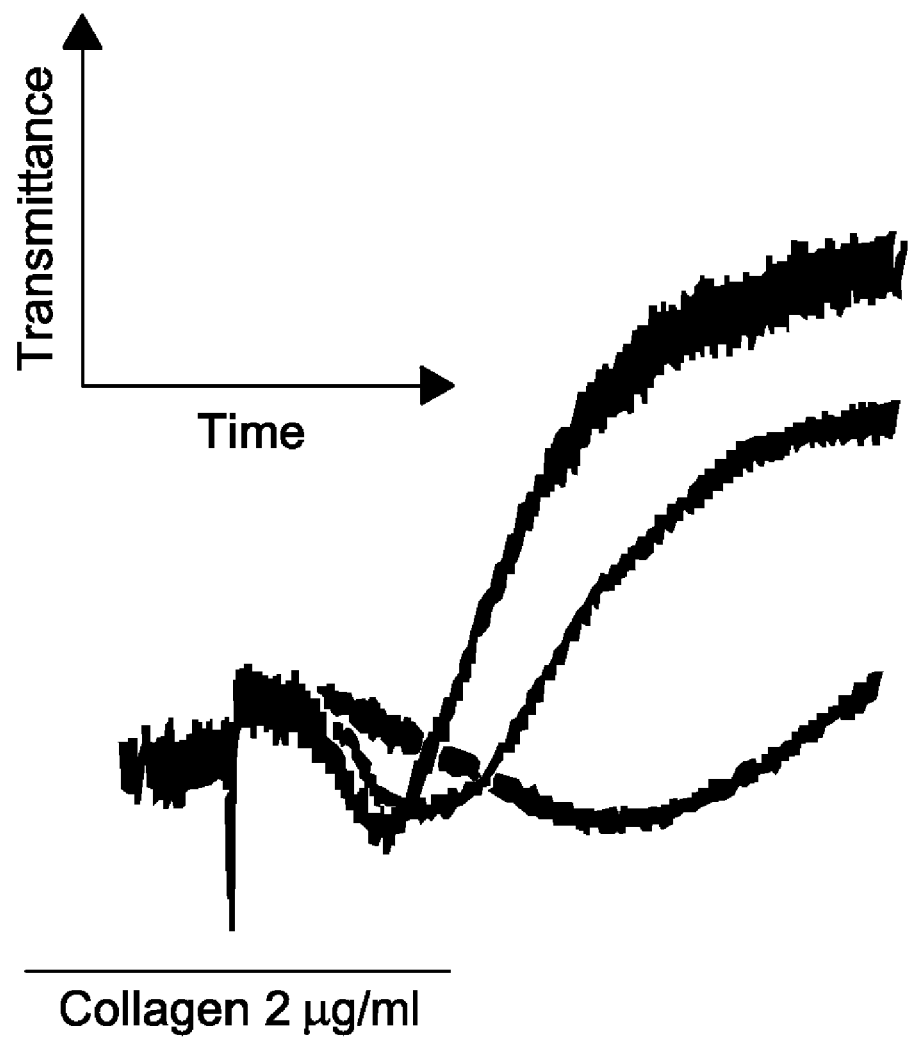

It was of interest to identify the inhibitor motifs that account for the collagen-binding properties. A number of mutants corresponding to the N-terminus (1-39 aa), C-terminus 1 (113 aa), C-terminus-2 (137 aa), Mid-sequence (132 aa) and GEEDA repeats (50 aa) of Aegyptin were expressed and purified. A diagram for each mutant is shown in FIG. 12A. Among all mutants tested, only C-terminus-2 (SEQ ID NO: 22) was shown to interact with collagen (FIG. 12B) with a $K_D \approx 60$ nM (FIG. 12C). FIG. 12D shows that C-terminus-2 prevents collagen-induced platelet aggregation with $IC_{50} \approx 3$ μM.

Aegyptin Displays Anti-Thrombotic Activity In Vivo

Figure 13:
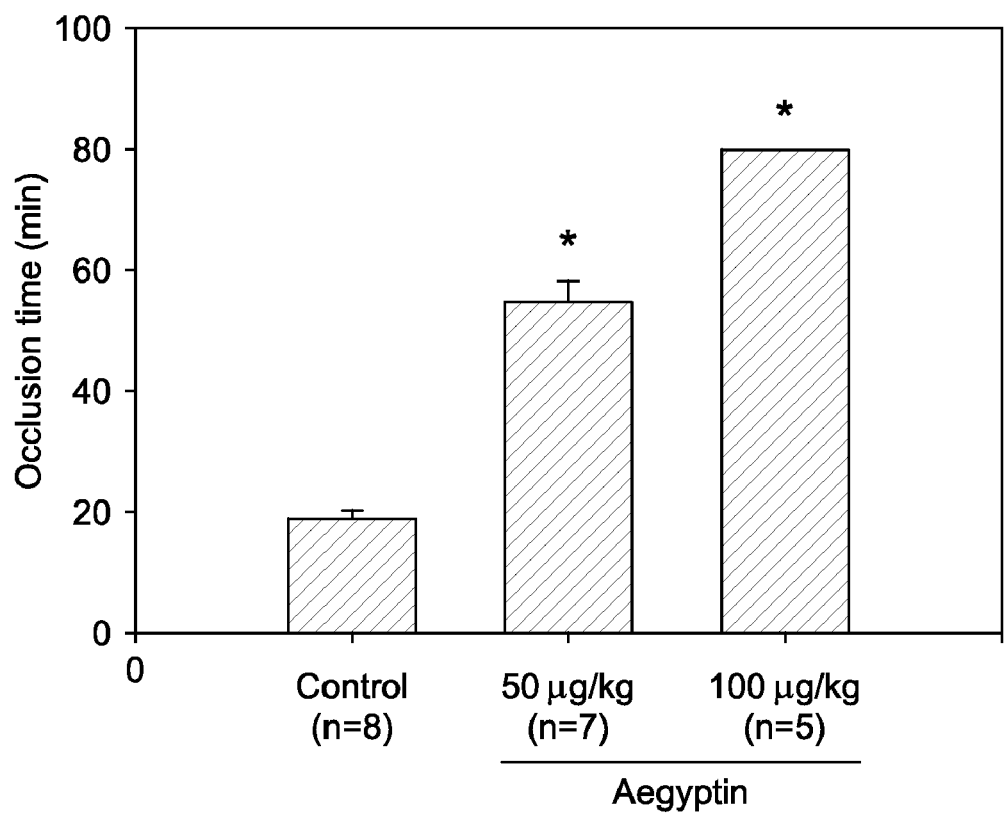
FIG. 13 shows Aegyptin prevents thrombus formation in vivo. Rats were injected in the cava vein with Aegyptin (50 or 100 µg/kg) or PBS (control) and thrombosis was induced by slow injection (over 2 min) of 90 mg/kg body weight of Rose Bengal dye into the cava vein at a concentration of 60 mg/mL. Before injection, green light laser was applied to the desired site of injury from a distance of 3 cm and remained on for 80 minutes or until stable occlusion occurred. The number of animals tested for each condition is shown in the Figure.

Next it was asked whether Aegyptin displays in vivo anti-thrombotic properties using a laser induced model of carotid injury in rats (as described by Rosen, E. D., Raymond, S., Zollman, A., Noria, F., Sandoval-Cooper, M., Shulman, A., Merz, J. L., and Castellino, F. J. 2001). Laser-induced noninvasive vascular injury models in mice generate platelet- and coagulation-dependent thrombi. *Am J Pathol* 158:1613-1622). With photochemical injury, dye (e.g. Rose Bengal) is infused into the circulation. Photo-excitation leads to oxidative injury of the vessel wall and subsequent thrombus formation. FIG. 13 shows that the blood flow of control (non-treated) animals stopped in ≈20 minutes. On the other hand, the time for thrombus formation in animals treated with 50 μg/kg Aegyptin was 50 min, while in the presence of 100 μg/kg Aegyptin thrombus formation was delayed more than 80 minutes. Notably, no bleeding was noticed in the presence of effective anti-thrombotic concentrations of Aegyptin.

DISCUSSION

The molecular mechanism has been investigated by which Aegyptin prevents platelet activation induced by collagen, a highly thrombogenic protein of the vessel wall, together with tissue factor. The data presented herein provide compelling evidence to conclude that Aegyptin inhibits platelet aggregation by a novel and dual mechanism. The first mechanism is explained by Aegyptin interaction with the collagen sequences which mediate its interaction with GPVI, vWF and integrin α2β1. Aegyptin binding to each synthetic peptide tested alone occurs in the μM range, as described for the interaction of CRP $(GPO)_{10}$ with GPVI estimated by SPR (Miura, Y., et al. 2002. *J Biol Chem* 277:46197-46204). Since binding of Aegyptin to native collagen occurs at nM concentrations (Calvo, E., et al. 2007. *J Biol Chem* 282:26928-26938) it is plausible that multiple binding sites exist for Aegyptin in collagen, resulting in a remarkably high affinity between both molecules, as observed for the tight interaction between bifunctional or multivalent proteins and their respective ligands (30-32) Francischetti, I. M., et al. 2002. *Blood* 99:3602-3612; Richardson, J. L., et al. 2000. *EMBO J* 19:5650-5660; Bergum, P. W., et al. 2001. *J Biol Chem* 276: 10063-10071). This assumption is supported by the SPR experiments which show irreversible binding of collagen to immobilized Aegyptin, and also by the fact that Aegyptin prevents platelet function associated with different ligands (Calvo, E., et al. 2007. *J Biol Chem* 282:26928-26938). The discovery that Aegyptin targets at least three distinct collagen sequences is novel and distinguishes it from other platelet inhibitors described so far (Harsfalvi, J., et al. 1995. *Blood* 85:705-711; Connolly, T. M., et al. 1992. *J Biol Chem* 267: 6893-6898; Barnes, C. S., et al. 2001 *Semin Thromb Hemost* 27:337-348; Lasser, G., et al. 2006. *Blood* 107:423-430; Harsfalvi, J., et al. 1995 *Blood* 85:705-711; Connolly, T. M., et al. 1992 *J Biol Chem* 267:6893-6898; Barnes, C. S., et al. 2001 *Semin Thromb Hemost* 27:337-348; Lasser, G., et al. 2006 *Blood* 107:423-430). It is also in agreement with the elongated structure found for Aegyptin according to gel-filtration chromatography, light scattering plot and a prediction model.

The finding that Aegyptin preferentially interacts with the RGQOGVMGFO (SEQ ID NO.: 9) peptide and also blocks its function is particularly relevant taking into account the critical role of vWF in the initiation of platelet adhesion and thrombus formation, through tethering the platelet to site of injury through binding to the platelet GPIb and collagen, particularly at high shear rates (Nieswandt, B., et al. 2003 *Blood* 102:449-461; Ruggeri, Z. M. 2002 *Nat Med* 8:1227-1234). Accordingly, platelet tethering along the injured vessel wall is reduced by 80% in mice deficient in vWF; moreover, mutants of vWF with impaired binding to collagen causes a delay of several minutes in thrombus formation in vivo (Denis, C., et al. 1998 *Proc Natl Acad Sci USA* 95:9524-9529; Marx, I., et al. 2008 *Blood*). Likewise, deficiency of GPIb has a remarkable antithrombotic effect (Konstantinides, S., et al. 2006 *J Thromb Haemost* 4:2014-2021), and recent studies have shown that inhibition of GPIb with antibodies profoundly protects mice from ischemic stroke without increasing the risk of intracranial hemorrhage (Kleinschnitz, C., et al. 2007 *Circulation* 115:2323-2330). In this regard, the experiments using a laser-induced carotid artery model in the presence of Rose Bengal (Rosen, E. D., et al. 2001 *Am J Pathol* 158:1613-1622), a model that resembles $FeCl_3$-induced thrombus formation which occurs primarily through the collagen/GPVI axis (Sachs, U. J., and Nieswandt, B. 2007 *Circ Res* 100:979-991; Furie, B., and Furie, B. C. 2005 *J Clin Invest* 115:3355-3362), confirms that Aegyptin is an effective anti-thrombotic agent in vivo and major bleeding was not observable.

Concerning other collagen-like sequences, the results presented herein demonstrate that Aegyptin binds to $(GPO)_{10}$ and GFOGER peptide (SEQ ID NO: 8) with low affinity but it is conceivable that these or related sequences together contribute to Aegyptin interaction with collagen. The main argument in support of this notion is the fact that Aegyptin effectively prevents GPVI, integrin α2β1 and vWF interaction with the native collagen in vitro and blocks the corresponding platelet responses with similar $IC_{50s}$ (Sachs, U. J., and Nieswandt, B. 2007) *Circ Res* 100:979-991). It is important to recognize that platelet adhesion and activation in primary hemostasis and in thrombus formation occurs as a result of the interaction of a number of molecules with collagen, including plasma vWF and platelet receptors such as integrin α2β1 and GPVI. In fact, it has now become clear that integrin $α_2β_1$ and GPVI synergistically mediate platelet adhesion and aggregation; while GPVI is primarily involved in cell activation and "outside-in" signaling including integrin α2β1 activation, the integrin contributes to additional GPVI-collagen interaction and stable thrombus formation. Therefore, recognition of distinct sequences by Aegyptin appears to be an effective strategy for inhibition of platelet function. The fact that Aegyptin recognizes the $(GPO)_{10}$ and also prevents GPVI binding to collagen is particularly relevant vis-à-vis the role of GPVI in thrombus formation. For example, monkeys who have been treated with anti-GPVI antibodies have thrombotic events inhibited ex vivo, (Li, H., et al. 2007 *Arterioscler Thromb Vasc Biol* 27:1199-1205; Ohlmann, P., et al. 2008 *J Thromb Haemost*; Gruner, S., et al. 2005 *Blood* 105:1492-1499) without increase in the bleeding time. Likewise, GPVI knock out mice (Massberg, S., Gawaz, M., Gruner, S., Schulte, V., Konrad, I., Zohlnhofer, D., Heinzmann, U., and Nieswandt, B. 2003. A crucial role of glycoprotein VI for platelet recruitment to the injured arterial wall in vivo. *J Exp Med* 197:41-49; Kato, K., Kanaji, T., Russell, S., Kunicki, T. J., Furihata, K., Kanaji, S., Marchese, P., Reininger, A., Ruggeri, Z. M., and Ware, J. 2003. The contribution of glycoprotein VI to stable platelet adhesion and thrombus formation illustrated by targeted gene deletion. *Blood* 102:1701-1707), or mice which GPVI has been depleted (Nieswandt, B., Schulte, V., Bergmeier, W., Mokhtari-Nejad, R., Rackebrandt, K., Cazenave, J. P., Ohlmann, P., Gachet, C., and Zirngibl, H. 2001. Long-term antithrombotic protection by in vivo depletion of platelet glycoprotein VI in mice. *J Exp Med* 193:459-469) or who have been treated with soluble GPVI dimmer (Gruner, S., Prostredna, M., Koch, M., Miura, Y., Schulte, V., Jung, S. M., Moroi, M., and Nieswandt, B. 2005. Relative antithrombotic effect of soluble GPVI dimer compared with anti-GPVI antibodies in mice. *Blood* 105:1492-1499; Massberg, S., Konrad, I., Bultmann, A., Schulz, C., Munch, G., Peluso, M., Lorenz, M., Schneider, S., Besta, F., Muller, I., et al. 2004. Soluble glycoprotein VI dimer inhibits platelet adhesion and aggregation to the injured vessel wall in vivo. *FASEB J* 18:397-399) consistently display inhibition of thrombus formation in vivo. Therefore, inhibition of GPVI-mediated platelet responses through receptor antagonism, or through blockade of sequences which mediate GPVI-collagen interaction, appears to be an attractive strategy to generate anti-thrombotics without changing the expression levels of GPVI (Nieswandt, B., Schulte, V., Bergmeier, W., Mokhtari-Nejad, R., Rackebrandt, K., Cazenave, J. P., Ohlmann, P., Gachet, C., and Zirngibl, H. 2001. Long-term antithrombotic protection by in vivo depletion of platelet glycoprotein VI in mice. *J Exp Med* 193:459-469).

The sensorgrams showing the high-affinity binding of Aegyptin to RGQOGVMGF peptide (SEQ ID NO: 9) confirms that Aegyptin recognizes specific sequences in collagen and no minimal number of GPP/GPO stretches is necessary for binding. Moreover, because Aegyptin binds to heat-denatured collagen it is concluded that the triple helical structure is not a prerequisite for binding. Similar conclusions have been reported for Keratinocyte Growth Factor (Nieswandt, B., et al. 2001 *J Exp Med* 193:459-469), Oncostatin M (Somasundaram, R., et al. 2002 *J Biol Chem* 277:3242-3246), Interleukin 2 (Somasundaram, R., et al. 2000 *J Biol Chem* 275: 38170-38175) and PDGF (Somasundaram, R., and Schuppan, D. 1996 *J Biol Chem* 271:26884-26891) binding to collagen which is not prevented by reduction and alkylation, or heat denaturation. Notably, collagen is thermally unstable at body temperature and has been reported to display a random coil rather then triple helix structure only. Further, denatured collagen modulates the function of fibroblasts and promotes wound healing indicating it is biologically active (Egles, C., et al. 2008 *J Invest Dermatol*). Therefore, it is plausible that Aegyptin recognizes specific primary sequences found in native or denatured triple helical collagen molecule in vivo resulting in tight complex formation. Actually, this effect appears to have potential therapeutic implications taking into account the role of matrix (collagen)-associated cytokine and mitogens in angiogenesis, inflammation and fibrosis in one hand and thrombus formation and atherosclerosis on the other.

Notably, the results presented herein unambiguously show that the second mechanism by which Aegyptin prevents platelet aggregation is through unwinding of the collagen triple helix. This conclusion is supported by CD experiments, which demonstrated a conformational change of the collagen molecule, herein identified as a reduction in poly-proline II structure resulting in a remarkable decrease of ellipticity. Similar conclusions were attained by AFM, which reveals that the pattern of spiral disposition typical of collagen is globally affected by Aegyptin, with important changes in height and width of the molecule. It is concluded that the strands making up the rope-shaped structure that characterize collagen, separate and open up in the presence of the inhibitor. While the relative contribution of unwinding versus interaction of specific sequences for the inhibition of platelet functions by Aegyptin remains to be determined, a working hypothesis emerges where Aegyptin binding to collagen is accompanied by global unwinding without cleavage resulting in loss of collagen interaction with major physiological ligands. This is a unique inhibitory mechanism described so far for a platelet aggregation inhibitor. On the other hand, collagenase (metalloprotease, MMP-1) or gelatinase (MMP-2) causes a local unwinding of the triple helical before peptide bond hydrolysis occurs, by a mechanism intensely debated. It is therefore remarkable that evolutionary pressure took place in mosquitoes salivary glands to produce a protein like Aegyptin and AAPP, and the results presented herein also underscore the critical role of collagen in physiology in general and hemostasis in particular. Further, protein sequences compatible with the collagen molecule have been identified by mass spectrometry in mammoths and also in dinosaurs (Asara, J. M., et al. *Science* 316:280-285), a species displaying rudimentary platelets (thrombocytes) (Brass, L. F. 2005 *J Clin Invest* 115:3329-3331), and which coexisted with bloodsucking mosquitoes reportedly found at least 50 million years ago.

The use of recombinant proteins as antithrombotic in vivo is often hampered by antigenicity or high molecular weight of the proteins. In an attempt to reduce the potential antigenicity and the molecular weight of Aegyptin, and also to identify a binding domain responsible for its activity, a series of mutants were engineered. The rationale for choosing specific mutants was based on the repetitive sequence GEEDA found in Aegyptin, the pattern of cysteines, and the characteristics of the N-terminus and C-terminus of the inhibitor. The findings presented herein clearly show that the GEEDA motif that provides a signature for Aegyptin does not play a major role in collagen-binding properties when tested alone. Likewise, the N-terminus, mid-sequences and C-terminus-1 displaying all 4 cysteines but without GEEDA repeats were devoid of activity. However, the C-terminus-2 of Aegyptin that display 24 aa more than C-terminus-1 plus a TY sequence highly conserved in the members of the 30 kDa family of proteins (Jariyapan, N., et al. 2006. *J Med Entomol* 43:867-874; Cazares-Raga, F. E., et al. 2007 *Insect Mol Biol* 16:187-198; Francischetti, I. M., et al. 2002 *J Exp Biol* 205:2429-2451) was relatively effective for binding to and inhibition of collagen-induced platelet activation. Therefore, it was concluded that the GEEDA repeats have an accessory role in mediating Aegyptin-collagen interaction, but it is not per se a fundamental sequence that mediates inhibitor-collagen interaction. Interestingly, the C-terminus of Aegyptin has been identified as a highly ordered region, which is often associated with molecular recognition. Accordingly, it is plausible to envisage Aegyptin as a molecule or as a prototype to develop inhibitors of collagen interaction with physiological ligands in a number of pathological conditions.

REFERENCES

1. Ribeiro J M, Francischetti I M. Role of arthropod saliva in blood feeding: sialome and post-sialome perspectives. Annu Rev Entomol. 2003; 48:73-88.
2. Champagne D E, Ribeiro J M. Sialokinin I and II: vasodilatory tachykinins from the yellow fever mosquito *Aedes aegypti*. Proc Natl Acad Sci USA. 1994; 91:138-142.
3. Ribeiro J M, Hazzard J M, Nussenzveig R H, Champagne D E, Walker F A. Reversible binding of nitric oxide by a salivary heme protein from a bloodsucking insect. Science. 1993; 260:539-541.
4. Stassens P, Bergum P W, Gansemans Y, et al. Anticoagulant repertoire of the hookworm *Ancylostoma caninum*. Proc Natl Acad Sci USA. 1996; 93:2149-2154.
5. Francischetti I M, Valenzuela J G, Andersen J F, Mather T N, Ribeiro J M. Ixolaris, a novel recombinant tissue factor pathway inhibitor (TFPI) from the salivary gland of the tick, *Ixodes scapularis*: identification of factor X and factor Xa as scaffolds for the inhibition of factor VIIa/tissue factor complex. Blood. 2002; 99:3602-3612.
6. Keller P M, Waxman L, Arnold B A, Schultz L D, Condra C, Connolly T M. Cloning of the cDNA and expression of moubatin, an inhibitor of platelet aggregation. J Biol Chem. 1993; 268:5450-5456.
7. Mans B J, Louw A I, Neitz A W. Savignygrin, a platelet aggregation inhibitor from the soft tick *Ornithodoros savignyi*, presents the RGD integrin recognition motif on the Kunitz-BPTI fold. J Biol Chem. 2002; 277:21371-21378.
8. Francischetti I M, Ribeiro J M, Champagne D, Andersen J. Purification, cloning, expression, and mechanism of action of a novel platelet aggregation inhibitor from the salivary gland of the blood-sucking bug, *Rhodnius prolixus*. J Biol Chem. 2000; 275:12639-12650.
9. Andersen J F, Francischetti I M, Valenzuela J G, Schuck P, Ribeiro J M. Inhibition of hemostasis by a high affinity biogenic amine-binding protein from the saliva of a blood-feeding insect. J Biol Chem. 2003; 278:4611-4617.
10. Calvo E, Mans B J, Andersen J F, Ribeiro J M. Function and evolution of a mosquito salivary protein family. J Biol Chem. 2006; 281:1935-1942.
11. Valenzuela J G, Charlab R, Galperin M Y, Ribeiro J M. Purification, cloning, and expression of an apyrase from the bed bug *Cimex lectularius*. A new type of nucleotide-binding enzyme. J Biol Chem. 1998; 273:30583-30590.
12. Ribeiro J M, Francischetti I M. Platelet-activating-factor-hydrolyzing phospholipase C in the salivary glands and saliva of the mosquito *Culex quinquefasciatus*. J Exp Biol. 2001; 204:3887-3894.
13. Harsfalvi J, Stassen J M, Hoylaerts M F, et al. Calin from *Hirudo medicinalis*, an inhibitor of von Willebrand factor binding to collagen under static and flow conditions. Blood. 1995; 85:705-711.
14. Connolly T M, Jacobs J W, Condra C. An inhibitor of collagen-stimulated platelet activation from the salivary glands of the *Haementeria officinalis* leech. I. Identification, isolation, and characterization. J Biol Chem. 1992; 267:6893-6898.
15. Barnes C S, Krafft B, Frech M, et al. Production and characterization of saratin, an inhibitor of von Willebrand factor-dependent platelet adhesion to collagen. Semin Thromb Hemost. 2001; 27:337-348.
16. Francischetti I M, Valenzuela J G, Pham V M, Garfield M K, Ribeiro J M. Toward a catalog for the transcripts and proteins (sialome) from the salivary gland of the malaria vector *Anopheles gambiae*. J Exp Biol. 2002; 205:2429-2451.

17. Ribeiro J M, Area B, Lombardo F, et al. An annotated catalogue of salivary gland transcripts in the adult female mosquito, *Aedes aegypti*. BMC Genomics. 2007; 8:6.
18. Calvo E, Andersen J, Francischetti I M, et al. The transcriptome of adult female *Anopheles darlingi* salivary glands. Insect Mol Biol. 2004; 13:73-88.
19. Ribeiro J M, Charlab R, Pham V M, Garfield M, Valenzuela J G. An insight into the salivary transcriptome and proteome of the adult female mosquito *Culex pipiens* quinquefasciatus. Insect Biochem Mol Biol. 2004; 34:543-563.
20. Nazareth R A, Tomaz L S, Ortiz-Costa S, et al. Antithrombotic properties of Ixolaris, a potent inhibitor of the extrinsic pathway of the coagulation cascade. Thromb Haemost. 2006; 96:7-13.
21. Jariyapan N, Choochote W, Jitpakdi A, et al. A glycine- and glutamate-rich protein is female salivary gland-specific and abundant in the malaria vector *Anopheles dirus* B (Diptera: Culicidae). J Med Entomol. 2006; 43:867-874.
22. Cazares-Raga F E, Gonzalez-Lazaro M, Montero-Solis C, et al. GP35 ANOAL, an abundant acidic glycoprotein of female *Anopheles albimanus* saliva. Insect Mol Biol. 2007; 16:187-198.
23. Nieswandt B, Watson S P. Platelet-collagen interaction: is GPVI the central receptor? Blood. 2003; 102:449-461.
24. Ruggeri Z M. Platelets in atherothrombosis. Nat Med. 2002; 8:1227-1234.
25. Farndale R W, Sixma J J, Barnes M J, de Groot P G. The role of collagen in thrombosis and hemostasis. J Thromb Haemost. 2004; 2:561-573.
26. Savage B, Almus-Jacobs F, Ruggeri Z M. Specific synergy of multiple substrate-receptor interactions in platelet thrombus formation under flow. Cell. 1998; 94:657-666.
27. Moroi M, Jung S M, Nomura S, Sekiguchi S, Ordinas A, Diaz-Ricart M. Analysis of the involvement of the von Willebrand factor-glycoprotein Ib interaction in platelet adhesion to a collagen-coated surface under flow conditions. Blood. 1997; 90:4413-4424.
28. Auger J M, Kuijpers M J, Senis Y A, Watson S P, Heemskerk J W. Adhesion of human and mouse platelets to collagen under shear: a unifying model. Faseb J. 2005; 19:825-827.
29. Sarratt K L, Chen H, Zutter M M, Santoro S A, Hammer D A, Kahn M L. GPVI and alpha2beta1 play independent critical roles during platelet adhesion and aggregate formation to collagen under flow. Blood. 2005; 106:1268-1277.
30. Kato K, Kanaji T, Russell S, et al. The contribution of glycoprotein VI to stable platelet adhesion and thrombus formation illustrated by targeted gene deletion. Blood. 2003; 102:1701-1707.
31. Lecut C, Arocas V, Ulrichts H, et al. Identification of residues within human glycoprotein VI involved in the binding to collagen: evidence for the existence of distinct binding sites. J Biol Chem. 2004; 279:52293-52299.
32. Jung S M, Moroi M. Signal-transducing mechanisms involved in activation of the platelet collagen receptor integrin alpha(2)beta(1). J Biol Chem. 2000; 275:8016-8026.
33. Massberg S, Gawaz M, Gruner S, et al. A crucial role of glycoprotein VI for platelet recruitment to the injured arterial wall in vivo. J Exp Med. 2003; 197:41-49.
34. Kuijpers M J, Schulte V, Bergmeier W, et al. Complementary roles of glycoprotein VI and alpha2beta1 integrin in collagen-induced thrombus formation in flowing whole blood ex vivo. Faseb J. 2003; 17:685-687.
35. Chen H, Kahn M L. Reciprocal signaling by integrin and nonintegrin receptors during collagen activation of platelets. Mol Cell Biol. 2003; 23:4764-4777.
36. Francischetti I M, Saliou B, Leduc M, et al. Convulxin, a potent platelet-aggregating protein from *Crotalus durissus terrificus* venom, specifically binds to platelets. Toxicon. 1997; 35:1217-1228.
37. Jandrot-Perrus M, Busfield S, Lagrue A H, et al. Cloning, characterization, and functional studies of human and mouse glycoprotein VI: a platelet-specific collagen receptor from the immunoglobulin superfamily. Blood. 2000; 96:1798-1807.
38. Ribeiro J M, Sarkis J J, Rossignol P A, Spielman A. Salivary apyrase of *Aedes aegypti*: characterization and secretory fate. Comp Biochem Physiol B. 1984; 79:81-86.
39. Tokumasu F, Dvorak J. Development and application of quantum dots for immunocytochemistry of human erythrocytes. J Microsc. 2003; 211:256-261.
40. Cruz M A, Chen J, Whitelock J L, Morales L D, Lopez J A. The platelet glycoprotein Ib-von Willebrand factor interaction activates the collagen receptor alpha2beta1 to bind collagen: activation-dependent conformational change of the alpha2-I domain. Blood. 2005; 105:1986-1991.
41. Francischetti I M, Seydel K B, Monteiro R Q, et al. *Plasmodium falciparum*-infected erythrocytes induce tissue factor expression in endothelial cells and support the assembly of multimolecular coagulation complexes. J Thromb Haemost. 2007; 5:155-165.
42. Nakamura T, Jamieson G A, Okuma M, Kambayashi J, Tandon N N. Platelet adhesion to native type I collagen fibrils. Role of GPVI in divalent cation-dependent and -independent adhesion and thromboxane A2 generation. J Biol Chem. 1998; 273:4338-4344.
43. Jung S M, Moroi M. Platelets interact with soluble and insoluble collagens through characteristically different reactions. J Biol Chem. 1998; 273:14827-14837.
44. Savage B, Ginsberg M H, Ruggeri Z M. Influence of fibrillar collagen structure on the mechanisms of platelet thrombus formation under flow. Blood. 1999; 94:2704-2715.
45. Atkinson B T, Jarvis G E, Watson S P. Activation of GPVI by collagen is regulated by alpha2beta1 and secondary mediators. J Thromb Haemost. 2003; 1:1278-1287.
46. Barnes M J, Farndale R W. Collagens and atherosclerosis. Exp Gerontol. 1999; 34:513-525.
47. Lisman T, Raynal N, Groeneveld D, et al. A single high-affinity binding site for von Willebrand factor in collagen III, identified using synthetic triple-helical peptides. Blood. 2006; 108:3753-3756.
48. Smethurst P A, Onley D J, Jarvis G E, et al. Structural basis for the platelet-collagen interaction: the smallest motif within collagen that recognizes and activates platelet Glycoprotein VI contains two glycine-proline-hydroxyproline triplets. J Biol Chem. 2007; 282:1296-1304.
49. Watson S P, Auger J M, McCarty O J, Pearce A C. GPVI and integrin alphaIIb beta3 signaling in platelets. J Thromb Haemost. 2005; 3:1752-1762.
50. Gibbins J M. Platelet adhesion signalling and the regulation of thrombus formation. J Cell Sci. 2004; 117:3415-3425.
51. Munnix I C, Strehl A, Kuijpers M J, et al. The glycoprotein VI-phospholipase Cgamma2 signaling pathway controls thrombus formation induced by collagen and tissue factor in vitro and in vivo. Arterioscler Thromb Vasc Biol. 2005; 25:2673-2678.
52. Heemskerk J W, Kuijpers M J, Munnix I C, Siljander P R. Platelet collagen receptors and coagulation. A characteristic platelet response as possible target for antithrombotic treatment. Trends Cardiovasc Med. 2005; 15:86-92.

53. Raynal N, Hamaia S W, Siljander P R, et al. Use of synthetic peptides to locate novel integrin alpha2beta1-binding motifs in human collagen III. J Biol Chem. 2006; 281:3821-3831.
54. Jarvis G E, Atkinson B T, Snell D C, Watson S P. Distinct roles of GPVI and integrin alpha(2)beta(1) in platelet shape change and aggregation induced by different collagens. Br J Pharmacol. 2002; 137:107-117.
55. Morton L F, Hargreaves P G, Farndale R W, Young R D, Barnes M J. Integrin alpha 2 beta 1-independent activation of platelets by simple collagen-like peptides: collagen tertiary (triple-helical) and quaternary (polymeric) structures are sufficient alone for alpha 2 beta 1-independent platelet reactivity. Biochem J. 1995; 306 (Pt 2):337-344.
56. Knight C G, Morton L F, Onley D J, et al. Collagen-platelet interaction: Gly-Pro-Hyp is uniquely specific for platelet Gp VI and mediates platelet activation by collagen. Cardiovasc Res. 1999; 41:450-457.
57. Lasser G, Guchhait P, Ellsworth J L, et al. C1qTNF-related protein-1 (CTRP-1): a vascular wall protein that inhibits collagen-induced platelet aggregation by blocking VWF binding to collagen. Blood. 2006; 107:423-430.
58. Vilahur G, Duran X, Juan-Babot O, Casani L, Badimon L. Antithrombotic effects of saratin on human atherosclerotic plaques. Thromb Haemost. 2004; 92:191-200.
59. Davis J A, Brown A T, Alshafie T, et al. Saratin (an inhibitor of platelet-collagen interaction) decreases platelet aggregation and homocysteine-mediated postcarotid endarterectomy intimal hyperplasia in a dose-dependent manner. Am J Surg. 2004; 188:778-785.
60. van Zanten G H, Connolly T M, Schiphorst M E, de Graaf S, Slootweg P J, Sixma J J. Recombinant leech antiplatelet protein specifically blocks platelet deposition on collagen surfaces under flow conditions. Arterioscler Thromb Vasc Biol. 1995; 15:1424-1431.
61. Penz S, Reininger A J, Brandi R, et al. Human atheromatous plaques stimulate thrombus formation by activating platelet glycoprotein VI. Faseb J. 2005; 19:898-909.
62. Toschi V, Gallo R, Lettino M, et al. Tissue factor modulates the thrombogenicity of human atherosclerotic plaques. Circulation. 1997; 95:594-599.
63. Furie B, Furie B C. Thrombus formation in vivo. J Clin Invest. 2005; 115:3355-3362.
64. Raines E W, Koyama H, Carragher N O. The extracellular matrix dynamically regulates smooth muscle cell responsiveness to PDGF. Ann N Y Acad Sci. 2000; 902:39-51; discussion 51-32.

What is claimed is:

1. A method of disrupting platelet adhesion in a subject comprising: identifying a subject in need of a molecule that disrupts platelet adhesion and providing said subject with a therapeutically effective amount of said molecule, wherein said molecule is an Aegyptin polypeptide or a fragment thereof.

2. The method of claim 1, wherein said subject is human.

3. A method of reducing clot formation comprising:
identifying a subject in need of a reduction in clot formation and providing to said subject a therapeutically effective amount of an Aegyptin polypeptide or a fragment thereof.

4. The method of claim 3, wherein said subject in need of a reduction in clot formation suffers from a thrombosis-related disease.

5. The method of claim 4, wherein said thrombosis-related disease is any one of: coronary thrombosis, pulmonary embolism, myocardial infarction, deep vein thrombosis, cerebral thrombosis, unstable angina, disseminated intravascular coagulation (DIC), postoperative fibrinolytic shutdown, or a rapid thrombogenic action which can occur following implantation of a medical device.

6. A method of treating a thrombogenic disease comprising:
identifying a subject suffering from a thrombogenic disease and providing to said subject a therapeutically effective amount of an Aegyptin polypeptide or a fragment thereof.

7. The method of claim 6, wherein said thrombogenic disease is any one of: coronary thrombosis, pulmonary embolism, myocardial infarction, deep vein thrombosis, cerebral thrombosis, unstable angina, disseminated intravascular coagulation (DIC), postoperative fibrinolytic shutdown, or a rapid thrombogenic action which can occur following implantation of a medical device.

* * * * *